US011857378B1

(12) United States Patent
Bojarski et al.

(10) Patent No.: US 11,857,378 B1
(45) Date of Patent: Jan. 2, 2024

(54) SYSTEMS FOR ADJUSTING AND TRACKING HEAD MOUNTED DISPLAYS DURING SURGERY INCLUDING WITH SURGICAL HELMETS

(71) Applicant: OnPoint Medical, Inc., Bedford, MA (US)

(72) Inventors: Raymond Bojarski, Attleboro, MA (US); Chuang-Jang Chiou, Bedford, MA (US); Philipp K. Lang, Lexington, MA (US); Daniel Steines, Lexington, MA (US)

(73) Assignee: OnPoint Medical, Inc., Franconia, NH (US)

( * ) Notice: Subject to any disclaimer, the term of this patent is extended or adjusted under 35 U.S.C. 154(b) by 486 days.

(21) Appl. No.: 16/791,021

(22) Filed: Feb. 14, 2020

Related U.S. Application Data

(60) Provisional application No. 62/817,595, filed on Mar. 13, 2019, provisional application No. 62/805,824, filed on Feb. 14, 2019.

(51) Int. Cl.
  *G09G 5/38* (2006.01)
  *G02B 27/01* (2006.01)
  (Continued)

(52) U.S. Cl.
  CPC .......... *A61B 90/37* (2016.02); *G02B 27/0176* (2013.01); *G06F 1/163* (2013.01);
  (Continued)

(58) Field of Classification Search
  CPC .............. A61B 90/37; A61B 2090/365; A61B 2034/2055; A61B 34/30; A61B 34/20
  (Continued)

(56) References Cited

U.S. PATENT DOCUMENTS 5,054,480 A   10/1991   Bare et al.
5,526,812 A   6/1996    Dumoulin et al.
(Continued)

FOREIGN PATENT DOCUMENTS

| CA | 3035258 A1 * | 4/2018 | ............ A61B 34/25 |
|----|--------------|--------|-------------------------|
| EP | 1028659      | 2/2004 |                         |

(Continued)

OTHER PUBLICATIONS

Abe et al., "A Novel 3D Guidance System Using Augmented Reality for Percutaneous Vertebroplasty", Journal of Neurological Spine, vol. 19, pp. 492-501, Oct. 2013.
(Continued)

*Primary Examiner* — Javid A Amini
(74) *Attorney, Agent, or Firm* — Greenberg Traurig, LLP; Natalie Salem; Barry Schindler

(57) ABSTRACT

Aspects of the disclosure relate to a system comprising a head mounted display, an adjusting mechanism, and a connecting mechanism, wherein the head mounted display is configured to be worn on a head of a user under a cover of a surgical helmet so that the display of the head mounted display is adjacent to a transparent portion of the cover, wherein the adjusting mechanism is configured to adjust at least a position of the head mounted display in relationship to the user's eyes, and wherein the connecting mechanism is configured to couple the head mounted display to the surgical helmet. Aspects of the disclosure relate to a system for tracking a head mounted display when used in connection with a surgical helmet and a cover for the surgical helmet.

18 Claims, 37 Drawing Sheets

(51) Int. Cl.
*G06F 3/01* (2006.01)
*A61B 90/00* (2016.01)
*G06F 1/16* (2006.01)
*A61B 90/50* (2016.01)
*A61B 17/00* (2006.01)

(52) U.S. Cl.
CPC .............. *A61B 2017/00907* (2013.01); *A61B 2090/372* (2016.02); *A61B 2090/502* (2016.02); *G02B 2027/0159* (2013.01)

(58) Field of Classification Search
USPC .................................................. 361/679.03
See application file for complete search history.

(56) References Cited

U.S. PATENT DOCUMENTS

| | | |
|---|---|---|
| 5,676,673 A | 10/1997 | Ferre et al. |
| 5,800,352 A | 9/1998 | Ferre et al. |
| 5,803,089 A | 9/1998 | Ferre et al. |
| 5,829,444 A | 11/1998 | Ferre et al. |
| 5,873,822 A | 2/1999 | Ferre et al. |
| D415,146 S | 10/1999 | Hori |
| 5,967,980 A | 10/1999 | Ferre et al. |
| 6,175,756 B1 | 1/2001 | Ferre et al. |
| 6,341,231 B1 | 1/2002 | Ferre et al. |
| 6,396,497 B1 | 5/2002 | Reichlen |
| 6,445,943 B1 | 9/2002 | Ferre et al. |
| 6,481,019 B2 | 11/2002 | Diaz et al. |
| 6,599,247 B1 | 7/2003 | Stetten |
| 6,714,810 B2 | 3/2004 | Grzeszczuk et al. |
| 7,130,676 B2 | 10/2006 | Barrick |
| 7,752,682 B2 | 7/2010 | VanDerWoude et al. |
| 7,774,044 B2 | 8/2010 | Sauer et al. |
| 7,812,815 B2 | 10/2010 | Banerjee et al. |
| 8,320,612 B2 | 11/2012 | Knobel et al. |
| 8,730,266 B2 | 5/2014 | Brown et al. |
| 8,819,869 B2 | 9/2014 | VanDerWoude et al. |
| 8,989,843 B2 | 3/2015 | Chien |
| 9,068,820 B2 | 6/2015 | Kosmecki et al. |
| 9,068,824 B2 | 6/2015 | Findeisen et al. |
| 9,123,155 B2 | 9/2015 | Cunningham et al. |
| 9,183,560 B2 | 11/2015 | Abelow |
| 9,215,293 B2 | 12/2015 | Miller |
| 9,299,138 B2 | 3/2016 | Zellner et al. |
| 9,310,559 B2 | 4/2016 | Macnamara |
| 9,311,284 B2 | 4/2016 | Warila et al. |
| 9,389,424 B1 | 7/2016 | Schowengerdt |
| 9,417,452 B2 | 8/2016 | Schowengerdt et al. |
| 9,429,752 B2 | 8/2016 | Schowengerdt et al. |
| 9,503,681 B1 | 11/2016 | Popescu et al. |
| 9,547,940 B1 | 1/2017 | Sun et al. |
| 9,582,717 B2 | 2/2017 | Lee et al. |
| 9,792,721 B2 | 10/2017 | Kosmecki et al. |
| 9,861,446 B2 | 1/2018 | Lang |
| 9,928,629 B2 | 3/2018 | Benishti et al. |
| 9,980,780 B2 | 5/2018 | Lang |
| 10,078,221 B2 | 9/2018 | Pilkinton et al. |
| 10,136,952 B2 | 11/2018 | Couture et al. |
| 10,154,239 B2 | 12/2018 | Casas |
| 10,159,530 B2 | 12/2018 | Lang |
| 10,278,777 B1 | 5/2019 | Lang |
| 10,292,768 B2 | 5/2019 | Lang |
| 10,368,947 B2 | 8/2019 | Lang |
| 10,382,748 B2 | 8/2019 | Benishti et al. |
| 10,405,927 B1 | 9/2019 | Lang |
| 10,437,070 B2 * | 10/2019 | Pombo ............... G02B 27/0172 |
| 10,502,363 B2 * | 12/2019 | Edwards ................ F16M 13/04 |
| 10,546,423 B2 * | 1/2020 | Jones ................... G06T 19/006 |
| 10,603,113 B2 | 3/2020 | Lang |
| 10,743,939 B1 | 8/2020 | Lang |
| 10,799,296 B2 | 10/2020 | Lang |
| 10,849,693 B2 | 12/2020 | Lang |
| 11,013,560 B2 | 5/2021 | Lang |
| 11,172,990 B2 | 11/2021 | Lang |
| 11,311,341 B2 | 4/2022 | Lang |
| 2001/0041838 A1 | 11/2001 | Holupka et al. |
| 2002/0082498 A1 | 6/2002 | Wendt et al. |
| 2002/0016349 A1 | 11/2002 | Sauer |
| 2005/0113846 A1 | 5/2005 | Carson |
| 2005/0215879 A1 | 9/2005 | Chuanggui |
| 2005/0028146 A1 | 12/2005 | Marquart et al. |
| 2005/0267353 A1 | 12/2005 | Marquart et al. |
| 2005/0281465 A1 | 12/2005 | Marquart et al. |
| 2006/0142739 A1 | 6/2006 | Disilestro et al. |
| 2007/0015999 A1 | 1/2007 | Heldreth et al. |
| 2007/0035511 A1 | 2/2007 | Banerjee et al. |
| 2007/0038944 A1 | 2/2007 | Carignano et al. |
| 2007/0236514 A1 | 10/2007 | Agusanto et al. |
| 2007/0276234 A1 | 11/2007 | Shahidi |
| 2009/0068620 A1 | 3/2009 | Knobel et al. |
| 2009/0089081 A1 | 4/2009 | Haddad |
| 2009/0138019 A1 | 5/2009 | Wasielewski |
| 2009/0267805 A1 | 10/2009 | Jin et al. |
| 2010/0001927 A1 * | 1/2010 | Hough .................. G02B 7/002 345/8 |
| 2011/0190637 A1 | 8/2011 | Knobel et al. |
| 2012/0075464 A1 | 3/2012 | Derenne et al. |
| 2013/0093829 A1 | 4/2013 | Rosenblatt et al. |
| 2013/0096373 A1 | 4/2013 | Chabanas et al. |
| 2013/0116574 A1 | 5/2013 | Knobel et al. |
| 2013/0169683 A1 * | 7/2013 | Perez ..................... G06F 21/32 382/117 |
| 2013/0261503 A1 | 10/2013 | Sherman et al. |
| 2013/0261504 A1 | 10/2013 | Claypool et al. |
| 2013/0261633 A1 | 10/2013 | Thornberry |
| 2013/0296682 A1 | 11/2013 | Clavin et al. |
| 2013/0326364 A1 | 12/2013 | Latta et al. |
| 2014/0081659 A1 | 3/2014 | Nawana et al. |
| 2014/0085203 A1 | 3/2014 | Kobayashi |
| 2014/0088941 A1 | 3/2014 | Banerjee et al. |
| 2014/0118335 A1 | 5/2014 | Gurman |
| 2014/0135746 A1 | 5/2014 | Schoepp |
| 2014/0198190 A1 | 7/2014 | Okumu |
| 2014/0218366 A1 | 8/2014 | Kosmecki et al. |
| 2014/0275760 A1 | 9/2014 | Lee et al. |
| 2014/0303491 A1 | 10/2014 | Shekhar et al. |
| 2014/0334670 A1 | 11/2014 | Guigues et al. |
| 2015/0077312 A1 * | 3/2015 | Wang ..................... G09G 3/02 345/7 |
| 2015/0100067 A1 | 4/2015 | Cavanagh et al. |
| 2015/0206218 A1 | 7/2015 | Banerjee et al. |
| 2015/0264339 A1 * | 9/2015 | Riedel ................. H04N 13/383 348/54 |
| 2015/0310668 A1 | 10/2015 | Ellerbrock |
| 2015/0366628 A1 | 12/2015 | Ingmanson |
| 2016/0163105 A1 | 6/2016 | Hong et al. |
| 2016/0182877 A1 | 6/2016 | DeLuca |
| 2016/0191887 A1 | 6/2016 | Casas |
| 2016/0206379 A1 | 7/2016 | Flett et al. |
| 2016/0220105 A1 | 8/2016 | Duret |
| 2016/0225192 A1 * | 8/2016 | Jones ..................... A61B 34/20 |
| 2016/0228193 A1 | 8/2016 | Moctezuma de la Barrera et al. |
| 2016/0287337 A1 | 10/2016 | Aram et al. |
| 2016/0324580 A1 | 11/2016 | Esterberg |
| 2016/0381256 A1 | 12/2016 | Aguirre-Valencia |
| 2017/0027651 A1 | 2/2017 | Esterberg |
| 2017/0035517 A1 | 2/2017 | Geri et al. |
| 2017/0071673 A1 | 3/2017 | Ferro et al. |
| 2017/0099479 A1 * | 4/2017 | Browd ................... A61B 34/20 |
| 2017/0108930 A1 | 4/2017 | Banerjee et al. |
| 2017/0160549 A1 | 6/2017 | Badiali et al. |
| 2017/0178375 A1 | 6/2017 | Benishti et al. |
| 2017/0202633 A1 | 7/2017 | Liu |
| 2017/0231714 A1 | 8/2017 | Kosmecki et al. |
| 2017/0258526 A1 * | 9/2017 | Lang ..................... H05K 999/99 |
| 2017/0312032 A1 | 11/2017 | Amanatullah et al. |
| 2018/0049622 A1 | 2/2018 | Ryan et al. |
| 2018/0092706 A1 * | 4/2018 | Anderson .............. A61B 34/74 |
| 2018/0116728 A1 | 5/2018 | Lang |
| 2018/0125584 A1 | 5/2018 | Lang |
| 2018/0256256 A1 | 9/2018 | May et al. |
| 2018/0263704 A1 | 9/2018 | Lang |
| 2019/0000564 A1 | 1/2019 | Navab et al. |

(56) References Cited

U.S. PATENT DOCUMENTS

| | | |
|---|---|---|
| 2019/0110842 A1 | 4/2019 | Lang |
| 2019/0192226 A1 | 6/2019 | Lang |
| 2019/0216452 A1 | 7/2019 | Nawana et al. |
| 2019/0262078 A1 | 8/2019 | Lang |
| 2019/0328462 A1* | 10/2019 | Liu .................. G16H 40/63 |
| 2019/0333480 A1* | 10/2019 | Lang ................ G06F 3/011 |
| 2019/0380784 A1 | 12/2019 | Lang |
| 2019/0380792 A1* | 12/2019 | Poltaretskyi ........ G09B 23/28 |
| 2020/0019236 A1* | 1/2020 | Parkinson ........... G06F 3/012 |
| 2020/0060767 A1 | 2/2020 | Lang |
| 2020/0163723 A1 | 5/2020 | Wolf et al. |
| 2020/0246074 A1 | 8/2020 | Lang |
| 2020/0305980 A1 | 10/2020 | Lang |
| 2021/0022808 A1 | 1/2021 | Lang |
| 2021/0043007 A1* | 2/2021 | Jones ................. G06T 19/006 |
| 2021/0106386 A1 | 4/2021 | Lang |
| 2021/0267691 A1 | 9/2021 | Lang |
| 2021/0382559 A1* | 12/2021 | Segev ................ G06F 3/017 |
| 2022/0012949 A1* | 1/2022 | Jones ................. G06F 3/012 |
| 2022/0091423 A1* | 3/2022 | Haddick .............. G06F 1/163 |

FOREIGN PATENT DOCUMENTS

| | | | |
|---|---|---|---|
| GB | 2498833 | 12/2016 | |
| WO | WO19923025157 | 12/1993 | |
| WO | WO 2005088539 | 9/2005 | |
| WO | WO 2010034117 | 4/2010 | |
| WO | WO 2014057352 | 4/2014 | |
| WO | WO 2015110859 | 7/2015 | |
| WO | WO 2015145395 | 10/2015 | |
| WO | WO 2016028828 | 2/2016 | |
| WO | WO 2016162789 | 10/2016 | |
| WO | WO 2016195401 | 12/2016 | |
| WO | WO 2016207628 | 12/2016 | |
| WO | WO 2017160651 | 9/2017 | |
| WO | WO 2018085417 | 5/2018 | |
| WO | WO 2018085691 | 5/2018 | |
| WO | 2018129234 A1 | 7/2018 | |
| WO | WO-2018129234 A1 * | 7/2018 | ......... G02B 27/0093 |
| WO | WO 2018132804 | 7/2018 | |
| WO | WO 2018052966 | 10/2018 | |
| WO | 2019148154 A1 | 8/2019 | |

OTHER PUBLICATIONS

Aguerreche L. et al., "Reconfigurable Tangible Devices for 3D Virtual Object Manipulation by Single or Multiple Users." VRST 2010, Nov. 2010, Hong Kong, Hong Kong SAR China. inria-00534095.

Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.

Anderson et al., "Virtual annotations of the surgical field through an augmented reality transparent display", The Visual Computer, vol. 32, Issue 11, pp. 1481-1498, Nov. 2016.

Armstrong et al., "A Heads-Up Display for Diabetic Limb Salvage Surgery: A View Through the Google Looking Glass"; Journal of Diabetes Science and Technology 2014, vol. 8(5) 951-956.

Azura, R., "A survey of augmented reality." Teleoperators and Virtual Environments, vol. 6, Issue 4, Aug. 1997, pp. 355-385.

Bajura, M., et al., "Merging Virtual Objects with the Real World: Seeing Ultrasound Imagery Within the Patient.", In Proceedings of SIGGRAPH '92, 1992, New York: ACM Press, pp. 203-210.

Baker et al., "The Emergence of Augmented Reality in Orthopaedic Surgery and Education", The Orthopaedic Journal at Harvard Medical School, vol. 16, pp. 8-16, Jun. 2015.

Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.

Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.

Bauer et al., "Real-Time Range Imaging in Health Care: A Survey", Time-of-Flight and Depth Imaging, Sensors, Algorithms, and Applications. Lecture Notes in Computer Science, vol. 8200, pp. 228-254, 2017.

Bauer, Sebastian, Doctoral Thesis, "Rigid and Non-Rigid Surface Registration for Range Imaging Applications in Medicine", urn:nbn:de:bvb:29-opus4-54665, Nov. 27, 2014.

Benford, S. et al., "User embodiment in collaborative virtual environments", Proceedings of the SIGCHI conference on Human factors in computing systems, CHI '95, pp. 242-249, 1995.

Besl PJ, McKay ND. 2, 1992. A method for registration of 3-D shapes. IEEE Trans PAMI, vol. 14, pp. 239-256.

Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.

Bichlmeier et al., "Virtually Extended Surgical Drilling Device: Virtual Mirror for Navigated Spine Surgery"; MICCAI 2007, Part I, LNCS 4791, pp. 434-441.

Billinghurst, et al., "The MagicBook: A Transitional AR Interface.", Computers and Graphics, Nov. 2001, pp. 745-753.

Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.

Billinghurst, M., et al., "Collaborative Mixed Reality.", Communications of the ACM 2002, vol. 45 Issue 7, pp. 64-70 (2002).

Billinghurst, M., et al., "Experiments with Face to Face Collaborative AR Interfaces.", Virtual Reality Journal, vol. 4, No. 2, (2002).

Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.

Birkfellner et al., "Computer-enhanced stereoscopic vision in a head-mounted operating binocular", Physics in Medicine & Biology, vol. 48, No. 3, pp. 49-57, Feb. 7, 2003.

Birkfellner et al., "In-Vitro Aassessment of a Registration Protocol for Image Guided Implant Dentistry", Clinical Oral Implants Research, vol. 12, Issue 1, pp. 69-78, Feb. 2001.

Blackwell et al., "An Image Overlay System for Medical Data Visualization", Medical Image Analysis vol. 4, pp. 67-72, 2000.

Blackwell et al., "Augmented Reality and Its Future in Orthopaedics", Clinical Orthopaedics & Related Research, vol. 354, pp. 111-122, Sep. 1998.

Bruker Nano Surfaces, 3D Optical Microscopy for Orthopedic Implants; Jun. 17, 2016.

Castillo et al., "Augmented Reality for Assistance of Total Knee Replacement", Journal of Electrical and Computer Engineering, vol. 2016, Article 9358369, pp. 1-6, 2016.

Catani et al., "Knee Surgery Using Computer Assisted Surgery and Robotics", Springer Heidelberg Publishing, Book, pp. 1-221, 2013.

Chandak, "MEMS Based Wireless Controlled Robot with Voice and Video Camera"; International Journal of Scientific & Engineering Research, vol. 5, Issue 4, Apr. 2014.

Charbonnier et al., "Real Virtuality: Perspectives offered by the combination of Virtual Reality headsets and Motion Capture", Artanim, Real Virtuality White Paper, Aug. 23, 2015.

Chen et al., "Development of a surgical navigation system based on augmented reality using an optical see-through head-mounted display"; Journal of Biomedical Informatics 55 (2015) 124-131.

Cruz-Neira C. et al., "The cave: audio visual experience automatic virtual environment.", Commun. ACM, vol. 35, No. 6, pp. 64-72, Jun. 1992.

Cui et al., "KinectAvatar: Fully Automatic Body Capture Using a Single Kinect", ACCV'12 Proceedings of the 11th International Conference on Computer Vision—vol. 2, pp. 133-147, Nov. 2012.

(56) References Cited

OTHER PUBLICATIONS

Daniel and Ramos, "Augmented Reality for Assistance of Total Knee Replacement", Journal of Electrical and Computer Engineering, vol. 2016, Article ID 9358369, Hindawi Publishing Corporation.
Davies et al., "Computer Assisted Orthopaedic Surgery", 8th Annual Meeting of CAOS—International Proceedings, Apr. 2008.
DeLambert et al., "Electromagnetic Tracking for Registration and Navigation in Endovascular Aneurysm Repair: A Phantom Study" European Journal of Vascular and Endovascular Surgery, vol. 43, pp. 684-689, 2012.
Draelos, Mark, "The Kinect Up Close: Modifications for Short-Range Depth Imaging", NC State Theses and Dissertations, pp. 1-88, Mar. 26, 2012.
Elmi-Terander et al., "Surgical Navigation Technology Based on Augmented Reality and Integrated 3D Intraoperative Imaging"; Spine Surgery, vol. 41, No. 21, pp. E1303-E1311, 2016.
Ferrari et al., "Video See-Through in the Clinical Practice", 1st International Workshop on Engineering Interactive Computing Systems for Medicine and Health Care, EICS4Med. vol. 727, pp. 19-24, 2011.
Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.
Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).
Flusser et al., "Image Fusion: Principles, Methods and Applications", Tutorial EISIPCO 2007 Lecture Notes.
Fritz et al., "Augmented Reality Visualization with Image Overlay for MRI-Guided Intervention: Accuracy for Lumbar Spinal Procedures with a 1.5-T MRI System", Vascular and Interventional Radiology, AJR: 198, Mar. 2012.
Fritz et al., "Augmented Reality Visualization with Use of Image Overlay Technology for MR Imaging-guided Interventions: Assessment of Performance in Cadaceric Shoulder and Hip Arthrography at 1.5T"; Radiology: vol. 265, No. 1, Oct. 2012, pp. 254-259.
Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).
Garrido-Jurado, S.; Muñoz-Salinas, R.; Madrid-Cuevas, F. J.; Marín-Jiménez, M. J. (2014): Automatic generation and detection of highly reliable fiducial markers under occlusion. In: Pattern Recognition 47 (6), S. 2280-2292. DOI: 10.1016/j.patcog.2014.01.005.
Gavaghan et al., "Augmented Reality Image Overlay Projection for Image Guided Open Liver Ablation of Metastatic Liver Cancer"; C.A. Linte et al. (Eds.): AE-CAI 2011, LNCS, pp. 36-46, 2012.
Gee A, et al., "Processing and visualizing three-dimensional ultrasound data.", The British Journal of Radiology, vol. 77, S186-S193, (2004).
George et al., "Low Cost Augmented Reality for Training of MRI-Guided Needle Biopsy of the Spine", Medicine Meets Virtual Reality 16, pp. 138-140, IOS Press, 2008.
Germano et al., Advanced Techniques in Image-Guided Brain and Spine Surgery, Thieme Medical Publishers, Incorporated, 2002.
Gonzalez, Smart Multi-Level Tool for Remote Patient Monitoring Based on a Wireless Sensor Network and Mobile Augmented Reality, Sensors, Sep. 2014; 14(9): 17212-17234.
Gorbert, M. et al., "Triangles: Tangible Interface for Manipulation and Exploration of Digital Information Topography.", Proceedings of CHI '98, Apr. 18-23, 1998, @ 1998 ACM.
Gromov et al., "What is the optimal alignment of the tibial and femoral components in knee arthroplasty?: An overview of the literature"; Acta Orthopaedica 2014; 85(5): 480-487.
Hayashibe et al., "Surgical Navigation Display System Using Volume Rendering of Intraoperatively Scanned CT Images", Computer Aided Surgery, vol. 11, No. 5, pp. 240-246, Sep. 2006.
Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.
Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.
Hinterstoisser, S.; Lepetit, V.; Benhimane, S.; Fua, P.; Navab, N. (2011a): Learning Real-Time Perspective Patch Rectification. In: International Journal of Computer Vision (IJCV), Springer. DOI: 10.1007/s11263-010-0379-x.
Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.
Hoff, "Fusion of Data from Head-Mounted and Fixed Sensors"; First International Workshop on Augmented Reality, 1, 1998, pp. 1-15.
Holographic weapon sight—Wikipedia https://en.wikipedia.org/wiki/Holographic_weapon_sight retrieved on Nov. 22, 2016.
Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Dec. 12, 2013.
Hua et al., "A 3D Integral Imaging Optical See-Through Head-Mounted Display", Optical Society of America, vol. 22, No. 11, pp. 1-8, Jun. 2, 2014.
Ishii, H., et al., "Iterative Design of Seamless Collaboration Media.", Communications of the ACM, vol. 37, No. 8, Aug. 1994, pp. 83-97.
Ji et al., "Real-Time Eye, Gaze, and Face Pose Tracking for Monitoring Driver Vigilance"; Real-Time Imaging 8, pp. 357-377, 2002.
Jiang et al., "A Robust Automated Markerless Registration Framework for Neurosurgery Navigation", The International Journal of Medical Robotics and Computer Assisted Surgery, vol. 11, pp. 436-447, Oct. 19, 2014.
Jolesz, Ferenc A., "Intraoperative Imaging and Image-Guided Therapy", Springer Science & Business Media, 893 pages, Jan. 14, 2014.
Kanade et al., "Simulation, Planning, and Execution of Computer-Assisted Surgery", Proceedings of the NSF Grand Challenges Workshop, 1996.
Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.
Kersten-Oertel et al., "The State of the Art of Visualization in Mixed Reality Image Guided Surgery", Computerized Medical Imaging and Graphics, vol. 37, pp. 98-112, Jan. 2013.
Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.
Kolodzey et al., "Wearable technology in the operating room: a systematic review"; GMJ Innov 2017; 3:55-63.
Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.
Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.
Lamata et al., "Augmented Reality for Minimally Invasive Surgery: Overview and Some Recent Advances"; Augmented Reality, Jan. 2010.
Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.

(56) References Cited

OTHER PUBLICATIONS

Liao et al., "Surgical Navigation by Autostereoscopic Image Overlay of Integral Videography", IEEE Transactions on Information Technology in Biomedicine, vol. 8, No. 2, pp. 114-121, Jun. 2004.
Lievin et al., "Stereoscopic Augmented Reality System for Computer-Assisted Surgery", International Congress Series, vol. 1230, pp. 107-111, Jun. 2001.
Lindert et al., "The use of a head-mounted display for visualization in neuroendoscopy", Computer Aided Surgery, 2004; 9(6): 251-256.
Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013; 37(2): 83-97, DOI: 10.1016/j.compmedimag.2012.12.002.
Liu et al., "An Optical See-Through Head Mounted Display with Addressable Focal Planes" IEEE International Symposium on Mixed and Augmented Reality, Cambridge, UK, pp. 33-42, Oct. 3, 2008.
Lorensen WE, Cline HE. [ed.], in M.C. Stone. 1987. Marching cubes: A high resolution 3d surface construction algorithm. Proceedings of SIGGRAPH 87. pp. 163-169.
Maier-Hein et al., "Optical Techniques for 3D Surface Reconstruction in Computer-Assisted Laparoscopic Surgery", Medical Image Analysis, vol. 17, pp. 974-996, May 3, 2013.
Maier-Hein, L. et al., "Towards Mobile Augmented Reality for On-Patient Visualization of Medical Images.", Bildverarbeitung für die Medizin 2011: Algorithmen—Systeme—Anwendungen Proceedings des Workshops vom Mar. 20-22, 2011 in Lübeck (pp. 389-393).
Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.
Maurer et al., "Augmented-Reality Visualization of Brain Structures with Stereo and Kinetic Depth Cues: System Description and Initial Evaluation with Head Phantom", Proceedings, vol. 4319, Medical Imaging 2001: Visualization, Display, and Image-Guided Procedures, pp. 445-456, May 28, 2001.
Medeiros D. et al., "Proposal and evaluation of a tablet-based tool for 3D virtual environments.", SBC Journal on 3D Interactive Systems, vol. 4, No. 2, pp. 30-40, (2013).
Melzer, "Head-Mounted Displays", The Avionics Handbook, 2001.
Menozzi et al., "Development of Vision-Aided Navigation for a Wearable Outdoor Augmented Reality System", IEEE Plans, Position Location and Navigation Symposium, Article No. 6851442, pp. 760-772, 2014.
Micro Vision 2015 Annual Report and Proxy Statement for 2016 Annual Meeting of Shareholders.
Moore et al., "Image Guidance for Spinal Facet Injections Using Tracked Ultrasound", MICCAI 2009, Part I, Lncs 5761, pp. 516-523 2009.
Muller et al., "Automatic Multi-Modal ToF/CT Organ Surface Registration", Bildverarbeitung für die Medizin, pp. 154-158, Mar. 2011.
Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.
Nicolau, "Augmented Reality in Laparoscopic Surgical Oncology.", Surgical Oncology, vol. 20, pp. 89-201 (2011).
Nikou et al., "Augmented Reality Imaging Technology for Orthopaedic Surgery", Operative Techniques in Orthopaedics, vol. 10, No. 1 Jan. 2000: pp. 82-86.
Noonan et al., "The Design and Initial Calibration of an Optical Tracking System Using the Microsoft Kinect", IEEE Nuclear Science Symposium Conference Record, pp. 3614-3617, Oct. 2011.
Okamura, Allison, "Tracking and Surgical Navigation, Registration", Stanford Lecture 8: ME 328: Medical Robotics, pp. 1-19, Spring 2013.

Ortega et al., "Usefulness of a head mounted monitor device for viewing intraoperative fluoroscopy during orthopaedic procedures", Arch Orthop Trauma Surg (2008) 128:1123-1126.
Paprosky et al., "Intellijoint HIP: a 3D mini-optical navigation tool for improving intraoperative accuracy during total hip arthroplasty"; Med Devices (Auckl). 2016; 9: 401-408.
Pauly et al., "Machine Learning-Based Augmented Reality for Improved Surgical Scene Understanding", Computerized Medical Imaging and Graphics, vol. 1280, pp. 1-6, Jun. 2014.
Peters et al., "Image-Guided Interventions, Technology and Applications", Springer Science and Business Media, 576 pages, 2018.
Ponce et al., "Emerging Technology in Surgical Education: Combining Real-Time Augmented Reality and Wearable Computing Devices", The Cutting Edge, Nov. 2014, vol. 37, No. 11.
Qian, Long; Azimi, Ehsan; Kazanzides, Peter; Navab, Nassir (2017): Comprehensive Tracker Based Display Calibration for Holographic Optical See-Through Head-Mounted Display.
Ren et al., "Marker-Based Surgical Instrument Tracking Using Dual Kinect Sensors", IEEE Transactions on Automation Science and Engineering, vol. 11, No. 3, pp. 921-924, Jul. 2014.
Rhodes, "A brief history of wearable computing", MIT Wearable Computing Project.
Rinaldi et al., "Computer-Guided Applications for Dental Implants, Bone Grafting, and Reconstructive Surgery", Elsevier Inc., 556 pages, 2016.
Robinett et al., "A Computational Model for the Stereoscopic Optics of a Head-Mounted Display", Proceedings vol. 1457, Stereoscopic Displays and Applications II, pp. 140-160, 1991.
Rolland et al., "A Comparison of Optical and Video See-through Head-mounted Displays", Proceedings vol. 2351, Telemanipulator and Telepresence Technologies, pp. 293-307, Dec. 21, 1995.
Rolland et al., "Optical Versus Video See-Through Head-Mounted Displays in Medical Visualization", Presence: Teleoperators and Virtual Environments, vol. 9, Issue 3, pp. 287-309, Jun. 2000.
Rosenthal et al., "Augmented Reality Guidance for Needle Biopsies: A Randomized, Controlled Trial in Phantoms"; MICCAI 2001, LNCS 2208: 240-248.
Rosman et al., "Articulated Motion Segmentation of Point Clouds by Group-Valued Regularization", Eurographics Workshop on 3D Object Retrieval, EG 3DOR, pp. 77-84, May 2012.
Salmi Jamali, S. et al., "Utilising Mobile-Augmented Reality for Learning Human Anatomy.", 7th World Conference on Educational Sciences, (WCES-2015), Feb. 5-7, 2015, Novotel Athens Convention Center, Athens, Greece.
Sanko, "Microvision's Nomad Augmented Vision System: The How and the Why"; SID Pacific Northwest Chapter Meeting, Jun. 11, 2003.
Sauer et al., "An Augmented Reality Navigation System with a Single-Camera Tracker: System Design and Needle Biopsy Phantom Trial", Proceedings of the 5th International Conference on Medical Image Computing and Computer-Assisted Intervention—Part II, pp. 116-124, Sep. 2002.
Sauer et al., "Augmented Workspace: Designing an AR Testbed", Proceedings IEEE and ACM International Symposium on Augmented Reality, pp. 47-53, Munich 2000.
Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2x1LmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1Iz_TUFgILvsRhShqXDrSM63OcvvjlSzpUoBvsC2LsOmHqf-zifqdYelctf0D0MDM78YhH-u7w9JUfxuLDGVUxUi9hDQLZo.
Scuderi et al., "Total Knee Arthroplasty with a Novel Navigation System Within the Surgical Field", Orthopedic Clinics, vol. 45, Issue 2, pp. 167-173, Apr. 2014.
Shen et al., "3D Augmented Reality with Integral Imaging Display", Proceedings of SPIE—The International Society for Optical Engineering, vol. 9867, Article No. 9867OY, Apr. 2016.
Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.

(56) References Cited

OTHER PUBLICATIONS

State et al., "Stereo Imagery from the UNC Augmented Reality System for Breast Biopsy Guidance", MMVR 2003.
Tan, D. J.; Tombari, F..; Ilic, S.; Navab, N. (2015): A Versatile Learning-Based 3D Temporal Tracker. Scalable, Robust, Online. In: 2015 IEEE International Conference on Computer Vision (ICCV), S. 693-701.
Technische Universitat Munchen, A Look into the Body-Augmented Reality in Computer Aided Surgery, Department of Informatics, Research-Highlights.
Tong et al., "Scanning 3D Full Human Bodies Using Kinects", IEEE Transactions on Visualization and Computer Graphics, vol. 18, Issue 4, pp. 643-650, Apr. 1, 2012.
Traub, J., Stefan, P., Heining, S.M., Sielhorst, T., Riquarts, C., Eulerz, E., Navab, N. (2006): Hybrid Navigation Interface for Orthopedic and Trauma Surgery. R. Larsen, M. Nielsen, and J. Sporring (Eds.): MICCAI 2006, LNCS 4190, pp. 373-380.
Trevisan et al., "Towards Markerless Augmented Medical Visualization", AMI-ARCS, pp. 57-66, 2004.
Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.
Vercauteren et al., "Real Time Autonomous Video Image Registration for Endomicroscopy: Fighting the Compromises", Three-Dimensional and Multidimensional Microscopy: Image Acquisition and Processing XV., vol. 6861, pp. 68610C. International Society for Optics and Photonics, Feb. 12, 2008.
Vogt et al., "Reality Augmentation for Medical Procedures: System Architecture, Single Camera Marker Tracking, and System Evaluation", International Journal of Computer Vision, vol. 70, No. 2, pp. 179-190, 2006.
Vogt, Sebastian, "Real-Time Augmented Reality for Image-Guided Interventions", PhD Thesis, Nürnberg: Der Technischen Fakultät der Universität Erlangen, 2009.
Wang et al., "3D Modeling from Wide Baseline Range Scans Using Contour Coherence", Proceedings of the IEEE Conference on Computer Vision and Pattern Recognition, pp. 4018-4025, 2014.
Wang et al., "Augmented Reality 3D Displays with Micro Integral Imaging"; Journal of Display Technology, Oct. 2014.
Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.
Wang H. et al., "Precision insertion of percutaneous sacroiliac screws using a novel augmented reality-based navigation system: a pilot study"., Intl. Orthop. (SICOT) 2016, 40: 1941-1947.
Watsen, K., et al., "A Handheld Computer as an Interaction Device to a Virtual Environment.", Proceedings of the International Projection Technologies Workshop, Stuttgart, Germany, May 10-11, 1999.
Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.
Wellner, P., "Interacting with Paper on the DigitalDesk.", Communications of the ACM. 36, 7, 87-96, (1993).
Wilson et al., "Validation of Three-Dimensional Models of the Distal Femur Created from Surgical Navigation Point Cloud Data"; CAOS 2015.
Xiaojun et al., "Development of a Surgical Navigation System Based on Augmented Reality Using an Optical See-Through Head-Mounted Display", Journal of Biomedical Informatics, vol. 55, pp. 124-131, 2015.
Yamazaki, K. et al., "Gesture Laser and Gesture Laser Car-Development of an Embodied Space to Support Remote Instruction. ", In Bodker, S., Kyng, M. and Schmidt, K. (eds.), Proceedings of the Sixth European Conference on Computer Supported Cooperative Work—ECSC W, Sep. 12-16, 1999, Copenhagen, Denmark. Kluwer Academic Publishers, Dordrecht.
Yang H. et al., "Exploring collaborative navigation.", Proceedings of the 4th international conference on Collaborative virtual environments, CVE, pp. 135-142, (2002).
Ye et al., "Accurate 3D Pose Estimation from a Single Depth Image", IEEE International Conference on Computer Vision (ICCV), pp. 731-738, Nov. 2011.
Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.

* cited by examiner

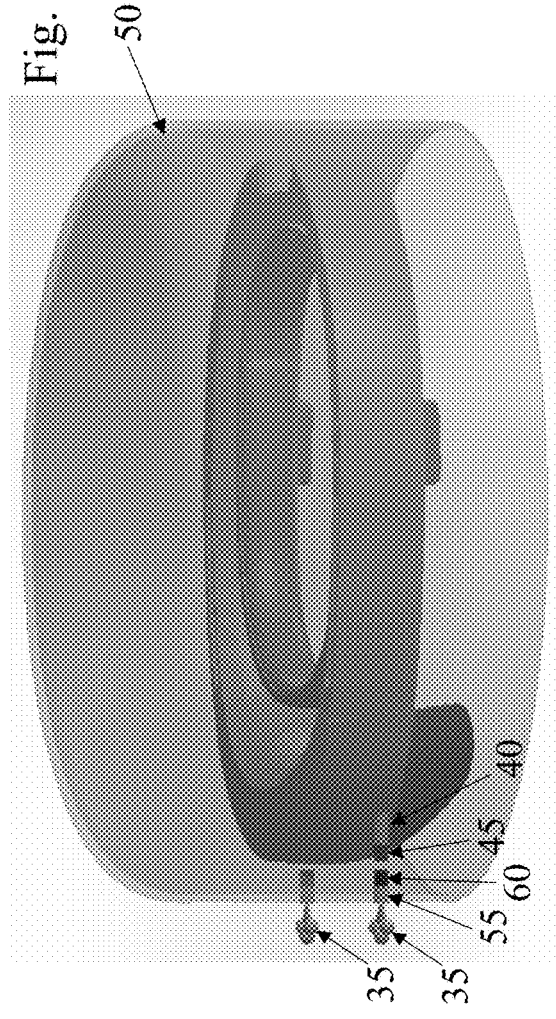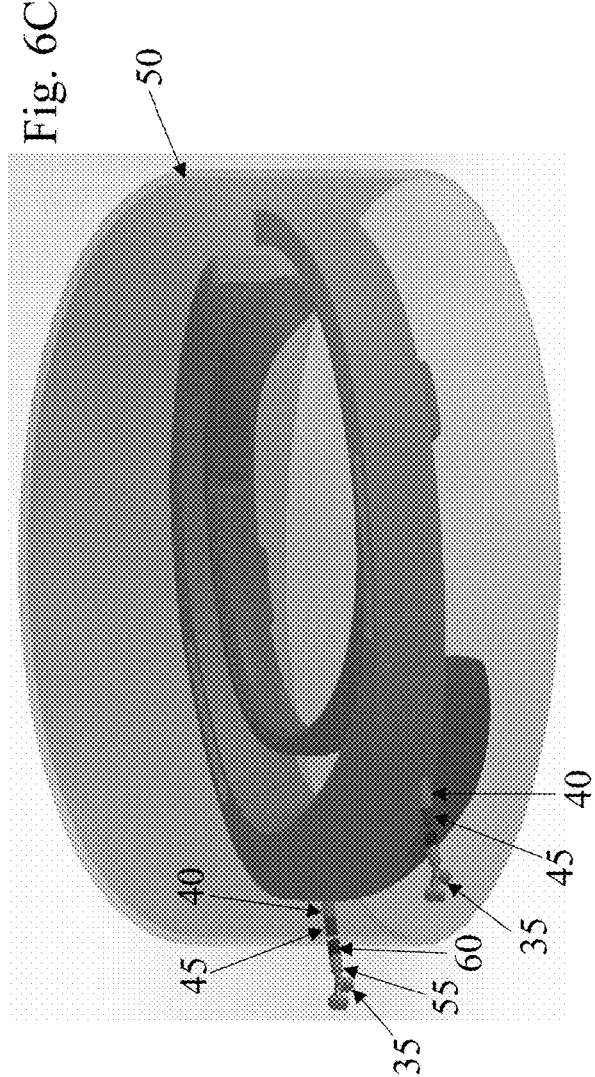

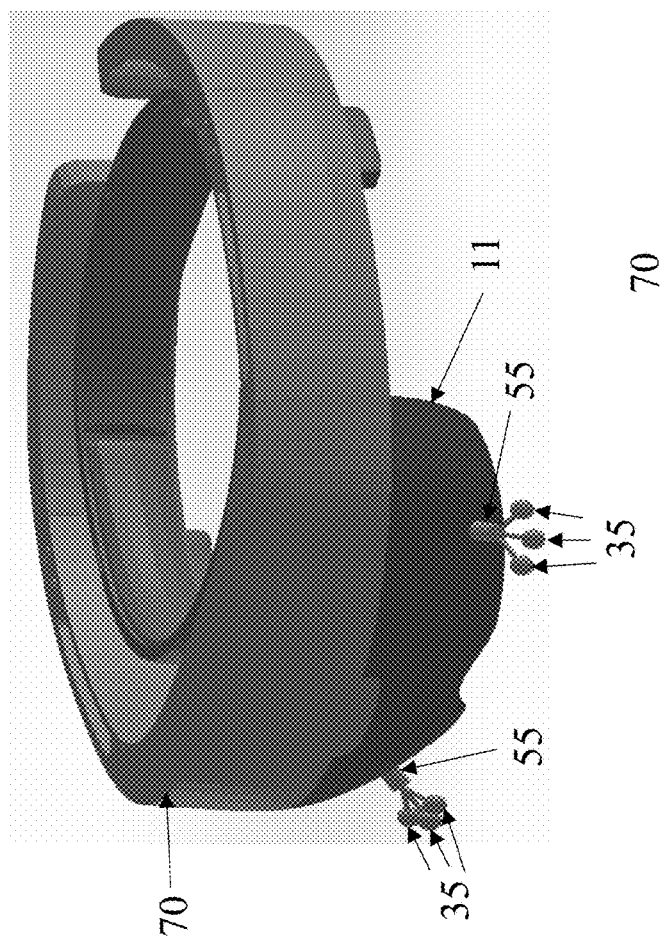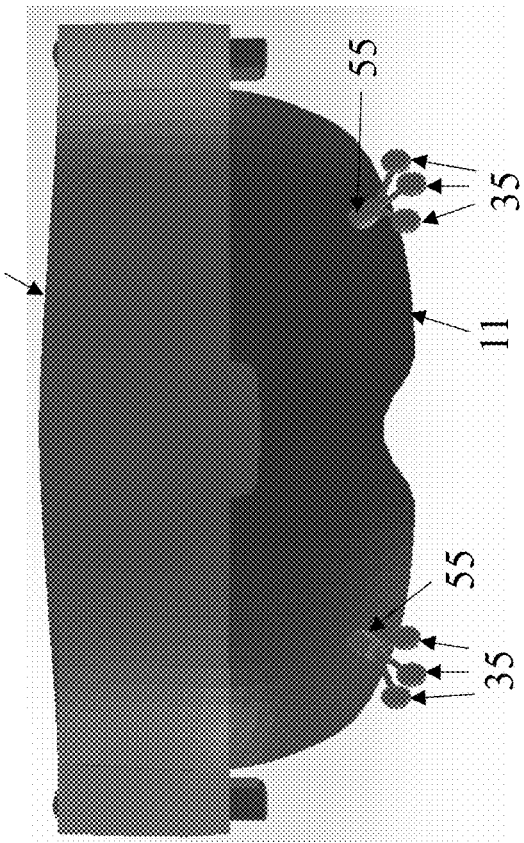

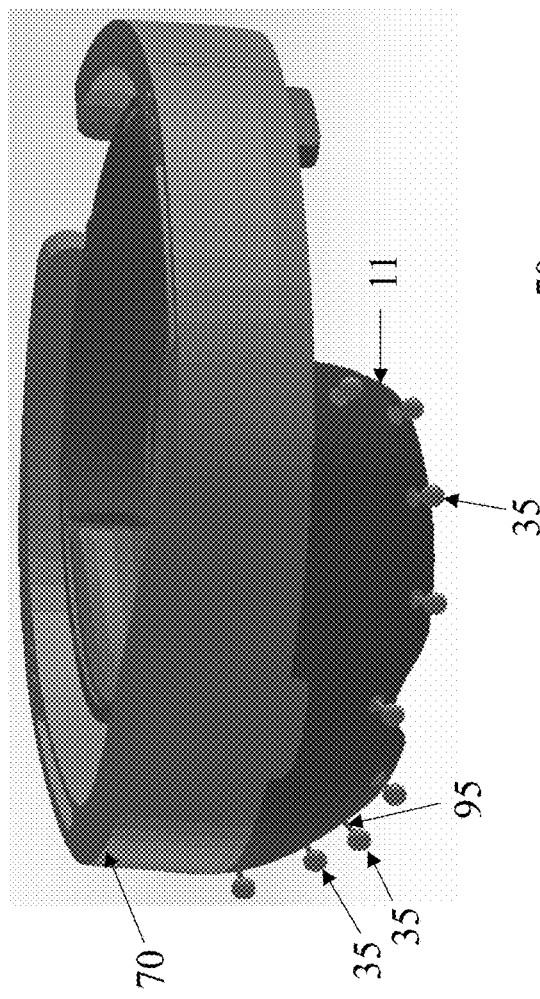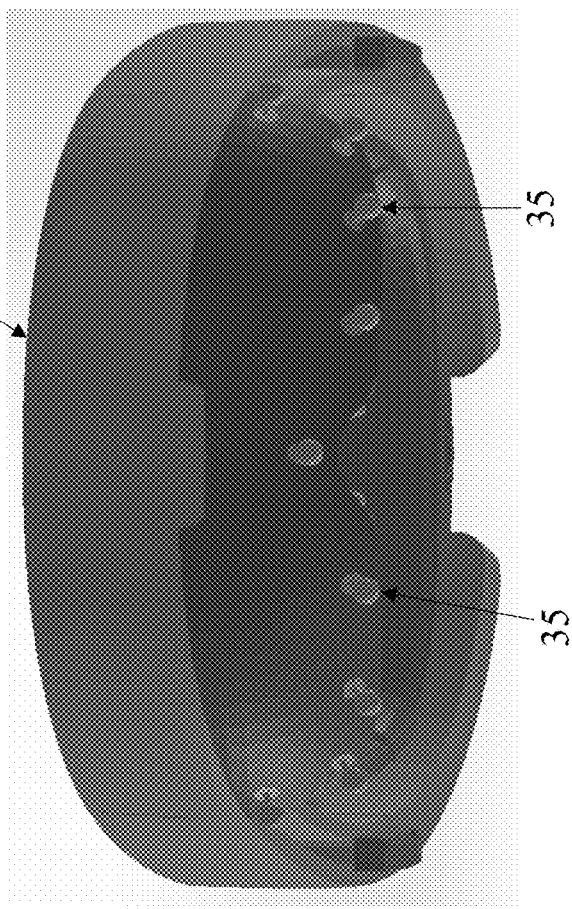

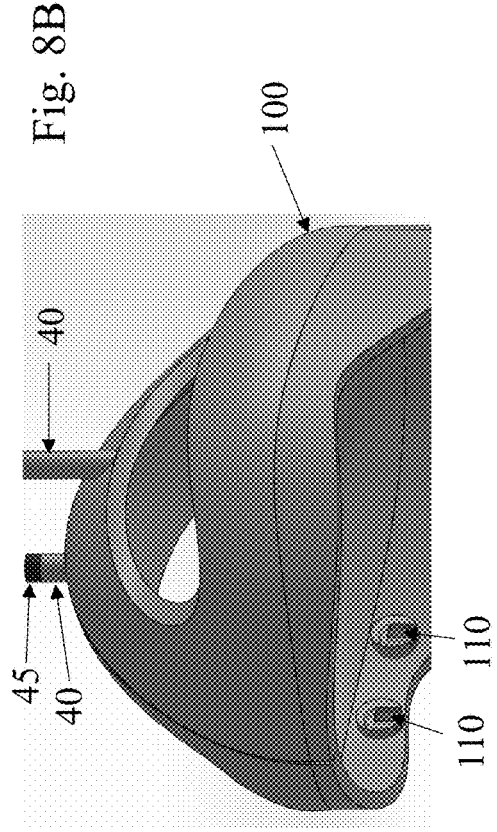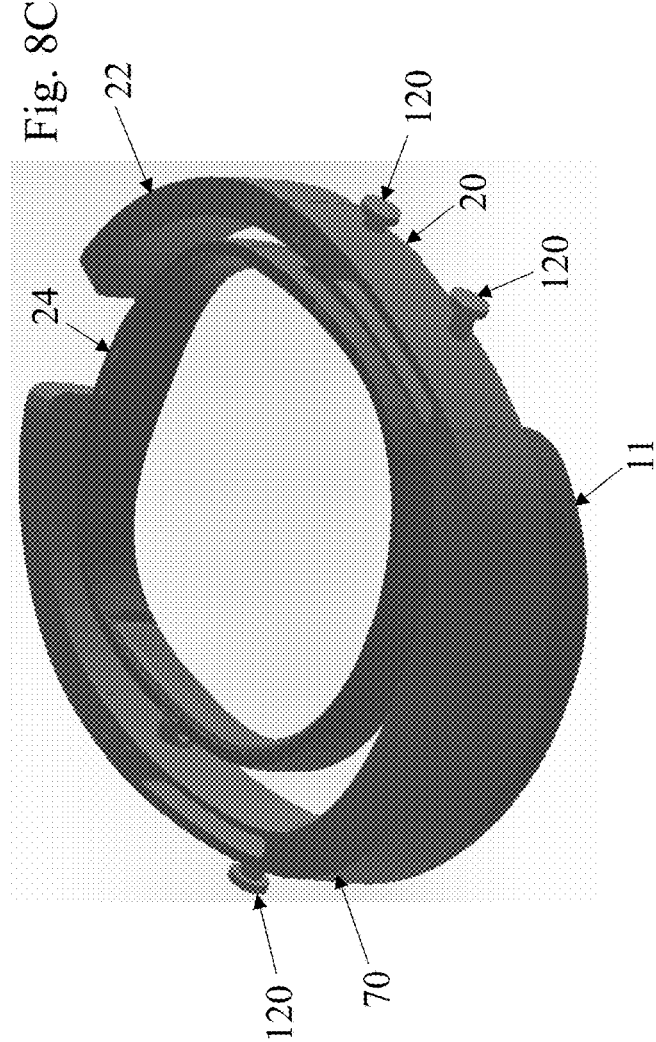

SYSTEMS FOR ADJUSTING AND TRACKING HEAD MOUNTED DISPLAYS DURING SURGERY INCLUDING WITH SURGICAL HELMETS

RELATED APPLICATIONS

This application claims the benefit of and the priority to U.S. Provisional Application Ser. No. 62/805,824, filed Feb. 14, 2019, and U.S. Provisional Application Ser. No. 62/817,595, filed Mar. 13, 2019, the entire contents of each of which is hereby incorporated by reference in their entireties.

TECHNICAL FIELD

Aspects of the present disclosure relate to systems, devices and methods for performing a surgical step or surgical procedure with visual guidance using a head mounted display. Aspects of the present disclosure relate a protective cover for the surgical helmet or hood, a protective face shield, and/or a helmet for use during a surgical step or surgical procedure.

BACKGROUND

With computer assisted surgery, e.g. surgical navigation or robotics, pre-operative imaging studies of the patient can be used. The imaging studies can be displayed in the OR on an external computer monitor and the patient's anatomy, e.g. landmarks, can be registered in relationship to the information displayed on the monitor. Since the surgical field is in a different location and has a different view coordinate system for the surgeon's eyes than the external computer monitor, hand-eye coordination can be challenging for the surgeon.

SUMMARY

Aspects of the disclosure relate to a system comprising a head mounted display, an adjusting mechanism, and a connecting mechanism, wherein the head mounted display is configured to be worn on a head of a user under a cover of a surgical helmet so that the display of the head mounted display is adjacent to a transparent portion of the cover, wherein the adjusting mechanism is configured to adjust at least a position of the head mounted display in relationship to the user's eyes, and wherein the connecting mechanism is configured to couple the head mounted display to the surgical helmet. In some embodiments, the adjusting mechanism comprises the connecting mechanism. In some embodiments, the connecting mechanism is configured to be attachable to the surgical helmet. In some embodiments, the connecting mechanism is configured to be integrated into the surgical helmet. In some embodiments, the connecting mechanism is configured to be attachable to the head mounted display. In some embodiments, the connecting mechanism is configured to be integrated into the head mounted display. In some embodiments, the connecting mechanism is configured to be integrated into a portion of a housing of the head mounted display. In some embodiments, the connecting mechanism is configured to attach the head mounted display to the surgical helmet.

In some embodiments, the adjusting mechanism is configured to adjust the head mounted display in relationship to the user's eyes in an x, a y, or a z-direction or combinations thereof. In some embodiments, the adjustment of the head mounted display comprises a translation of about 30 mm, about 25 mm, about 20 mm, about 15 mm, about 10 mm, about 7 mm, about 5 mm, about 4 mm, about 3 mm, about 2 mm, about 1 mm, about 0.5 mm, about 0.25 mm in at least one of an x, a y, or a z-direction or combinations thereof. In some embodiments, the adjusting mechanism is configured to rotate, tilt or rotate and tilt the head mounted display in relationship to at least one of the user's eyes. In some embodiments, the rotating or tilting or rotating and tilting the head mounted display comprises a change in angular orientation of about 30°, about 25°, about 20°, about 15°, about 10°, about 9°, about 8°, about 7°, about 6°, about 5°, about 4°, about 3°, about 2°, about 1°, about 0.5°, about 0.25° in at least one direction. In some embodiments, the adjusting mechanism is configured for adjusting the position of the head mounted display prior to a surgical procedure or during the surgical procedure or prior to and during the surgical procedure. In some embodiments, the surgical procedure comprises a knee replacement, hip replacement, shoulder joint replacement, ankle joint replacement, or a spinal procedure.

In some embodiments, the adjusting mechanism comprises a mechanical mechanism configured to adjust the position of the head mounted display. In some embodiments, the mechanical mechanism comprises one or more mechanical elements, wherein the one or more mechanical element comprises a dial, knob, button, lever, slider, handle, handle bar, ring, key, wrench or combinations thereof. In some embodiments, the mechanical mechanism comprises one or more mechanical elements configured to be subjacent to the cover for the surgical helmet, and wherein the mechanical element is configured to be operated through the cover for the surgical helmet. In some embodiments, the mechanical mechanism comprises one or more mechanical elements configured to be operated external to the cover for the surgical helmet. In some embodiments, the mechanical element external to the cover for the surgical helmet is provided sterile. In some embodiments, the adjusting mechanism comprises a motorized element, an electric element, an electromagnetic element, a piezoelectric element or combinations thereof configured to adjust the position of the head mounted display.

In some embodiments, the processor and a user interface, wherein the user interface is configured to control the motorized element, the electric element, the electromagnetic element, the piezoelectric element or combinations thereof, wherein the user interface comprises a graphical user interface, a voice recognition, a gesture recognition, a virtual interface displayed by the head mounted display, a virtual keyboard displayed by the head mounted display, a virtual slider, a virtual button, an eye tracking system, a physical keyboard, a physical computer mouse, a physical button, a physical joy stick, a physical track pad, or a combination thereof. In some embodiments, the system further comprises a processor and an eye tracking system, wherein the processor is configured to receive one or more inputs from the eye tracking system and to generate one or more outputs for activating the motorized element, the electric element, the electromagnetic element, the piezoelectric element or combinations thereof for adjusting the position of the head mounted display. In some embodiments, the eye tracking system comprises at least one camera configured to be integrated into or attached to the head mounted display or the surgical helmet, wherein the at least one camera is configured to track at least one eye of the user.

In some embodiments, the head mounted display is an optical see through head mounted display. In some embodiments, the head mounted display is a video see through head mounted display.

Aspects of the disclosure relate to a system comprising a head mounted display, at least one holding member, at least one marker, and at least one magnetic coupling mechanism, wherein the at least one holding member is configured to be integrated into or configured to be attached to the head mounted display, and wherein the at least one magnetic coupling mechanism is configured to removably attach the at least one marker to the at least one holding member. In some embodiments, the head mounted display is configured to be worn under a cover of a surgical helmet by a user. In some embodiments, the system is configured to track the head mounted display during a surgical procedure. In some embodiments, the system comprises a processor.

In some embodiments, the at least one holding member is attached directly to the head mounted display. In some embodiments, the at least one holding member is attached indirectly to the head mounted display. In some embodiments, each of the at least one holding member comprises a proximal and a distal end, wherein the proximal end of the holding member is attached to the head mounted display, and wherein the at least one marker is attached to the distal end of the holding member. In some embodiments, the at least one holding member is attached directly to the head mounted display. In some embodiments, the at least one holding member is attached indirectly to the head mounted display.

In some embodiments, the at least one magnetic coupling mechanism comprises at least one magnetic element, and wherein the at least one magnetic element is positioned at the distal end of the at least one holding member. In some embodiments, the at least one magnetic element is attached to the distal end of the at least one holding member, to the at least one marker or to the distal end of the at least one holding member and to the at least one marker. In some embodiments, the at least one magnetic coupling mechanism comprises a first magnetic element attached to the distal end of the at least one holding member and a second magnetic element attached to the to the at least one marker.

In some embodiments, the at least one holding member is configured to be removably attached to the head mounted display. The holding member can be composed of at least one of a metal, plastic, magnetic material, or combinations thereof. In some embodiments, the holding member is rigid.

In some embodiments, the holding member is configured to extend subjacent to a cover for a surgical helmet, and wherein the at least one marker is configured to be attached to the at least one holding member superjacent to the cover for the surgical helmet.

In some embodiments, the system further comprises a processor, wherein the processor is configured to register the head mounted display in a coordinate system using the at least one marker. In some embodiments, the processor is integrated into the head mounted display. In some embodiments, the processor is external to the head mounted display.

the at least one marker is part of a marker structure, wherein the marker structure comprises two or more markers, wherein the two or more markers are arranged in a geometrically predetermined orientation.

In some embodiments, the at least one magnetic coupling mechanism is configured to position the at least one marker in a geometrically predetermined position and orientation relative to the head mounted display. In some embodiments, the at least one marker is configured to be mounted in a geometrically predetermined position and orientation with an accuracy of about 2 mm, about 1.5 mm, about 1 mm, about 0.5 mm, about 0.25 mm, about 0.1 mm, about 0.05 mm in at least one direction, or an accuracy of about 2°, about 1.5°, about 1°, about 0.5°, about 0.25°, about 0.1°, about 0.05° in at least one direction. In some embodiments, the at least one magnetic coupling mechanism comprises one or more neodymium magnets. In some embodiments, the at least one marker, the at least one holding member, the at least one magnetic coupling mechanism, or combinations thereof comprise one or more mating features, wherein the one or more mating features are configured to position the at least one marker in a geometrically predetermined position and orientation relative to the head mounted display. The predetermined position and orientation can be adjusted for a thickness of the cover for the surgical helmet. In some embodiments, the least one marker comprises at least one of an optical marker, a geometric pattern, a bar code, a QR code, an alphanumeric code, a radiofrequency marker, an infrared marker, a retroreflective marker, an active marker, and a passive marker.

In some embodiments, the at least a portion of the holding member is provided sterile. In some embodiments, the at least one marker is provided sterile.

In some embodiments, the at least one holding member is configured to be integrated into, attached to or linked to the surgical helmet. In some embodiments, the at least one holding member is configured to be removably connected to the head mounted display using at least one magnetic mechanism, a mechanical attachment mechanism, an electromagnetic attachment mechanism, or combinations thereof. In some embodiments, the at least one holding member is configured to be removably connected to the surgical helmet using at least one of a magnetic mechanism, a mechanical attachment mechanism, an electromagnetic attachment mechanism, or combinations thereof.

In some embodiments, the at least one marker comprises a base, wherein the base is mounted on the distal end of the at least one holding member using the at least one magnetic element. In some embodiments, the at least one magnetic element is configured to be integrated into or attached to the at least one of the at least one marker, the base holding the at least one marker, the at least one holding member, the head mounted display, the surgical helmet, the cover for the surgical helmet or combinations thereof.

In some embodiments, the head mounted display is an optical see through head mounted display. In some embodiments, the head mounted display is a video see through head mounted display.

Some aspects of the present disclosure relate to a system for tracking a head mounted display during a surgical procedure, the system comprising a head mounted display, at least one marker, and at least one holding member, wherein the head mounted display is configured to be integrated into or attached to a surgical helmet, wherein the at least one holding member is integrated into or configured to be attached to or connected to the head mounted display, the surgical helmet or combinations thereof, wherein at least a portion of the at least one holding member is configured to extend through at least one opening of a cover for the surgical helmet, and wherein the at least one marker is configured to be integrated into or attached to the at least one holding member external to the cover.

In some embodiments, the system further comprises a processor configured to register the head mounted display in a coordinate system using the at least one marker. In some embodiments, the processor is integrated into the head mounted display. In some embodiments, the processor is external to the head mounted display.

In some embodiments, the system is configured to track the head mounted display during a surgical procedure.

In some embodiments, the head mounted display is configured to be integrated into or attached to the surgical helmet worn on a head of a user under the cover so that the display of the head mounted display is adjacent to a transparent portion of the cover so as to permit the user to view the surgical site.

In some embodiments, wherein the at least a portion of the holding member is provided sterile.

In some embodiments, the at least the portion of the holding member that extends external of the cover for the surgical helmet is provided sterile. In some embodiments, the at least one marker is provided sterile.

In some embodiments, the at least one holding member is configured to be integrated into, attached to or connected to the surgical helmet.

In some embodiments, the least one marker comprises one or more optical marker, a geometric pattern, a bar code, a QR code, an alphanumeric code, a radiofrequency marker, an infrared marker, a retroreflective marker, an active marker, a passive marker, or combinations thereof.

In some embodiments, the at least one marker is configured to be removably attached to the at least one holding member using a magnetic mechanism, a mechanical attachment mechanism, an electromagnetic attachment mechanism, or combinations thereof.

In some embodiments, the at least one holding member is configured to be removably attached to the head mounted display using a magnetic mechanism, a mechanical attachment mechanism, an electromagnetic attachment mechanism, or combinations thereof. In some embodiments, the at least one holding member is configured to be attached to the surgical helmet using a magnetic mechanism, a mechanical attachment mechanism, an electromagnetic attachment mechanism, or combinations thereof.

In some embodiments, the at least one marker comprises a base, wherein the base is mounted on the at least one holding member.

In some embodiments, the head mounted display is an optical see through head mounted display. In some embodiments, the head mounted display is a video see through head mounted display.

BRIEF DESCRIPTION OF THE DRAWINGS

Illustrative, non-limiting example embodiments will be more clearly understood from the following detailed description taken in conjunction with the accompanying drawings.

FIGS. 6A-6D are illustrative examples of an HMD with holding members attached to the front of the HMD with magnetic end portions and/or mechanical connectors according to some embodiments.

FIGS. 7A-7D are illustrative examples of an HMD with holding arms or bases or fiducial markers attached to a front portion of a visor of the HMD according to some embodiments.

FIGS. 8A-8E are illustrative examples of an integration of an HMD with a surgical helmet according to some embodiments.

DETAILED DESCRIPTION

Figure 1:
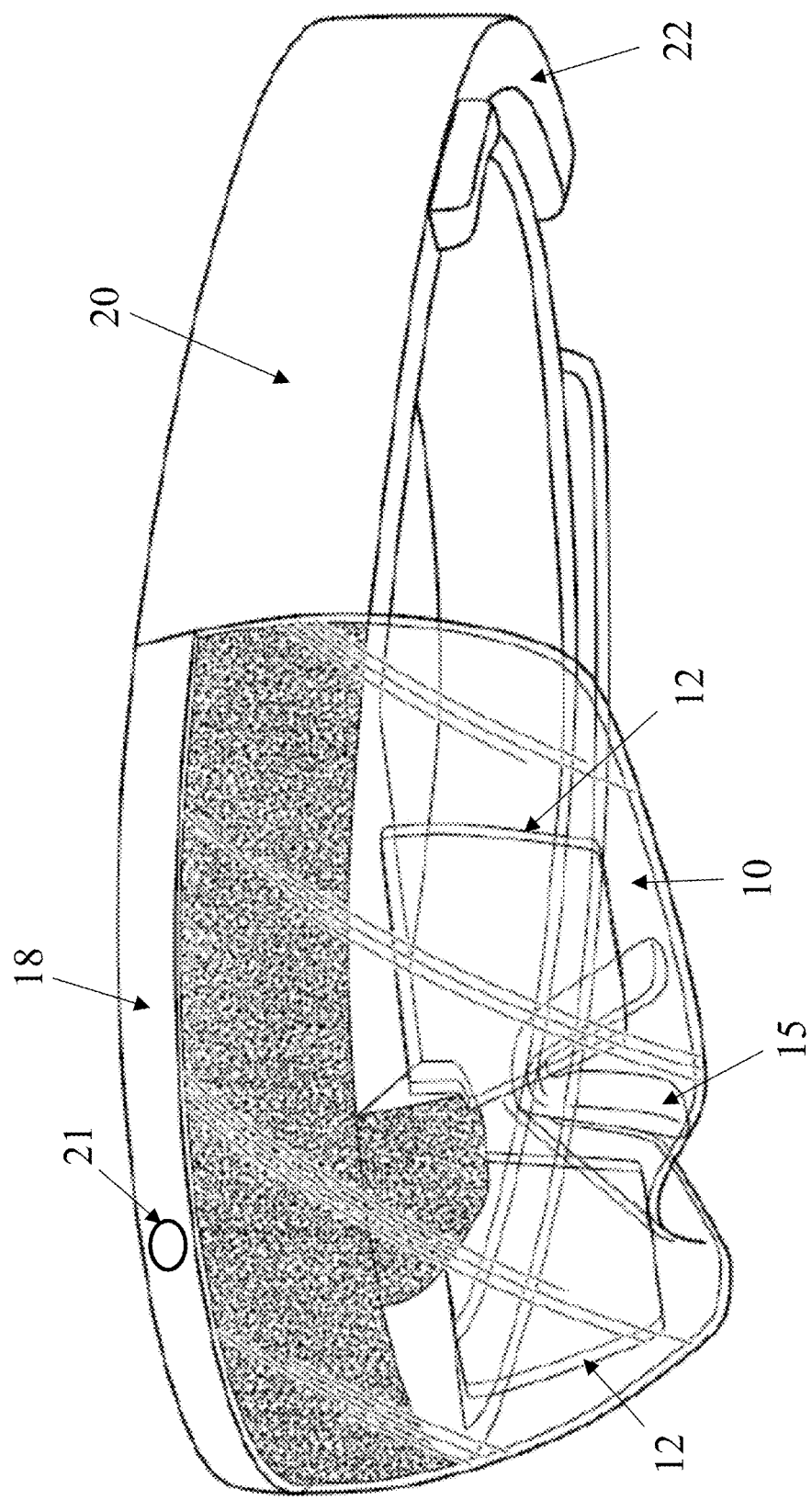
FIG. 1 is an exemplary, non-limiting illustration showing a head mounted display, in this case an optical see through head mounted display or see through optical head mounted display according to some embodiments.

Aspects of the disclosure relate to systems and methods to register and/or track a head mounted display (HMD) in a coordinate system using, for example, a surgical navigation system, an image capture system, a video capture system, one or more depth sensors, one or more inertial moment units (IMUs), or any other registration and/or tracking system known in the art and described, for example in PCT application PCT/US19/15522 filed, on Jan. 29, 2019, the entire contents of each of which is hereby incorporated by reference in its entirety.

One or more fiducial markers, e.g. optical markers, e.g. QR codes or Aruco markers (Intel, Inc.), navigation markers, including infrared markers, RF markers, active markers (e.g. LEDs, including LEDs emitting infrared light or light from the spectrum visible to the human eye), passive markers (for example as described in PCT application PCT/US19/15522, the entire contents of each of which is hereby incorporated by reference in its entirety) can be used and can be directly or indirectly integrated into, attached to, connected to, or mounted onto a head mounted display. Optionally, the surgeon can wear a surgical helmet, for example, with a protective cover and clear see-through shield. Representative examples are, for example, the Stryker T5 surgical helmet and associated sterile cover for the surgical helmet or hoods or the Stryker Flyte helmet and associated cover for the surgical helmet or hoods.

Aspects of the present disclosure relate to systems, devices and methods for performing a surgical step or surgical procedure with visual guidance using a head mounted display, e.g. by displaying virtual representations of one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, on a live patient. In some embodiments, the head mounted (HMD) is a see-through head mounted display. In some embodiments, an optical see through HMD is used. In some embodiments, a video see through HMD can be used, for example with a camera integrated into, attached to, or separate from the HMD, generating video feed.

Aspects of the disclosure can be applied to knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. In some embodiments, one or more head mounted displays can display virtual data, e.g. virtual surgical guides, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery.

In some embodiments, one or more head mounted displays can be used to display volume data or surface data, e.g. of a patient, of imaging studies, of graphical representation and/or CAD files. Aspects of the disclosure relate to a system or device comprising at least one head mounted display, the device being configured to generate a virtual surgical guide. In some embodiments, the virtual surgical guide is a three-dimensional representation in digital format which corresponds to at least one of a portion of a physical surgical guide, a placement indicator of a physical surgical guide, or a combination thereof. In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw blade with the virtual surgical guide to guide a bone cut of the joint.

In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw drill, pin, burr, mill, reamer, broach, or impactor with the virtual surgical guide to guide a drilling, pinning, burring, milling, reaming, broach or impacting of the joint.

In some embodiments, the at least one head mounted display is configured to display the virtual surgical guide superimposed onto a physical spine based at least in part on coordinates of a predetermined position of the virtual surgical guide, and the virtual surgical guide is configured to align the physical surgical guide or a physical tool or physical instrument with the virtual surgical guide to guide an awl, a drill, a pin, a tap, a screw driver or other instrument or tool. In some embodiments, the system or device comprises one, two, three or more head mounted displays.

In some embodiments, the virtual surgical guide is configured to guide a bone cut in a knee replacement, hip replacement, shoulder joint replacement or ankle joint replacement. In some embodiments, the virtual surgical guide includes a virtual slot for a virtual or a physical saw blade. In some embodiments, the virtual surgical guide includes a planar area for aligning a virtual or a physical saw blade. In some embodiments, the virtual surgical guide includes two or more virtual guide holes or paths for aligning two or more physical drills or pins.

In some embodiments, the predetermined position of the virtual surgical guide includes anatomical information, and/or alignment information of the joint. For example, the anatomic and/or alignment information of the joint can be based on at least one of coordinates of the joint, an anatomical axis of the joint, a biomechanical axis of the joint, a mechanical axis, or combinations thereof.

In some embodiments, the at least one head mounted display is configured to align the virtual surgical guide based on a predetermined limb alignment. For example, the predetermined limb alignment can be a normal mechanical axis alignment of a leg.

In some embodiments, the at least one head mounted display is configured to align the virtual surgical guide based on a predetermined femoral or tibial component rotation. In some embodiments, the at least one head mounted display is configured to align the virtual surgical guide based on a predetermined flexion of a femoral component or a predetermined slope of a tibial component.

In some embodiments, the virtual surgical guide is configured to guide a proximal femoral bone cut based on a predetermined leg length. In some embodiments, the virtual surgical guide is configured to guide a bone cut of a distal tibia or a talus in an ankle joint replacement and the at least one head mounted display is configured to align the virtual surgical guide based on a predetermined ankle alignment, wherein the predetermined ankle alignment includes a coronal plane implant component alignment, a sagittal plane implant component alignment, an axial plane component alignment, an implant component rotation or combinations thereof.

In some embodiments, the virtual surgical guide is configured to guide a bone cut of a proximal humerus in a shoulder joint replacement and the at least one head mounted display is configured to align the virtual surgical guide based on a predetermined humeral implant component alignment, wherein the humeral implant component alignment includes a coronal plane implant component alignment, a sagittal plane implant component alignment, an axial plane component alignment, an implant component, or combinations thereof.

In some embodiments, the predetermined position of the surgical guide is based on a pre-operative or intra-operative imaging study, one or more intra-operative measurements, intra-operative data or combinations thereof.

Aspects of the disclosure relate to a system or device comprising two or more head mounted displays for two or more users, wherein the device is configured to generate a virtual surgical guide, wherein the virtual surgical guide is a three-dimensional representation in digital format which corresponds to at least one of a portion of a physical surgical guide, a placement indicator of a physical surgical guide, or a combination thereof, wherein the head mounted display is configured to display the virtual surgical guide superimposed onto a physical joint based at least in part on coordinates of a predetermined position of the virtual surgical guide, and wherein the virtual surgical guide is configured for aligning the physical surgical guide or a saw blade to guide a bone cut of the joint.

Aspects of the disclosure relate to a system or device comprising at least one head mounted display and a virtual bone cut plane, wherein the virtual bone cut plane is configured to guide a bone cut of a joint, wherein the virtual bone cut plane corresponds to at least one portion of a bone cut plane, and wherein the head mounted display is configured to display the virtual bone cut plane superimposed onto a physical joint based at least in part on coordinates of a predetermined position of the virtual bone cut plane. In some embodiments, the virtual bone cut plane is configured to guide a bone cut in a predetermined *varus* or valgus orientation or in a predetermined tibial slope or in a predetermined femoral flexion of an implant component or in a predetermined leg length.

Aspects of the disclosure relate to a method of preparing a joint for a prosthesis in a patient. In some embodiments, the method comprises registering one or more head mounted displays worn by a surgeon or surgical assistant in a coordinate system, obtaining one or more intra-operative measurements from the patient's physical joint to determine one or more intra-operative coordinates, registering the one or more intra-operative coordinates from the patient's physical joint in the coordinate system, generating a virtual surgical guide, determining a predetermined position and/or orientation of the virtual surgical guide based on the one or more intra-operative measurements, displaying and superimposing the virtual surgical guide, using the one or more head mounted displays, onto the physical joint based at least in part on coordinates of the predetermined position of the virtual surgical guide, and aligning the physical surgical guide or a physical saw blade with the virtual surgical guide to guide a bone cut of the joint.

In some embodiments, the one or more head mounted displays are registered in a common coordinate system. In some embodiments, the common coordinate system is a shared coordinate system.

In some embodiments, the virtual surgical guide is configured to guide a bone cut in a knee replacement, hip replacement, shoulder joint replacement or ankle joint replacement.

In some embodiments, the predetermined position of the virtual surgical guide determines a tibial slope for implantation of one or more tibial implant components in a knee replacement. In some embodiments, the predetermined position of the virtual surgical guide determines an angle of *varus* or valgus correction for a femoral and/or a tibial component in a knee replacement. In some embodiments, the virtual surgical guide corresponds to a physical distal femoral guide or cut block and the predetermined position of the virtual surgical guide determines a femoral component flexion.

In some embodiments, the virtual surgical guide corresponds to a physical anterior or posterior femoral surgical guide or cut block and the predetermined position of the virtual surgical guide determines a femoral component rotation. In some embodiments, the virtual surgical guide corresponds to a physical chamfer femoral guide or cut block. In some embodiments, the virtual surgical guide corresponds to a physical multi-cut femoral guide or cut block and the predetermined position of the virtual surgical guide determines one or more of an anterior cut, posterior cut, chamfer cuts and a femoral component rotation. In some embodiments, the virtual surgical guide is used in a hip replacement and the predetermined position of the virtual surgical guide determines a leg length after implantation. In some embodiments, the virtual surgical guide is a virtual plane for aligning the physical saw blade to guide the bone cut of the joint.

In some embodiments, the one or more intraoperative measurements include detecting one or more optical markers attached to the patient's joint, the operating room table, fixed structures in the operating room or combinations thereof. In some embodiments, one or more cameras or image capture or video capture systems and/or a 3D scanner included in the head mounted display can detect one or more optical markers including their coordinates (x, y, z) and at least one or more of a position, orientation, alignment, direction of movement or speed of movement of the one or more optical markers.

In some embodiments, registration of one or more of head mounted displays, surgical site, joint, spine, surgical instruments or implant components can be performed using spatial mapping techniques.

In some embodiments, registration of one or more of head mounted displays, surgical site, joint, spine, surgical instruments or implant components can be performed using depth sensors.

In some embodiments, the virtual surgical guide is configured to guide a bone cut of a distal tibia or a talus in an ankle joint replacement and the one or more head mounted display is configured to align the virtual surgical guide based on a predetermined tibial or talar implant component alignment, wherein the predetermined tibial or talar implant component alignment includes a coronal plane implant component alignment, a sagittal plane implant component alignment, an axial plane component alignment, an implant component rotation of an implant component or combinations thereof.

In some embodiments, the virtual surgical guide is configured to guide a bone cut of a proximal humerus in a shoulder joint replacement and wherein the one or more head mounted display is configured to align the virtual surgical guide based on a predetermined humeral implant component alignment, wherein the humeral implant component alignment includes a coronal plane implant component alignment, a sagittal plane implant component alignment, an axial plane component alignment, a humeral implant component rotation, or combinations thereof. Aspects of the disclosure relate to a system comprising at least one head mounted display and a library of virtual implants, wherein the library of virtual implants comprises at least one virtual implant component, wherein the virtual implant component has at least one dimension that corresponds to a dimension of the implant component or has a dimension that is substantially identical to the dimension of the implant component, wherein the at least one head mounted display is configured to display the virtual implant component in substantial alignment with a tissue intended for placement of the implant component, wherein the placement of the virtual implant component is intended to achieve a predetermined implant component position and/or orientation. In some embodiments, the system further comprises at least one user interface. Aspects of the disclosure relate to methods of selecting an implant or a prosthesis in three dimensions in a surgical site of a physical joint of a patient. In some embodiments, the method comprises registering, in a coordinate system, one or more head mounted displays worn by a user. In some embodiments, the head mounted display is a see-through head mounted display.

In some embodiments, the method comprises obtaining one or more intra-operative measurements from the physical joint of the patient to determine one or more intra-operative coordinates. In some embodiments, the method comprises registering the one or more intra-operative coordinates from the physical joint of the patient in the coordinate system. In some embodiments, the method comprises displaying a three-dimensional graphical representation of a first implant or prosthesis projected over the physical joint using the one or more head mounted displays. In some embodiments, the three-dimensional graphical representation of the first implant or prosthesis is from a library of three-dimensional graphical representations of physical implants or prostheses. In some embodiments, the three-dimensional graphical representation corresponds to at least one portion of the physical implant or prosthesis. In some embodiments, the method comprises moving the three-dimensional graphical representation of the first implant or prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint. In some embodiments, the method comprises visually evaluating the fit or alignment between the three-dimensional graphical representation of the first implant or prosthesis and the one or more of an internal or external margin, periphery, edge, perimeter, anteroposterior, mediolateral, oblique dimension, diameter, radius, curvature, geometry, shape or surface, of the one or more structures of the physical joint. In some embodiments, the method comprises repeating the steps of displaying, optionally moving and visually evaluating the fit or alignment with one or more three-dimensional graphical representations of one or more additional physical implants or prostheses, wherein the one or more additional physical implants or prostheses have one or more of a different dimension, size, diameter, radius, curvature, geometry shape or surface than the first and subsequently evaluated implant or prosthesis. In some embodiments, the method comprises selecting a three-dimensional graphical representation of an implant or prosthesis with a satisfactory fit relative to the one or more structures of the physical joint from the library of three-dimensional graphical representations of physical implants or prostheses.

In some embodiments, the method comprises obtaining one or more intra-operative measurements from the physical joint of the patient to determine one or more intra-operative coordinates and registering the one or more intra-operative coordinates from the physical joint of the patient in the coordinate system.

In some embodiments, the step of visually evaluating the fit includes comparing one or more of a radius, curvature, geometry, shape or surface of the graphical representation of the first or subsequent prosthesis with one or more of an articular radius, curvature, shape or geometry of the joint. In some embodiments, the graphical representation of the first or subsequent implant or prosthesis is moved to improve the fit between the one or more of a radius, curvature, geometry, shape or surface of the graphical representation of the first or subsequent prosthesis and the one or more of an articular radius, curvature, shape or geometry of the joint. In some embodiments, the one or more of the size, location, position, and orientation of the selected graphical representation of the implant or prosthesis with its final coordinates is used to develop or modify a surgical plan for implantation of the implant or prosthesis. In some embodiments, the one or more of the location, position or orientation of the selected graphical representation is used to determine one or more bone resections for implantation of the implant or prosthesis.

In some embodiments, the one or more of an internal or external margin, periphery, edge, perimeter, anteroposterior, mediolateral, oblique dimension, diameter, radius, curvature, geometry, shape or surface of one or more structures of the physical joint have not been surgically altered. In other embodiments, the one or more of an internal or external margin, periphery, edge, perimeter, anteroposterior, mediolateral, oblique dimension, diameter, radius, curvature, geometry, shape or surface of one or more structures of the physical joint have been surgically altered. For example, the surgically altering can include removal of bone or cartilage. In some embodiments, the bone removal can be a bone cut.

In some embodiments, the HMD is a see-through head mounted display. In some embodiments, the head mounted display is a virtual reality type head mounted display and the joint of the patient is imaged using one or more cameras and the images are displayed by the HMD.

In some embodiments, the satisfactory fit includes a fit within 1, 2, 3, 4 or 5 mm distance between the selected graphical representation of the prosthesis and at least portions of the one or more of an internal or external margin, periphery, edge, perimeter anteroposterior, mediolateral, oblique dimension, radius, curvature, geometry, shape or surface, of the one or more structures of the physical joint.

In some embodiments, the one or more structures of the physical joint include one or more anatomic landmarks. In some embodiments, the one or more anatomic landmarks define one or more anatomical or biomechanical axes.

In some embodiments, the steps of moving and visually evaluating the fit of the graphical representation of the prosthesis include evaluating the alignment of the graphical representation of the prosthesis relative to the one or more anatomic or biomechanical axis. In some embodiments, the step of moving the three-dimensional graphical representation of the prosthesis is performed with one, two, three, four, five or six degrees of freedom. In some embodiments, the step of moving the three-dimensional graphical representation of the prosthesis includes one or more of translation or rotation of the three-dimensional graphical representation of the prosthesis.

In some embodiments, the step of visually evaluating the fit or alignment between the three-dimensional graphical representation of the first or subsequent prosthesis includes comparing one or more of an anteroposterior or mediolateral dimension of one or more of the prosthesis components with one or more with one or more of an anteroposterior or mediolateral dimension of the distal femur or the proximal tibia of the joint. In some embodiments, the step of visually evaluating the fit or alignment between the three-dimensional graphical representation of the first or subsequent prosthesis includes comparing one or more of a dimension, size, radius, curvature, geometry shape or surface of at least portions of the prosthesis with one or more of a dimension, size, radius, curvature, geometry shape or surface of at least portions of a medial condyle or a lateral condyle of the joint.

In some embodiments, the joint is a knee joint and the prosthesis includes one or more components of a knee replacement device. In some embodiments, the joint is a hip joint and the prosthesis includes one or more components of a hip replacement device. In some embodiments, the joint is a shoulder joint and the prosthesis includes one or more components of a shoulder replacement device. In some embodiments, the joint is an ankle and the prosthesis includes one or more components of an ankle replacement device.

In some embodiments, the library of three-dimensional graphical representations of physical implants or prostheses includes symmetrical and asymmetrical implant's or prosthesis' components. In some embodiments, the symmetrical or asymmetrical implant's or prosthesis' components include at least one of symmetrical and asymmetrical femoral components and symmetrical and asymmetrical tibial components.

Aspects of the disclosure relate to methods of selecting a medical device in three dimensions in a physical site of a patient selected for implantation. In some embodiments, the method comprises registering, in a coordinate system, one or more HMDs worn by a user. In some embodiments, the method comprises obtaining one or more measurements from the physical site of the patient to determine one or more coordinates. In some embodiments, the method comprises registering the one or more coordinates from the physical site of the patient in the coordinate system. In some embodiments, the method comprises displaying a three-dimensional graphical representation of a first medical device projected over the physical site using the one or more HMDs. In some embodiments, the three-dimensional graphical representation of the first medical device is from a library of three-dimensional graphical representations of physical medical devices and the three-dimensional graphical representation corresponds to at least one portion of the physical first medical device.

In some embodiments, the method comprises moving the three-dimensional graphical representation of the first medical device to align with or to be near with or to intersect one or more of an internal or external margin, periphery, edge, perimeter, anteroposterior, mediolateral, oblique dimension, diameter, radius, curvature, geometry, shape or surface of one or more structures at the physical site. In some embodiments, the method comprises visually evaluating the fit or alignment between the three-dimensional graphical representation of the first medical device and the one or more of an internal or external margin, periphery, edge, perimeter, anteroposterior, mediolateral, oblique dimension, diameter, radius, curvature, geometry, shape or surface, of the one or more structures at the physical site. In some embodiments, the method comprises repeating the steps of displaying, optionally moving and visually evaluating the fit or alignment with one or more three-dimensional graphical representations of one or more additional physical medical devices, wherein the one or more additional physical medical devices have one or more of a different dimension, size, diameter, radius, curvature, geometry shape or surface than the first and subsequently evaluated medical device. In some embodiments, the method comprises selecting a three-dimensional graphical representation of a medical device with a satisfactory fit relative to the one or more structures at the physical site from the library of three-dimensional graphical representations of physical medical devices.

In some embodiments, the one or more structures at the physical site include an anatomic or pathologic tissue intended for implantation. In some embodiments, the one or more structures at the physical site include an anatomic or pathologic tissue surrounding or adjacent or subjacent to the intended implantation site. In some embodiments, the one or more structures at the physical site include a pre-existing medical device near the implantation site or adjacent or subjacent or opposing or articulating with or to be connected with the medical device planned for implantation. In some embodiments, the one or more structures at the physical site include a one or more of a tissue, organ or vascular surface, diameter, dimension, radius, curvature, geometry, shape or volume.

In some embodiments, the one or more HMDs are registered with the physical surgical site, using, for example, one or more markers, e.g. attached to the surgical site or attached near the surgical site (for example by attaching the one or more markers to an anatomic structure), one or more of a pre- or intra-operative imaging study. The one or more HMDs can display live images of the physical surgical site, one or more of a pre- or intra-operative imaging study, 2D or 3D images of the patient, graphical representations of one or more medical devices, and/or CAD files of one or more medical devices. In some embodiments, the one or more HMDs are registered in relationship to at least one marker, e.g. attached to the patient, for example a bony structure in a spine, knee, hip, shoulder or ankle joint, or attached to the OR table or another structure in the operating room.

In some embodiments, the information from the one or more structures at the physical site and from the one or more of a pre- or intra-operative imaging study, 2D or 3D images of the patient, graphical representations of one or more medical devices, CAD files of one or more medical devices are used to select one or more of an anchor or attachment mechanism or fixation member.

In some embodiments, the information from the one or more structures at the physical site and from the one or more of a pre- or intra-operative imaging study, 2D or 3D images of the patient, graphical representations of one or more medical devices, CAD files of one or more medical devices are used to direct one or more of an anchor or attachment mechanism or fixation member.

In some embodiments, the medical device is one or more of an implant an instrument. In some embodiments, the implant is an implant component. In some embodiments, the medical device can be, but not limited to, a joint replacement implant, a stent, a wire, a catheter, a screw, an otoplasty prosthesis, a dental implant, a dental implant component, a prosthetic disk, a catheter, a guide wire, a coil, an aneurysm clip.

Aspects of the disclosure relate to methods of aligning an implant or a prosthesis in a joint of a patient. In some embodiments, the method comprises registering, in a coordinate system, one or more HMDs worn by a user. In some embodiments, the method comprises obtaining one or more intra-operative measurements from the physical joint of the patient to determine one or more coordinates of the physical joint. In some embodiments, the method comprises registering the one or more coordinates of the physical joint of the patient in the coordinate system. In some embodiments, the method comprises displaying a three-dimensional graphical representation of an implant or implant component or a prosthesis or prosthesis component projected over the physical joint using the one or more HMDs, wherein the three-dimensional graphical representation corresponds to at least one portion of the physical prosthesis. In some embodiments, the method comprises moving the three-dimensional graphical representation of the prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint. In some embodiments, the method comprises registering one or more coordinates from the graphical representation of the prosthesis in the coordinate system after the moving and aligning.

In some embodiments, the moving of the three-dimensional graphical representation of the implant or prosthesis is performed using one or more of a computer interface (also referred to user interface), an acoustic interface, optionally including voice recognition, a virtual interface, optionally including gesture recognition. In some embodiments, the one or more coordinates from the graphical representation of the prosthesis in the coordinate system after the moving and aligning are used to derive or modify a surgical plan. In some embodiments, the one or more coordinates from the graphical representation of the implant or prosthesis in the coordinate system after the moving and aligning are used to determine one or more of a location, orientation, or alignment or coordinates of a bone removal for placing the implant or prosthesis. In some embodiments, the bone removal is one or more of a bone cut, a burring, a drilling, a pinning, a reaming, or an impacting. In some embodiments, the surgical plan is used to derive one or more of a location, position, orientation, alignment, trajectory, plane, start point, or end point for one or more surgical instruments. In some embodiments, the one or more of a location, orientation, or alignment or coordinates of bone removal are used to derive one or more of a location, position, orientation, alignment, trajectory, plane, start point, or end point for one or more surgical instruments. In some embodiments, the one or more HMDs visualize the one or more of a location, position, orientation, alignment, trajectory, plane, start point, or end point for one or more surgical instruments projected onto and registered with the physical joint. In some embodiments, the prosthesis is an acetabular cup of a hip replacement and wherein a graphical representation of the acetabular up is aligned with at least a portion of the physical acetabular rim of the patient. In some embodiments, the implant or prosthesis is a femoral component of a hip replacement and wherein a graphical representation of the femoral component is aligned with at least a portion of the physical endosteal bone or cortical bone of the patient. In some embodiments, the aligning means positioning the femoral component in substantially equidistant location between at least a portion of one or more of an anterior and a posterior endosteal or cortical bone or a medial and a lateral endosteal bone or cortical bone. In some embodiments, the femoral component includes a femoral neck. In some embodiments, the one or more coordinates from the femoral component in the coordinate system after the moving and aligning is used to determine at least one of a femoral component stem position, a femoral component stem orientation, a femoral component neck angle, a femoral component offset, and a femoral component neck anteversion. In some embodiments, the implant or prosthesis is a glenoid component of a shoulder replacement and wherein a graphical representation of the glenoid component is aligned with at least a portion of the physical glenoid rim of the patient. In some embodiments, the implant or prosthesis is a humeral component of a shoulder replacement and wherein a graphical representation of the humeral component is aligned with at least a portion of the physical endosteal bone or cortical bone of the patient. In some embodiments, the aligning means positioning the humeral component in substantially equidistant location between at least a portion of one or more of an anterior and a posterior endosteal or cortical bone or a medial and a lateral endosteal bone or cortical bone. In some embodiments, the humeral component includes a humeral neck. In some embodiments, the one or more coordinates from the humeral component in the coordinate system after the moving and aligning is used to determine at least one of a humeral component stem position, a humeral component stem orientation, a humeral component neck angle, a humeral component offset, and a humeral component neck anteversion. In some embodiments, the one or more of a margin, periphery, edge, perimeter, anteroposterior, mediolateral, oblique dimension, diameter, radius, curvature, geometry, shape or surface of one or more structures of the physical joint includes one or more of a cartilage, normal cartilage, damaged or diseased cartilage, subchondral bone or osteophyte. In some embodiments, the one or more of a margin, periphery, edge, perimeter, anteroposterior, mediolateral, oblique dimension, diameter, radius, curvature, geometry, shape or surface of one or more structures of the physical joint excludes one or more of a cartilage, normal cartilage, damaged or diseased cartilage, subchondral bone or osteophyte. In some embodiments, the one or more HMDs display registered with and superimposed onto the physical joint one or more of a pre- or intra-operative imaging study, 2D or 3D images of the patient, graphical representations of one or more medical devices, CAD files of one or more medical devices, wherein the display assists with the moving and aligning of the three-dimensional graphical representation of the graphical representation of the prosthesis. In some embodiments, the implant or prosthesis is a femoral component or a tibial component of a knee replacement system, wherein the one or more coordinates from the graphical representation of the implant or prosthesis in the coordinate system after the moving and aligning include a center of the graphical representation of the femoral component or a center of the graphical representation of the tibial component. In some embodiments, the moving or aligning includes aligning the femoral component on the distal femur. In some embodiments, the aligning includes aligning the femoral component substantially equidistant to a medial edge of the medial femoral condyle and the lateral edge of a lateral femoral condyle. In some embodiments, the aligning includes aligning the femoral component tangent with the articular surface of at least one of the medial condyle and the lateral condyle in at least one of a distal weight-bearing zone or a weight-bearing zone at 5, 10, 15, 20, 25, 30, 40 or 45 degrees of knee flexion. In some embodiments, the moving or aligning includes aligning the tibial component on the proximal tibia. In some embodiments, the aligning includes aligning the tibial component substantially equidistant to a medial edge of the medial tibial plateau and the lateral edge of a lateral tibial plateau and/or the anterior edge of the anterior tibial plateau and the posterior edge of the posterior tibial plateau or centered over the tibial spines. In some embodiments, the aligning includes aligning the tibial component tangent with at least portions of the articular surface of at least one of the medial tibial plateau and the lateral tibial plateau.

In some embodiments, the center of the graphical representation of the femoral component after the aligning and the center of the hip joint are used to determine a femoral mechanical axis. In some embodiments, the center of the graphical representation of the tibial component after aligning and the center of the ankle joint are used to determine a tibial mechanical axis. In some embodiments, the femoral and tibial mechanical axes are used to determine a desired leg axis correction relative to the mechanical axis of the leg. In some embodiments, the leg axis correction is one of a full correction to normal mechanical axis, partial correction to normal mechanical axis or no correction to normal mechanical axis. In some embodiments, the leg axis correction is used to determine the coordinates and/or alignment for the bone removal or bone cuts. In some embodiments, the bone removal or bone cuts for a full correction to normal mechanical axis or a partial correction to normal mechanical axis or no correction to normal mechanical axis are used to adjust the femoral and/or tibial prosthesis coordinates. In some embodiments, the bone removal or bone cuts are executed using at least one of a robot guidance, a surgical navigation system and visual guidance using the one or more of HMD. In some embodiments, the one or more HMDs project a graphical representation of one or more of a cut block, a cut plane or a drill path registered with and superimposed onto the physical joint for aligning one or more of a physical cut guide, a saw blade or a drill.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. The term live data of the patient, as used herein, includes the surgical site, anatomy, anatomic structures or tissues and/or pathology, pathologic structures or tissues of the patient as seen by the surgeon's or viewer's eyes without information from virtual data, stereoscopic views of virtual data, or imaging studies. The term live data of the patient does not include internal or subsurface tissues or structures or hidden tissues or structures that can only be seen with assistance of a computer monitor or HMD.

The terms real surgical instrument, actual surgical instrument, physical surgical instrument and surgical instrument are used interchangeably throughout the application; the terms real surgical instrument, actual surgical instrument, physical surgical instrument and surgical instrument do not include virtual surgical instruments. For example, the physical surgical instruments can be surgical instruments provided by manufacturers or vendors for spinal surgery, pedicle screw instrumentation, anterior spinal fusion, knee replacement, hip replacement, ankle replacement and/or shoulder replacement; physical surgical instruments can be, for example, cut blocks, pin guides, awls, reamers, impactors, broaches. Physical surgical instruments can be reuseable or disposable or combinations thereof. Physical surgical instruments can be patient specific. The term virtual surgical instrument does not include real surgical instrument, actual surgical instrument, physical surgical instrument and surgical instrument.

The terms real surgical tool, actual surgical tool, physical surgical tool and surgical tool are used interchangeably throughout the application; the terms real surgical tool, actual surgical tool, physical surgical tool and surgical tool do not include virtual surgical tools. The physical surgical tools can be surgical tools provided by manufacturers or vendors. For example, the physical surgical tools can be pins, drills, saw blades, retractors, frames for tissue distraction and other tools used for orthopedic, neurologic, urologic or cardiovascular surgery. The term virtual surgical tool does not include real surgical tool, actual surgical tool, physical surgical tool and surgical tool. The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical implants can be a pedicle screw, a spinal rod, a spinal cage, a femoral or tibial component in a knee replacement, an acetabular cup or a femoral stem and head in hip replacement. The term virtual implant or implant component does not include real implant or implant component, actual implant or implant component, physical implant or implant component and implant or implant component.

The terms "image capture system", "video capture system", "image or video capture system", "image and/or video capture system, and/or optical imaging system" can be used interchangeably. In some embodiments, a single or more than one, e.g. two or three or more, image capture system, video capture system, image or video capture system, image and/or video capture system, and/or optical imaging system can be used in one or more locations (e.g. in one, two, three, or more locations), for example integrated into, attached to or separate from an HMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, or an internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, or an external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more image capture system, video capture system, image or video capture system, image and/or video capture system, and/or optical imaging system can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ described in the specification or known in the art. Tracking of the one or more image capture system, video capture system, image or video capture system, image and/or video capture system, and/or optical imaging system can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, a single or more than one, e.g. two or three or more, 3D scanners can be present in one or more locations(e.g. in one, two, three, or more locations), for example integrated into, attached to or separate from an HMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, and/or internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, and/or external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more 3D scanners can be tracked using any of the registration and/or tracking methods described in the specification, e.g. direct tracking using optical imaging systems and/or a 3D scanner (s), in any of the foregoing locations and/or tissues and/or organs and any other location and/or tissue and/or organ mentioned in the specification or known in the art. Tracking of the one or more 3D scanners can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, one or more image capture system, video capture system, image or video capture system, image and/or video capture system, and/or optical imaging system can be used in conjunction with one or more 3D scanners, e.g. in any of the foregoing locations and/or tissues and/or organs and any other location and/or tissue and/or organ described in the specification or known in the art.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Aspects of the disclosure relates to devices, systems and methods for positioning a virtual path, virtual plane, virtual tool, virtual surgical instrument or virtual implant component in a mixed reality environment using a HMD device, optionally coupled to one or more processing units. With guidance in mixed reality environment, a virtual surgical guide, tool, instrument or implant can be superimposed onto the physical joint, spine or surgical site. Further, the physical guide, tool, instrument or implant can be aligned with the virtual surgical guide, tool, instrument or implant displayed or projected by the HMD. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, the HMD can display one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration.

In some embodiments, the one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration can be displayed by the HMD at one or more predetermined coordinates, e.g. indicating a predetermined position predetermined orientation or combination thereof for superimposing and/or aligning a physical surgical tool, physical surgical instrument, physical implant, or a physical device.

In some embodiments, one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration displayed by the HMD can be a placement indicator for one or more of a physical surgical tool, physical surgical instrument, physical implant, or a physical device.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a joint, a spine, a surgical site, a bone, a cartilage, a HMD, a surgical tool or instrument, a trial implant, an implant component or an implant.

In some embodiments, measurements can include measurements of coordinate(s) or coordinate information. A coordinate can be a set of numbers used in specifying the location of a point on a line, on a surface, or in space, e.g. x, y, z. Coordinate can be predetermined, e.g. for a virtual surgical guide.

In some embodiments, multiple coordinate systems can be used instead of a common or shared coordinate system. In this case, coordinate transfers can be applied from one coordinate system to another coordinate system, for example for registering the HMD, live data of the patient including the surgical site, virtual instruments and/or virtual implants and physical instruments and physical implants.

Head Mounted Displays

In some embodiments, head mounted displays (HMDs) can be used. Head mounted displays can be of non-see through type (such as the Oculus VR HMD (Facebook, San Mateo, CA)), optionally with a video camera to image the live data of the patient as a video-see through head mounted display, or they can be of optical see through type as an optical see-through head mounted display or see-through optical head mounted display.

A HMD can include a first display unit for the left eye and a second display unit for the right eye. The first and second display units can be transparent, semi-transparent or non-transparent. The system, comprising, for example, the HMD, one or more computer processors and/or an optional marker attached to the patient, can be configured to generate a first view of virtual data, e.g. a virtual surgical guide, for the first display unit and a second view of virtual data, e.g. a virtual surgical guide, for the second display unit. The virtual data can be a placement indicator for a physical surgical tool, physical surgical instrument, physical implant or physical device. The virtual data, e.g. a virtual surgical guide, can be a three-dimensional digital representation at one or more predetermined coordinates indicating, for example, a predetermined position, predetermined orientation or combination thereof for superimposing and/or aligning a physical surgical tool, physical surgical instrument, physical implant or physical device.

The system can be configured to generate a first view displayed by a first display unit (e.g. for the left eye) and a second view displayed by a second display unit (e.g. for the right eye), wherein the first view and the second view create a 3D stereoscopic view of the virtual data, e.g. a virtual surgical guide, which can optionally be based on one or more predetermined coordinates. The system can be configured to display the 3D stereoscopic view by the HMD onto the patient.

In some embodiments, a pair of glasses is utilized. The glasses can include an optical head-mounted display. An optical see through head-mounted display (OHMD) can be a wearable display that has the capability of reflecting projected images as well as allowing the user to see through it. Various types of OHMDs known in the art can be used in order to practice embodiments of the present disclosure. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the HMDs include, but are not limited to touchpad or buttons, smartphone controllers, speech recognition, and gesture recognition. Advanced interfaces are possible, e.g. a brain—computer interface.

Optionally, a computer or server or a workstation can transmit data to the HMD. The data transmission can occur via cable, Bluetooth, WiFi, optical signals and any other method or mode of data transmission known in the art. The HMD can display virtual data, e.g. virtual data of the patient, in uncompressed form or in compressed form. Virtual data of a patient can optionally be reduced in resolution when transmitted to the HMD or when displayed by the HMD.

When virtual data are transmitted to the HMD, they can be in compressed form during the transmission. The HMD can then optionally decompress them so that uncompressed virtual data are being displayed by the HMD.

Alternatively, when virtual data are transmitted to the HMD, they can be of reduced resolution during the transmission, for example by increasing the slice thickness of image data prior to the transmission. The HMD can then optionally increase the resolution, for example by re-interpolating to the original slice thickness of the image data or even thinner slices so that virtual data with resolution equal to or greater than the original virtual data or at least greater in resolution than the transmitted data are being displayed by the HMD.

In some embodiments, the HMD can transmit data back to a computer, a server or a workstation. Such data can include, but are not limited to:

Positional, orientational or directional information about the HMD or the operator or surgeon wearing the HMD Changes in position, orientation or direction of the HMD Data generated by one or more IMUs Data generated by markers (radiofrequency, optical, light, other) attached to, integrated with or coupled to the HMD Data generated by a surgical navigation system attached to, integrated with or coupled to the HMD Data generated by an image and/or video capture system attached to, integrated with or coupled to the HMD Parallax data, e.g. using two or more image and/or video capture systems attached to, integrated with or coupled to the HMD, for example one positioned over or under or near the left eye and a second positioned over or under or near the right eye Distance data, e.g. parallax data generated by two or more image and/or video capture systems evaluating changes in distance between the HMD and a surgical field or an object Motion parallax data Data related to calibration or registration phantoms (see other sections of this specification)

Any type of live data of the patient captured by the HMD including image and/or video capture systems attached to, integrated with or coupled to the HMD For example, alterations to a live surgical site For example, use of certain surgical instruments detected by the image and/or video capture system For example, use of certain medical devices or trial implants detected by the image and/or video capture system Any type of modification to a surgical plan Portions or aspects of a live surgical plan Portions or aspects of a virtual surgical plan Radiofrequency tags used throughout the embodiments can be of active or passive kind with or without a battery.

Exemplary optical see through head mounted displays include the ODG R-7, R-8 and R-8 smart glasses from ODG (Osterhout Group, San Francisco, CA), the NVIDIA 942 3-D vision wireless glasses (NVIDIA, Santa Clara, CA) the Microsoft Hololens and Hololens 2 (Microsoft, Redmond, WI), the Daqri Smart Glass (Daqri, Los Angeles, CA) the Metal (Meta Vision, San Mateo, CA), the Moverio BT-300 (Epson, Suwa, Japan), the Blade 3000 and the Blade M300 (Vuzix, West Henrietta, NY), and the Lenovo ThinkA6 (Lenovo, Beijing, China). The Microsoft HoloLens is manufactured by Microsoft. It is a pair of augmented reality smart glasses. Hololens is a see-through optical head mounted display (or optical see through head mounted display) 1125 (see FIG. 1). An optical see through head mounted display can include a clear or transparent front portion or visor 10, a combiner 12 or mirror system, a nose pad 15, a front facing portion 18, a side facing portion 20, and an occipital portion 22. At least one or more cameras 21 can be included, which can be used, for example, for inside-out-tracking. Hololens can use the Windows 10 operating system. The front portion of the Hololens includes, among others, sensors, related hardware, several cameras and processors. The visor includes a pair of transparent combiner lenses, in which the projected images are displayed. The HoloLens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present. The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor. Hololens has an Intel Cherry Trail SoC containing the CPU and GPU. HoloLens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. HoloLens includes a IEEE 802.11ac Wi-Fi and Bluetooth 4.1 Low Energy (LE) wireless connectivity. The headset uses Bluetooth LE and can connect to a clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application, Free-Form, integrating HoloLens with the Autodesk Fusion 360 cloud-based 3D development application, and others. HoloLens utilizing the HPU can employ sensual and natural interface commands—voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized. The HoloLens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around. The Microsoft HoloLens App for Windows 10 PC's and Windows 10 Mobile devices can be used by developers to run apps and to view live stream from the HoloLens user's point of view, and to capture augmented reality photos and videos. Almost all Universal Windows Platform apps can run on Hololens. These apps can be projected in 2D. Select Windows 10 APIs are currently supported by HoloLens. Hololens apps can also be developed on Windows 10 PC's. Holographic applications can use Windows Holographic APIs. Unity (Unity Technologies, San Francisco, CA) and Vuforia (PTC, Inc., Needham, MA) are some apps that can be utilized. Applications can also be developed using DirectX and Windows API's.

Many of the embodiments throughout the specification can be implemented also using non-see through head mounted displays, e.g. virtual reality head mounted displays. Non-see through head mounted displays can be used, for example, with one or more image or video capture systems (e.g. cameras) or 3D scanners to image the live data of the patient, e.g. a skin, a subcutaneous tissue, a surgical site, an anatomic landmark, an organ, or an altered tissue, e.g. a surgically altered tissue, as well as any physical surgical tools, instruments, devices and/or implants, or portions of the surgeon's body, e.g. his or her fingers, hands or arms. Non see through HMDs can be used, for example, for displaying virtual data, e.g. pre- or intra-operative imaging data of the patient, virtual surgical guides, virtual tools, virtual instruments, virtual implants and/or virtual implants, for example together with live data of the patient, e.g. from the surgical site, imaged through the one or more cameras or video or image capture systems or 3D scanners, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery.

Exemplary non-see through head mounted displays, e.g. virtual reality head mounted displays, are, for example, the Oculus Rift (Google, Mountain View, CA), the HTC Vive (HTC, Taipei, Taiwan) and the Totem (Vrvana, Apple, Cupertino, CA). When combined with a video camera, e.g. for streaming live images from a surgical site, these VR headsets can be configured as a video see through head mounted display.

Computer Graphics Viewing Pipeline

In some embodiments, the HMD uses a computer graphics viewing pipeline that consists of the following steps to display 3D objects or 2D objects positioned in 3D space or other computer-generated objects and models:

1. Registration; 2. View Projection

Registration: In some embodiments, the different objects to be displayed by the HMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality HMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection

In some embodiments, once all objects to be displayed have been registered and transformed into the common global coordinate system, they are prepared for viewing on a display by transforming their coordinates from the global coordinate system into the view coordinate system and subsequently projecting them onto the display plane. This view projection step can use the viewpoint and view direction to define the transformations applied in this step. For stereoscopic displays, such as an HMD, two different view projections can be used, one for the left eye and the other one for the right eye. For see through HMDs (augmented reality HMDs) the position of the viewpoint and view direction relative to the physical environment can be known in order to correctly superimpose the computer-generated objects with the physical environment. As the viewpoint and view direction change, for example due to head movement, the view projections are updated so that the computer-generated display follows the new view.

Positional Tracking Systems

In some embodiments, the position and/or orientation of the HMDs can be tracked. For example, in order to calculate and update the view projection of the computer graphics view pipeline as described in the previous section and to display the computer-generated overlay images in the HMD, the view position and direction needs to be known.

Different methods to track the HMDs can be used. For example, the HMDs can be tracked using outside-in tracking. For outside-in tracking, one or more external sensors or cameras can be installed in a stationary location, e.g. on the ceiling, the wall or on a stand. The sensors or camera capture the movement of the HMDs, for example through shape detection or markers attached to the HMDs or the user's head. The sensor data or camera image is typically processed on a central computer to which the one or more sensors or cameras are connected. The tracking information obtained on the central computer can then be used to compute the view projection for the HMD (including multiple HMDs). The view projection can be computed on the central computer or on the HMD. Outside-in tracking can be performed with use of surgical navigation system using, for example, infrared and/or RF markers, active and/or passive markers. One or more external infrared or RF emitters and receivers or cameras can be installed in a stationary location, e.g. on the ceiling, the wall or a stand or attached to the OR table. One or more infrared and/or RF markers, active and/or passive markers can be applied to the HMD for tracking the coordinates and/or the position and/or orientation of the HMD. One or more infrared and/or RF markers, active and/or passive markers can be applied to the anatomic structure or near the anatomic structure tracking the coordinates and/or the position and/or orientation of the anatomic structure. One or more infrared and/or RF markers, active and/or passive markers can be applied to a physical tool, physical instrument, physical implant or physical device tracking the coordinates and/or the position and/or orientation of the physical tool, physical instrument, physical implant or physical device. One or more infrared and/or RF markers, active and/or passive markers can be applied to the surgeon.

In some embodiments, outside-in tracking can be performed with use of an image capture or video capture system using, for example, optical markers, e.g. with geometric patterns. One or more external cameras can be installed in a stationary location, e.g. on the ceiling, the wall or a stand or attached to the OR table. One or more optical markers can be applied to the HMD for tracking the coordinates and/or the position and/or orientation of the HMD. One or more optical markers can be applied to the anatomic structure or near the anatomic structure tracking the coordinates and/or the position and/or orientation of the anatomic structure. One or more optical markers can be applied to a physical tool, physical instrument, physical implant or physical device tracking the coordinates and/or the position and/or orientation of the physical tool, physical instrument, physical implant or physical device. One or more optical markers can be applied to the surgeon.

In some embodiments, including for outside-in and inside-out tracking, a camera, image capture or video capture system can detect light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the specification, including for outside-in and inside-out tracking, a camera, image capture or video capture system can detect light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the specification, including for outside-in and inside-out tracking, a camera, image capture or video capture system can detect light from the spectrum visible and from the spectrum not visible to the human eye.

In some embodiments, including for outside-in and inside-out tracking, a marker, e.g. a marker with a geometric pattern and/or a marker used with a navigation system, can be configured to reflect or emit light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the specification, including for outside-in and inside-out tracking, a marker, e.g. a marker with a geometric pattern and/or a marker used with a navigation system, can be configured to reflect or emit light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the specification, including for outside-in and inside-out tracking, a marker, e.g. a marker with a geometric pattern and/or a marker used with a navigation system, can be configured to reflect or emit light from the spectrum visible and from the spectrum not visible to the human eye.

In some embodiments, outside-in tracking can be performed with use of a 3D scanner or a laser scanner. One or more external 3D scanners or laser scanners can be installed in a stationary location, e.g. on the ceiling, the wall or a stand or attached to the OR table. The 3D scanner or laser scanner can be used to track objects directly, e.g. the HMD, the anatomic structure, the physical tool, physical instrument, physical implant or physical device or the surgeon. Optionally, markers can be applied to one or more of the HMD, the anatomic structure, the physical tool, physical instrument, physical implant or physical device or the surgeon for tracking any of the foregoing using the 3D scanner or laser scanner.

In some embodiments, the inside-out tracking method can be employed. One or more sensors or cameras can be attached to the HMD or the user's head or integrated with the HMD. The sensors or cameras can be dedicated to the tracking functionality. The cameras attached or integrated into the HMD can include infrared cameras. Infrared LEDs or emitters can also be included in the HMD. The sensors or cameras attached or integrated into the HMD can include an image capture system, a video capture system, a 3D scanner, a laser scanner, a surgical navigation system or a depth camera. In some embodiments, the data collected by the sensors or cameras is used for positional tracking as well as for other purposes, e.g. image recording or spatial mapping. Information gathered by the sensors and/or cameras is used to determine the HMD's position and orientation in 3D space. This can be done, for example, by detecting optical, infrared, RF or electromagnetic markers attached to the external environment. Changes in the position of the markers relative to the sensors or cameras are used to continuously determine the position and orientation of the HMD. Data processing of the sensor and camera information can be performed by a mobile processing unit attached to or integrated with the HMD, which can allow for increased mobility of the HMD user as compared to outside-in tracking. Alternatively, the data can be transmitted to and processed on the central computer.

Inside-out tracking can also utilize markerless techniques. For example, spatial mapping data acquired by the HMD sensors can be aligned with a virtual model of the environment, thus determining the position and orientation of the HMD in the 3D environment. Alternatively, or additionally, information from inertial measurement units can be used. Potential advantages of inside-out tracking include greater mobility for the HMD user, a greater field of view not limited by the viewing angle of stationary cameras and reduced or eliminated problems with marker occlusion.

Eye and Gaze Tracking Systems

Some aspects of the present disclosure provide for methods and devices of using the human eye including eye movements and lid movements as well as movements induced by the peri-orbital muscles for executing computer commands. Methods of executing computer commands by way of facial movements and movements of the head are provided.

Command execution induced by eye movements and lid movements as well as movements induced by the peri-orbital muscles, facial movements and head movements can be advantageous in environments where an operator does not have his hands available to type on a keyboard or to execute commands on a touchpad or other hand—computer interface. Such situations include, but are not limited, to industrial applications including automotive and airplane manufacturing, chip manufacturing, medical or surgical procedures and many other potential applications.

In some embodiments, the head mount display can include an eye tracking system. Different types of eye tracking systems can be utilized. The examples provided below are in no way thought to be limiting. Any eye tracking system known in the art now can be utilized.

Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections. Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, optical or video-based eye trackers can be used. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retro reflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations. The optical tracking method can include tracking movement of the eye including the pupil as described above. The optical tracking method can also include tracking of the movement of the eye lids and also periorbital and facial muscles.

In some embodiments, the eye-tracking apparatus is integrated in a HMD. In some embodiments, head motion can be simultaneously tracked, for example using a combination of accelerometers and gyroscopes forming an inertial measurement unit (see below).

In some embodiments, electric potentials can be measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments.

A sampling rate of 15, 20, 25, 30, 50, 60, 100, 120, 240, 250, 500, 1000 Hz or greater can be used. Any sampling frequency is possibly. In many embodiments, sampling rates greater than 30 Hz will be preferred.

Measuring Location, Orientation, Acceleration

The location, orientation, and acceleration of the human head, portions of the human body, e.g. hands, arms, legs or feet, as well as portions of the patient's body, e.g. the patient's head or extremities, including the hip, knee, ankle, foot, shoulder, elbow, hand or wrist and any other body part, can, for example, be measured with a combination of gyroscopes and accelerometers. In select applications, magnetometers may also be used. Such measurement systems using any of these components can be defined as inertial measurement units (IMU).

As used herein, the term IMU relates to an electronic device that can measure and transmit information on a body's specific force, angular rate, and, optionally, the magnetic field surrounding the body, using a combination of accelerometers and gyroscopes, and, optionally, magnetometers. An IMU or components thereof can be coupled with or registered with a navigation system or a robot, for example by registering a body or portions of a body within a shared coordinate system. Optionally, an IMU can be wireless, for example using WiFi networks or Bluetooth networks.

Pairs of accelerometers extended over a region of space can be used to detect differences (gradients) in the proper accelerations of frames of references associated with those points. Single- and multi-axis models of accelerometer are available to detect magnitude and direction of the acceleration, as a vector quantity, and can be used to sense orientation (because direction of weight changes), coordinate acceleration (so long as it produces g-force or a change in g-force), vibration, shock. Micromachined accelerometers can be utilized in some embodiments to detect the position of the device or the operator's head.

Piezoelectric, piezoresistive and capacitive devices can be used to convert the mechanical motion into an electrical signal. Piezoelectric accelerometers rely on piezoceramics or single crystals Piezoresistive accelerometers can also be utilized. Capacitive accelerometers typically use a silicon micro-machined sensing element. Accelerometers used in some of the embodiments can include small micro electro-mechanical systems (MEMS), consisting, for example, of little more than a cantilever beam with a proof mass. Optionally, the accelerometer can be integrated in the head mounted devices and both the outputs from the eye tracking system and the accelerometer(s) can be utilized for command execution.

With an IMU, the following exemplary information can be captured about the operator and the patient and respective body parts including a moving joint: Speed, velocity, acceleration, position in space, positional change, angular orientation, change in angular orientation, alignment, orientation, and/or direction of movement and or speed of movement (e.g. through sequential measurements). Operator and/or patient body parts about which such information can be transmitted by the IMU include, but are not limited to: head, chest, trunk, shoulder, elbow, wrist, hand, fingers, arm, hip, knee, ankle, foot, toes, leg, inner organs, e.g. brain, heart, lungs, liver, spleen, bowel, bladder, etc.

Any number of IMUS can be placed on the HMD, the operator and/or the patient and, optionally, these IMUS can be cross-referenced to each other within a single or multiple coordinate systems or, optionally, they can be cross-referenced in relationship to an HMD, a second and third or more HMDs, a navigation system or a robot and one or more coordinate systems used by such navigation system and/or robot. A navigation system can be used in conjunction with an HMD without the use of an IMU. For example, navigation markers including infrared markers, retroreflective markers, RF markers can be attached to an HMD and, optionally, portions or segments of the patient or the patient's anatomy. The HMD and the patient or the patient's anatomy can be cross-referenced in this manner or registered in one or more coordinate systems used by the navigation system and movements of the HMD or the operator wearing the HMD can be registered in relationship to the patient within these one or more coordinate systems. Once the virtual data and the live data of the patient and the HMD are registered in the same coordinate system, e.g. using IMUS, optical markers, navigation markers including infrared markers, retroreflective markers, RF markers, and any other registration method described in the specification or known in the art, any change in position of any of the HMD in relationship to the patient measured in this fashion can be used to move virtual data of the patient in relationship to live data of the patient, so that the visual image of the virtual data of the patient and the live data of the patient seen through the HMD are always aligned, irrespective of movement of the HMD and/or the operator's head and/or the operator wearing the HMD. Similarly, when multiple HMDs are used, e.g. one for the primary surgeon and additional ones, e.g. two, three, four or more, for other surgeons, assistants, residents, fellows, nurses and/or visitors, the HMDs worn by the other staff, not the primary surgeon, will also display the virtual representation(s) of the virtual data of the patient aligned with the corresponding live data of the patient seen through the HMD, wherein the perspective of the virtual data that is with the patient and/or the surgical site for the location, position, and/or orientation of the viewer's eyes for each of the HMDs used and each viewer. The foregoing embodiments can be achieved since the IMUS, optical markers, RF markers, infrared markers and/or navigation markers placed on the operator and/or the patient as well as any spatial anchors can be registered in the same coordinate system as the primary HMD and any additional HMDs. The position, orientation, alignment, and change in position, orientation and alignment in relationship to the patient and/or the surgical site of each additional HMD can be individually monitored thereby maintaining alignment and/or superimposition of corresponding structures in the live data of the patient and the virtual data of the patient for each additional HMD irrespective of their position, orientation, and/or alignment in relationship to the patient and/or the surgical site.

One or more IMUS can also be attached to or integrated into a surgical helmet. When an HMD is integrated into or attached to the surgical helmet, the IMU integrated into or attached to the surgical helmet can be used for determining the position and/or orientation of the HMD. Alternatively, one or more IMUS can be integrated into or attached to the surgical helmet and the HMD. The data generated by the IMUS integrated into or attached to the surgical helmet can be compared to the data generated by the IMUS integrated into or attached to the HMD and their position and/or orientation relative to each other can be determined by comparing the data using one or more computer processors.

User Interfaces

Aspects of the present disclosure provide a user interface where the human eye including eye movements and lid movements including movements induced by the orbital and peri-orbital and select skull muscles are detected by the eye tracking system and are processed to execute predefined, actionable computer commands.

An exemplary list of eye movements and lid movements that can be detected by the system is provided in Table 1.

TABLE 1

Exemplary list of eye movements and lid movements detected by the eye tracking software 1 blink
2 blinks
3 blinks
Fast blink, for example less than 0.5 seconds
Slow blink, for example more than 1.0 seconds
2 or more blinks with fast time interval, e.g. less than 1 second
2 or more blinks with long time interval, e.g. more than 2 seconds (typically chosen to be less than the natural time interval between eye blinks)
Blink left eye only
Blink right eye only
Blink left eye and right eye simultaneously
Blink left eye first, then within short time interval (e.g. less than 1 second), blink right eye
Blink right eye first, then within short time interval (e.g. less than 1 second), blink lef teye
Blink left eye first, then within long time interval (e.g. more than 2 seconds), blink right eye
Blink right eye first, then within long time interval (e.g. more than 2 seconds), blink left eye
Rapid eye movement to left
Rapid eye movement to right
Rapid eye movement up
Rapid eye movement down
Widen eyes, hold for short time interval, e.g. less than 1 second
Widen eyes, hold for long time interval, e.g. more than 2 seconds
Close both eyes for 1 second etc.
Close both eyes for 2 seconds or more etc.
Close both eyes, hold, then open and follow by fast blink
Close left eye only 1 second, 2 seconds etc.
Close right eye only 1 second, 2 seconds etc.
Close left eye, then right eye
Close right eye, then left eye
Blink left eye, then right eye
Blink right eye, then left eye
Stare at field, virtual button for 1, 2, 3 or more seconds; activate function, e.g. Zoom in or Zoom out Any combination of blinks, eye movements, sequences, and time intervals is possible for encoding various types of commands. These commands can be computer commands that can direct or steer, for example, a surgical instrument or a robot. Methods of executing commands by way of facial movements and movements of the head are also provided.

An exemplary list of facial movements and head movements that can be detected by the system is provided in Table 2. (This list is only an example and by no way meant to be exhaustive; any number or combination of movements is possible).

TABLE 2

Exemplary list of facial movements and head movements detected:

Move head fast to right and hold
Move head fast to left and hold
Move head fast down and hold
Move head fast down and hold
Move head fast to right and back
Move head fast to left and back
Move head fast down and back
Move head fast down and back
Tilt head to left and hold
Tilt head to right and hold
Tilt head to left and back
Tilt head to right and back
Open mouth and hold
Open mouth and close
Twitch nose once
Twitch nose twice etc.

Exemplary commands executed using eye movements, lid movements, facial movements and head movements are listed in Table 3.

TABLE 3

Exemplary list of commands that can be executed by tracking eye movement, lid movement, facial movement and head movement (this list is only an example and by no way meant to be exhaustive; any number or combination of commands is possible; application specific commands can be executed in this manner as well).

Click
Point
Move pointer
Slow
Fast
Scroll, e.g. through images
Fast scroll
Slow scroll
Scroll up
Scroll down
Scroll left
Scroll right
Drag
Swoosh
Register
Toggle 2D vs. 3D
Switch imaging study
Overlay images
Fuse images
Register images
Cut
Paste
Copy
Undo
Redo
Delete
Purchase
Provide credit card information
Authorize
Go to shopping card
HMD on
HMD off
Eye tracking on
Eye tracking off
Eye command execution on
Eye command execution off
Facial command execution on
Facial command execution off
Turn surgical instrument on (e.g. oscillating saw, laser etc.)
Turn surgical instrument off
Increase intensity, speed, energy deposed of surgical instrument
Reduce intensity, speed, energy deposed of surgical instrument TABLE 3-continued Exemplary list of commands that can be executed by tracking eye movement, lid movement, facial movement and head movement (this list is only an example and by no way meant to be exhaustive; any number or combination of commands is possible; application specific commands can be executed in this manner as well).

Change direction of surgical instrument
Change orientation of surgical instrument
Change any type of setting surgical instrument In some embodiments, eye movements, lid movements, facial movement, head movements alone or in combination can be used to signal numerical codes or sequences of numbers or sequences of machine operations. Such sequences of numbers can, for example, be used to execute certain machine operating sequences.

Other user interfaces can be a physical keyboard, physical track pad, physical mouse, physical joy stick, acoustic interface, voice recognition, virtual interface, virtual slider, virtual keyboard, virtual track pad, virtual mouse, virtual joy stick, gesture recognition, eye tracking, e.g. in relationship to a virtual interface.

Fusing Physical World with Imaging and Other Data of a Patient

In some embodiments, an operator such as a surgeon may look through an HMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other. The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the present disclosure; this list is not exhaustive, but only exemplary. Anyone skilled in the art can identify other scanning or imaging techniques that can be used in practicing the present disclosure: X-ray imaging, 2D, 3D, supine, upright or in other body positions and poses, including analog and digital x-ray imaging; Digital tomosynthesis; Cone beam CT; Ultrasound; Doppler ultrasound; Elastography, e.g. using ultrasound or MRI; CT; MRI, including, for example, fMRI, diffusion imaging, stroke imaging, MRI with contrast media; Functional MRI (fMRI), e.g. for brain imaging and functional brain mapping; Magnetic resonance spectroscopy; PET; SPECT-CT; PET-CT; PET-MRI; Upright scanning, optionally in multiple planes or in 3D using any of the foregoing modalities, including x-ray imaging, ultrasound etc.; Contrast media (e.g. iodinated contrast agents for x-ray and CT scanning, or MRI contrast agents; contrast agents can include antigens or antibodies for cell or tissue specific targeting; other targeting techniques, e.g. using liposomes, can also be applied; molecular imaging, e.g. to highlight metabolic abnormalities in the brain and target surgical instruments towards area of metabolic abnormality; any contrast agent known in the art can be used in conjunction with the present disclosure); 3D optical imaging, including Laser scanning, Confocal imaging, e.g. including with use of fiberoptics, single bundle, multiple bundle, Confocal microscopy, e.g. including with use of fiberoptics, single bundle, multiple bundles, Optical coherence tomography, Photogrammetry, Stereovision (active or passive), Triangulation (active or passive), Interferometry, Phase shift imaging, Active wavefront sampling, Structured light imaging, Other optical techniques to acquire 3D surface information, Combination of imaging data, e.g. optical imaging, wavefront imaging, interferometry, optical coherence tomography and/or confocal laser imaging or scanning, Image fusion or co-display of different imaging modalities, e.g. in 2D or 3D, optionally registered, optionally more than two modalities combined, fused or co-displayed, e.g. optical imaging, e.g. direct visualization or through an arthroscope, and/or laser scan data, e.g. direct visualization or through an arthroscope, and/or virtual data, e.g. intra-articular, extra-articular, intra-osseous, hidden, not directly visible, and/or external to skin, and/or confocal imaging or microscopy images/data, e.g. direct visualization or through an arthroscope. For a detailed description of illustrative scanning and imaging techniques, see for example, Bushberg et al. The Essential Physics of Medical Imaging, $3^{rd}$ edition, Wolters, Kluwer, Lippincott, 2012.

In embodiments, 3D scanning can be used for imaging of the patient and/or the surgical site and/or anatomic landmarks and/or pathologic structures and/or tissues (e.g. damaged or diseased cartilage or exposed subchondral bone) and/or the surgeon's hands and/or fingers and/or the OR table and/or reference areas or points and/or marker, e.g. optical markers, in the operating room and/or on the patient and/or on the surgical field. 3D scanning can be accomplished with multiple different modalities including combinations thereof, for example, optical imaging, e.g. using a video or image capture system integrated into, attached to, or separate from one or more HMDs, laser scanning, confocal imaging, optical coherence tomography, photogrammetry, active and passive stereovision and triangulation, interferometry and phase shift principles and/or imaging, wavefront sampling and/or imaging. One or more optical imaging systems or 3D scanners can, for example, be used to image and/or monitor, e.g. the coordinates, position, orientation, alignment, direction of movement, speed of movement of, Anatomic landmarks, patient surface(s), organ surface(s), tissue surface(s), pathologic tissues and/or surface(s), e.g. for purposes of registration, e.g. of the patient and/or the surgical site, e.g. one or more bones or cartilage, and/or one or more HMDs, e.g. in a common coordinate system The surgeon's hands and/or fingers, e.g. for
Monitoring steps in a surgical procedure. Select hand and/or finger movements can be associated with corresponding surgical steps. When the 3D scanner system detects a particular hand and/or finger movement, it can trigger the display of the corresponding surgical step or the next surgical step, e.g. by displaying a predetermined virtual axis, e.g. a reaming, broaching or drilling axis, a virtual cut plane, a virtual instrument, a virtual implant component etc.
Executing virtual commands, e.g. using gesture recognition or a virtual interface, e.g. a virtual touch pad
One or more HMDs, e.g. registered in a common coordinate system, e.g. with the surgical site and/or the surgeon's hands and/or fingers The use of optical imaging systems and/or 3D scanners for registration, e.g. of the surgical site and/or one or more HMDs can be helpful when markerless registration is desired, e.g. without use of optical markers, e.g. with geometric patterns, and/or IMUS, and/or LEDs, and/or navigation markers. The use of optical imaging systems and/or 3D scanners for registration can also be combined with the use of one or more of optical markers, e.g. with geometric patterns, and/or IMUS, and/or LEDs, and/or navigation markers.

In embodiments, one or more 3D models and/or 3D surfaces generated by an optical imaging system and/or a 3D scanner can be registered with, superimposed with and/or aligned with one or more 3D models and/or 3D surfaces generated by another imaging test, e.g. a CT scan, MRI scan, PET scan, other scan, or combinations thereof, and/or a 3D model and/or 3D surfaces generated from or derived from an x-ray or multiple x-rays, e.g. using bone morphing technologies, as described in the specification or known in the art.

With optical imaging systems or 3D scanners, a virtual 3D model can be reconstructed by postprocessing single images, e.g. acquired from a single perspective. In this case, the reconstruction cannot be performed in real time with continuous data capture. Optical imaging systems or 3D scanners can also operate in real time generating true 3D data.

For example, with confocal microscopy using, for example, an active triangulation technique, a projector can project a changing pattern of light, e.g. blue light, onto the surgical field, e.g. an articular surface exposed by arthroscopy or a bone or a soft-tissue, e.g. using projection grids that can have a transmittance random distribution and which can be formed by sub regions containing transparent and opaque structures. By using elements for varying the length of the optical path, it can possible, for each acquired profile, to state a specific relationship between the characteristic of the light and the optical distance of the image plane from the imaging optics. A light source can produce an illumination beam that can be focused onto the surface of the surgical field, e.g. the articular surface. An image sensor can receive the observation beam reflected by the surface of the target object. A focusing system can focus the observation beam onto the image sensor. The light source can split into a plurality of regions that can be independently regulated in terms of light intensity. Thus, the intensity of light detected by each sensor element can be a direct measure of the distance between the scan head and a corresponding point on the target object.

Parallel confocal imaging can be performed, e.g. by shining an array of incident laser light beams, e.g. passing through focusing optics and a probing face, on the surgical field, e.g. an articular surface, a bone or a soft-tissue. The focusing optics can define one or more focal planes forward to the probe face in one or more positions which can be changed, e.g. by a motor or other mechanism. The laser light beams can generate illuminated spots or patterns on the surgical field and the intensity of returning light rays can be measured at various positions of the focal plane determining spot-specific positions yielding a maximum intensity of the reflected light beams. Data can be generated which can represent the topology of the three-dimensional structure of the surgical field, e.g. an articular surface, e.g. exposed and/or visible and/or accessible during arthroscopy, a bone or a soft-tissue. By determining surface topologies of adjacent portions or tissues, e.g. an adjacent articular surface or bone or soft-tissue, from two or more different angular locations and then combining such surface topologies, a complete three-dimensional representation of the entire surgical field can be obtained. Optionally, a color wheel can be included in the acquisition unit itself. In this example, a two-dimensional (2D) color image of the 3D structure of the surgical field, e.g. an articular surface, a bone or a soft-tissue, can also be taken at the same angle and orientation with respect to the structure. Thus, each point with its unique coordinates on the 2D image can correspond to a similar point on the 3D scan having the same x and y coordinates. The imaging process can be based on illuminating the target surface with three differently-colored illumination beams (e.g. red, green or blue light) combinable to provide white light, thus, for example, capturing a monochromatic image of the target portion of the surgical field, e.g. an articular surface, a bone, a cartilage or a soft-tissue, corresponding to each illuminating radiation. The monochromatic images can optionally be combined to create a full color image. Three differently-colored illumination beams can be provided by means of one white light source optically coupled with color filters.

With optical coherence tomography (OCT), using, for example, a confocal sensor, a laser digitizer can include a laser source, e.g. coupled to a fiber optic cable, a coupler and a detector. The coupler can split the light from the light source into two paths. The first path can lead to the imaging optics, which can focus the beam onto a scanner mirror, which can steer the light to the surface of the surgical field, e.g. an articular surface, e.g. as seen or accessible during arthroscopy, a cartilage, a bone and/or a soft-tissue. A second path of light from the light source can be coupled via the coupler to the optical delay line and to the reflector. The second path of light, e.g. the reference path, can be of a controlled and known path length, as configured by the parameters of the optical delay line. Light can be reflected from the surface of the surgical field, e.g. an articular surface, a cartilage, a bone and/or a soft-tissue, returned via the scanner mirror and combined by the coupler with the reference path light from the optical delay line. The combined light can be coupled to an imaging system and imaging optics via a fiber optic cable. By utilizing a low coherence light source and varying the reference path by a known variation, the laser digitizer can provide an optical coherence tomography (OCT) sensor or a low coherence reflectometry sensor. The focusing optics can be placed on a positioning device in order to alter the focusing position of the laser beam and to operate as a confocal sensor. A series of imaged laser segments on the object from a single sample/tissue position can be interlaced between two or multiple 3D maps of the sample/tissue from essentially the same sample/tissue position. The motion of the operator between each subframe can be tracked mathematically through reference points. Operator motion can optionally be removed.

Active wavefront sampling and/or imaging can be performed using structured light projection. The scanning system can include an active three-dimensional imaging system that can include an off-axis rotating aperture element, e.g. placed in the illumination path or in the imaging path. Out-of-plane coordinates of object points can be measured by sampling the optical wavefront, e.g. with an off-axis rotating aperture element, and measuring the defocus blur diameter. The system can include a lens, a rotating aperture element and an image plane. The single aperture can help avoid overlapping of images from different object regions and can help increase spatial resolution. The rotating aperture can allow taking images at several aperture positions. The aperture movement can make it possible to record on a CCD element a single exposed image at different aperture locations. To process the image, localized cross correlation can be applied to reveal image disparity between image frames.

In another embodiment, a scanner can use a polarizing multiplexer. The scanner can project laser sheet onto the surgical cite, e.g. an articular surface, e.g. as exposed or accessible during arthroscopy, a cartilage, damaged, diseased or normal, a subchondral bone, a cortical bone etc., and can then utilize the polarizing multiplexer to optically combine multiple views of the profile illuminated by the sheet of laser light. The scanner head can use a laser diode to create a laser beam that can pass through a collimating lens which can be followed by a sheet generator lens that can convert the beam of laser light into a sheet of laser light. The sheet of laser light can be reflected by a folding mirror and can illuminate the surface of the surgical field. A system like this can optionally combine the light from two perspectives onto a single camera using passive or active triangulation. A system like this system can be configured to achieve the independence of lateral resolution and depth of field. In order to achieve this independence, the imaging system, can be physically oriented so as to satisfy the Scheimpflug principle. The Scheimpflug principle is a geometric rule that describes the orientation of the plane of focus of an optical system wherein the lens plane is not parallel to the image plane. This enables sheet of light based triangulation systems to maintain the high lateral resolution required for applications requiring high accuracy, e.g. accuracy of registration, while providing a large depth of focus.

A 3D scanner probe can sweep a sheet of light across one or more tissue surfaces, where the sheet of light projector and imaging aperture within the scanner probe can rapidly move back and forth along all or part of the full scan path, and can display, for example near real-time, a live 3D preview of the digital 3D model of the scanned tissue surface(s). A 3D preview display can provide feedback on how the probe is positioned and oriented with respect to the target tissue surface.

In other embodiments, the principle of active stereo photogrammetry with structured light projection can be employed. The surgical field can be illuminated by a 2D array of structured illumination points. 3D models can be obtained from the single image by triangulation with a stored image of the structured illumination onto a reference surface such as a plane. A single or multiple camera can be used. To obtain information in z-direction, the surgical site can be illuminated by a 2D image of structured illumination projected from a first angle with respect to the surgical site. Then the camera can be positioned at a second angle with respect to the surgical site, to produce a normal image containing two-dimensional information in x and y direction as seen at that second angle. The structured illumination projected from a photographic slide can superimpose a 2D array of patterns over the surgical site and can appear in the captured image. The information in z-direction is then recovered from the camera image of the surgical site under the structured illumination by performing a triangulation of each of the patterns in the array on the image with reference to an image of the structured illumination projected on a reference plane, which can also be illuminated from the first angle. In order to unambiguously match corresponding points in the image of the surgical site and in the stored image, the points of the structured illumination can be spatially-modulated with two-dimensional random patterns which can be generated and saved in a projectable medium. Random patterns are reproducible, so that the patterns projected onto the surgical site to be imaged are the same as the corresponding patterns in the saved image.

Accordion fringe interferometry (AFI) can employ light from two-point sources to illuminate an object with an interference fringe pattern. A high precision digital camera can be used to record the curvature of the fringes. The degree of apparent fringe curvature coupled with the known geometry between the camera and laser source enable the AFI algorithms to digitize the surface of the object being scanned. AFI can offer advantages over other scanners as lower sensitivity to ambient light variations and noise, high accuracy, large projector depth of field, enhanced ability to scan shiny and translucent surfaces, e.g. cartilage, and the ability to scan without targets and photogrammetric systems. A grating and lens can be used. Alternatively, coherent point source of electromagnetic radiation can also be generated without a grating and lens. For example, electromagnetic radiation can be emitted from a pair or pairs of optical fibers which can be used to illuminate target objects with interferometric fringes. Consequently, movement of a macroscopic grating which requires several milliseconds or more to effect a phase shift can be avoided. A fiber-based phase shifter can be used to change the relative phase of the electromagnetic radiation emitted from the exit ends of two optical fibers in a few microseconds or less. Optical radiation scattered from surfaces and subsurface regions of illuminated objects can be received by a detector array. Electrical signals can be generated by a detector array in response to the received electromagnetic radiation. A processor receives the electrical signals and calculates three-dimensional position information of tissue surfaces based on changes in the relative phase of the emitted optical radiation and the received optical radiation scattered by the surfaces. Sources of optical radiation with a wavelength between about 350 nm and 500 nm can be used; other wavelengths are possible.

Other optical imaging systems and/or 3D scanners can use the principle of human stereoscopic vision and the principle of linear projection: if straight lines are projected onto an object the lines will be curved around the object. This distortion of the lines allows conclusions to be drawn about the surface contour.

When optical imaging and/or 3D scanning is performed in the context of an arthroscopy procedure, the optical imaging and/or 3D scanning apparatus can be integrated into the endoscope, including by sharing the same fiberoptic(s) or with use of separate fiberoptic(s), e.g. in the same housing or a separate housing. An arthroscopic optical imaging and/or 3D scanning probe can be inserted through the same portal as the one used for the arthroscope, including when integrated into the arthroscope or in a common housing with the arthroscope, or it can be inserted through a second, separate portal. An optical imaging and/or 3D scanning probe used with an arthroscopic procedure can optionally be tracked by tracking the position, location, orientation, alignment and/or direction of movement using optical markers, e.g. with one or more geometric patterns, e.g. in 2D or 3D, or LEDs using one or more camera or video systems integrated into, attached to, or separate from one or more HMDs. The camera or video systems can be arranged at discrete, defined angles thereby utilizing angular information including parallax information for tracking distances, angles, orientation or alignment of optical markers attached to the probe, e.g. the arthroscope and/or optical imaging and/or 3D scanning probe. An optical imaging and/or 3D scanning probe and/or an arthroscope used with an arthroscopic procedure can optionally be tracked by tracking the position, location, orientation, alignment and/or direction of movement using navigation markers, e.g. infrared or RF markers, and a surgical navigation system. An optical imaging and/or 3D scanning probe and/or an arthroscope used with an arthroscopic procedure can optionally be tracked by tracking the position, location, orientation, alignment and/or direction of movement directly with one or more camera or video systems integrated into, attached to or separate from one or more HMDs, wherein a computer system and software processing the information can use image processing and pattern recognition to recognize the known geometry of the one or more probes and their location within a coordinate system, e.g. in relationship to the patient, the surgical site and/or the OR table. With any of the optical imaging and/or 3D scanner techniques, if there are holes in the acquisition and/or scan and/or 3D surface, repeat scanning can be performed to fill the holes. The scanned surface can also be compared against a 3D surface or 3D model of the surgical site, e.g. an articular surface, a cartilage, damaged or diseased or normal, a subchondral bone, a bone and/or a soft-tissue, obtained from an imaging study, e.g. an ultrasound, a CT or MRI scan, or obtained via bone morphing from x-rays as described in other parts of the specification. Discrepancies in surface geometry between the 3D model or 3D surface generated with the optical imaging system and/or the 3D scanner and the 3D surface or 3D model obtained from an imaging study or bone morphing from x-rays, can be determined; similarly, it can be determined if the surfaces or 3D models display sufficient commonality to allow for registration of the intra-operative 3D surface or 3D model obtained with the optical imaging system and/or 3D scanner and the 3D surface or 3D model obtained from the pre-operative imaging study or bone morphing from x-rays. If there is not sufficient commonality, additional scanning can be performed using the optical imaging and/or 3D scanner technique, for example in order to increase the spatial resolution of the scanned data, the accuracy of the scanned data and/or to fill any holes in the model or surface. Any surface matching algorithm known in the art can be utilized to register overlapping surface areas and thereby transform all surface portions into the same coordinate space, for example the Iterative Closest Point method described in Besl et al., *A Method for Registration of 3-D Shapes;* 1992; IEEE Trans PAM/14(2): 239-255.

Optionally, with any of the foregoing embodiments, the optical imaging system or 3D scanner can have a form of boot or stabilization advice attached to it, which can, for example, be rested against and moved over the target tissue, e.g. an articular surface, a bone or a soft-tissue. The boot or stabilization device can help maintain a constant distance between the scanner and the target tissue. The boot or stabilization device can also help maintain a constant angle between the scanner and the target tissue. For example, a boot or stabilization device can be used with an optical imaging system or scanner used during arthroscopy, maintaining, for example, a constant distance to the articular surface or intra-articular ligament, cartilage, bone or other structures, e.g. a femoral notch or a tibial spine or a tri-radiate cartilage region or fovea capitis in a hip. Multi-Dimensional Imaging, Reconstruction and Visualization Various embodiments can be practiced in one, two, three or more dimensions. The following is an exemplary list of potential dimensions, views, projections, angles, or reconstructions that can be applied; this list is not exhaustive, but only exemplary. Anyone skilled in the art can identify additional dimensions, views, projections, angles or reconstructions that can be used in practicing the present disclosure. Exemplary dimensions are listed in Table 4.

TABLE 4

Exemplary list of potential dimensions, views, projections, angles, or reconstructions that can be displayed using virtual representations with HMD(s), optionally stereoscopic $1^{st}$ dimension: superoinferior, e.g. patient physical data
$2^{nd}$ dimension: mediolateral, e.g. patient physical data
$3^{rd}$ dimension: anteroposterior, e.g. patient physical data
$4^{th}$-$6^{th}$ dimension: head motion (and with it motion of glasses/HMD) in 1, 2 or 3 dimensions
$7^{th}$-$9^{th}$ dimension: instrument motion in 1, 2 or 3 dimensions, e.g. in relationship to surgical field, organ or head including head motion
$10^{th}$-$13^{th}$ dimension: arm or hand motion in 1, 2 or 3 dimensions, e.g. in relationship to surgical field, organ or head including head motion
$14^{th}$-$16^{th}$ dimension: virtual 3D data of patient, obtained, for example from a scan or intraoperative measurements
$17^{th}$-$19^{th}$ dimension: vascular flow; in 1, 2 or 3 dimensions, e.g. in relationship to surgical field, organ or head including head motion
$20^{th}$-$22^{nd}$ dimension: temperature map (including changes induced by cryo- or hyperthermia), thermal imaging, in 1, 2 or 3 dimensions, e.g. in relationship to surgical field
$25^{th}$-$28^{th}$ dimension: metabolic map (e.g. using MRS, PET-CT, SPECT-CT), in 1, 2 or 3 dimensions, e.g. in relationship to surgical field
$29^{th}$-$32^{nd}$ dimension: functional map (e.g. using fMRI, PET-CT, SPECT-CT, PET, kinematic imaging), in 1, 2 or 3 dimensions, e.g. in relationship to surgical field or patient
$33^{rd}$-$35^{th}$ dimension: confocal imaging data and/or microscopy data in 1, 2, or 3 dimensions, e.g. in relationship to surgical field or patient, e.g. obtained through an endoscope or arthroscope or dental scanner or direct visualization/imaging of an exposed surface
$36^{th}$-$38^{th}$ dimension: optical imaging data in 1, 2 or 3 dimensions, e.g. in relationship to surgical field or patient, e.g. obtained through an endoscope or arthroscope or dental scanner or direct visualization/imaging of an exposed surface
$39^{th}$-$40^{th}$ dimension: laser scan data in 1, 2 or 3 dimensions, e.g. in relationship to surgical field or patient, e.g. obtained through an endoscope or arthroscope or dental scanner or direct visualization/imaging of an exposed surface Any oblique planes are possible. Any perspective projections are possible. Any oblique angles are possible. Any curved planes are possible. Any curved perspective projections are possible. Any combination of 1D, 2D, and 3D data between the different types of data is possible. Any of the virtual data or virtual representations for display by one or more HMDs in Table 4 or described in the specification can be adjusted with regard to the focal plane or focal point of the display using any of the embodiments described in the specification.

One or more computer processors can be integrated into, attached to or separate to one or more HMD, one or more surgical helmet, one or more external computer servers. A first computer processor can process data from one or more cameras for eye tracking. A second computer processor can activate one or more electromagnetic, electric, piezoelectric actuators and/or motors, for example for moving an HMD in relationship to a surgical helmet. A third computer processor can receive tracking information, e.g. from one or more video cameras or a surgical navigation system. A fourth computer processor can activate and/or control a robot, e.g. a handheld robot or a robot with a robotic arm. The first, second, third, fourth, fifth etc. computer processor can be the same or different. The first, second, third, fourth, fifth etc. computer processor can be integrated or attached to the HMD, the surgical helmet, or a computer or server separate from the HMD or surgical helmet. The computer processors can optionally be connected using an RF, WIFI, Bluetooth or LiFi signal. The computer processors can optionally be connected to a camera, an IMU, an eye tracking system, a navigation system, a surgical robot using an RF, WIFI, Bluetooth or LiFi signal.

Surgical Helmets

In some embodiments, the surgical helmet can include one or more of the following portions or modules or components:

Frontal or front facing portion, module or component
Parietal portion, module or component
Occipital portion, module or component
Temporal portion, module or component
Vertex portion, module or component
Zygomatic portion, module or component
Nasal portion, module or component
Maxillary portion, module or component
Mandibular portion, module or component
Chin portion, module or component Any of the frontal, parietal, occipital, temporal, vertex, zygomatic, nasal, maxillary, mandibular and/or chin portions, modules or components can include a skin, face or hair facing surface, portion, module or component and/or an external facing surface, portion, module or component. One or more of the frontal, parietal, occipital, temporal, vertex, zygomatic, nasal, maxillary, mandibular and/or chin portions, modules or components, including any skin, face or hair facing surfaces, portions, modules or components and/or external facing surfaces, portions, modules or components can be of mono-component design, e.g. with a singular body, or multi-component design, e.g. with multiple bodies, for example connected using mechanical, electric, magnetic or electromagnetic means and/or motors and/or actuators. Mono-component, singular body and multi-component, multi-body designs can be combined. For example, an internal (towards skin, face or hair) facing portion of a frontal, vertex and occipital portion can be of mono-component design, e.g. formed as a singular body, while a mandibular portion and chin portion can be of multi-component design with a chin portion body and two or more mandibular portion bodies formed as multiple bodies that can be connected to each other and, optionally, that can be connected to the single body frontal, vertex and occipital portion. Any combination of mono-component and multi-component designs is possible.

One or more of the frontal, parietal, occipital, temporal, vertex, zygomatic, nasal, maxillary, mandibular and/or chin portions, modules or components, including any skin, face or hair facing surfaces, portions, modules or components, can include one or more components, pieces, extenders, tabs to support, secure and/or stabilize the surgical helmet against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more fasteners, including optionally with adhesive, e.g. water soluble, to support, secure and/or stabilize the surgical helmet against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more straps, including optionally with rubber or Velcro, to support, secure and/or stabilize the surgical helmet against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more mechanical means to support, secure and/or stabilize the surgical helmet against portions of the surgeon's skin, hair, face on the surgeon's frontal, parietal, occipital, temporal, vertex, zygomatic, nasal, maxillary, mandibular and/or chin area.

The surgical helmet can include an optional fan, for example located near the occipital portion of the surgical helmet. Representative examples can be found, for example, in U.S. Pat. Nos. 6,481,019, 7,752,682, 8,819,869, and Patent Application Nos. US2012/0075464A1 and WO201460149A2, which are hereby incorporated by reference in their entireties.

The surgical helmet can include an optional air filtration system, for example with a vent or an air intake located near the frontal portion of the surgical helmet or extending near a transparent facial shield, which can, for example, be part of a cover for the surgical helmet or hood or a surgical gown. Representative examples can be found, for example, in U.S. Pat. Nos. 5,054,480, 6,481,019, 7,752,682, 8,819,869, and Patent Application Nos. US2012/0075464A1 and WO201460149A2, which are hereby incorporated by reference in their entireties.

In some embodiments, the air processed through the air filtration system can be exposed to an ultraviolet light source for purposes of reducing or killing any pathogens in the air that the surgeon is breathing. Representative examples can be found, for example, in U.S. Pat. Nos. 6,481,019, 7,752, 682, 8,819,869, and Patent Application Nos. US2012/0075464A1 and WO201460149A2, which are hereby incorporated by reference in their entireties.

In some embodiments, the air processed through the air filtration system can be exposed to an ultrasound transmitter for purposes of reducing or killing any pathogens in the air that the surgeon is breathing. The ultrasound transmitter can, for example, emit ultrasonic waves at a frequency ranging, for example, between 50 kHz and 10 MHz through air passing through the air filtration system. For example, the ultrasound transmitter can optionally be placed in front of the air intake of a fan or at the air exit from the fan. The ultrasound transmitter can also be placed near an air intake near the face shield.

Head Mounted Display Components

In some embodiments, the HMD can include one or more of the following portions or modules or components:
Frontal or front facing portion, module or component (18, FIGS. 1, 2A)
Clear or transparent front portion or visor (10, FIG. 1)
Parietal portion, module or component (20, FIGS. 1, 2A)
Occipital portion, module or component (22, FIGS. 1, 2A)
Temporal portion, module or component
Vertex portion, module or component
Zygomatic portion, module or component
Nasal portion, module or component, e.g. with nasal pads (15, FIGS. 1, 2A)
Maxillary portion, module or component
Mandibular portion, module or component
Chin portion, module or component
A head holder portion (24, FIG. 2A)
Any of the frontal, parietal, occipital, temporal, vertex, zygomatic, nasal, maxillary, mandibular and/or chin portions, modules or components can include a skin, face or hair facing surface, portion, module or component and/or an external facing surface, portion, module or component. One or more of the frontal, parietal, occipital, temporal, vertex, zygomatic, nasal, maxillary, mandibular and/or chin portions, modules or components, including any skin, face or hair facing surfaces, portions, modules or components and/or external facing surfaces, portions, modules or components can be of mono-component design, e.g. with a singular body, or multi-component design, e.g. with multiple bodies, for example connected using mechanical, electric, magnetic or electromagnetic means. Mono-component, singular body and multi-component, multi-body designs can be combined. For example, an internal (towards skin, face or hair) facing portion of a frontal, vertex and occipital portion can be of mono-component design, e.g. formed as a singular body, while a mandibular portion and chin portion can be of multi-component design with a chin portion body and two or more mandibular portion bodies formed as multiple bodies that can be connected to each other and, optionally, that can be connected to the single body frontal, vertex and occipital portion. Any combination of mono-component and multi-component designs is possible.

One or more of the frontal, parietal, occipital, temporal, vertex, zygomatic, nasal, maxillary, mandibular and/or chin portions, modules or components, including any skin, face or hair facing surfaces, portions, modules or components, can include one or more components, pieces, extenders, tabs to support, secure and/or stabilize the HMD against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more fasteners, including optionally with adhesive, e.g. water soluble, to support, secure and/or stabilize the HMD against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more straps, including optionally with rubber or Velcro, to support, secure and/or stabilize the HMD against portions of the surgeon's skin, hair, face on the surgeon's frontal, parietal, occipital, temporal, vertex, zygomatic, nasal, maxillary, mandibular and/or chin area.

One or more of the frontal, parietal, occipital, temporal, vertex, zygomatic, nasal, maxillary, mandibular and/or chin portions, modules or components, including any skin, face or hair facing surfaces, portions, modules or components, can include one or more mechanical means to support, secure and/or stabilize the HMD against portions of the surgeon's skin, hair, face on the surgeon's frontal, parietal, occipital, temporal, vertex, zygomatic, nasal, maxillary, mandibular and/or chin area. The mechanical means can be head holder which can optionally be tightened over the user's head, for example using a dial with expandable or retractable elements (24, FIG. 2A).

The frontal or front facing portion, module or component (18, FIGS. 1, 2A), parietal portion, module or component (20, FIGS. 1, 2A), occipital portion, module or component (22, FIGS. 1, 2A) can optionally include at least one processor, camera, depth sensor, storage media. The front portion or visor (11, FIG. 2A), for example centered over or located over the eyes, can be transparent, e.g. in the case of an optical see through head mounted display, or can be opaque or non-transparent, e.g. in the case of a video see through head mounted display.

Gown

In some embodiments, the surgeon can wear a surgical gown, which can be sterile. Standard surgical gowns, such as, for example, the AAMI Level 4 and Level 3 gowns provided by Cardinal Health (Dublin, OH, USA) can be used. The gown can, for example, cover the arms, shoulders, chest, abdomen, and/or back portions of the surgeon. The gown can be worn in conjunction with a cover for the surgical helmet or hood.

Cover for Surgical Helmet, Hood

In some embodiments, the surgeon can elect to wear a cover for a surgical helmet or hood, for example in conjunction with a surgical helmet and an optional air filtration system. The cover for the surgical helmet or hood can be sterile. The cover for the surgical helmet or hood can be made of the same material or a similar material as the gown. The cover for the surgical helmet or hood can cover the entire head and, optionally, extend down to the surgeon's neck and/or shoulders. The cover for the surgical helmet or hood can, optionally, be connected to the gown, for example using fasteners, Velcro straps, regular straps (which can, optionally, be tied or knotted). The cover for the surgical helmet or hood can include a transparent portion, e.g. an integrated, transparent face shield, through which the surgeon can observe the surgical field. The transparent portion, e.g. a transparent face shield, can be made of plastic. The transparent face shield can, optionally, include a UV light filter. The UV light filter function can be inherent to the plastic of the face shield. The UV light filter function can be achieved through a coating to the face shield. Optionally, the transparent portion, e.g. transparent face shield, can be exchangeable. Exchanging the transparent portion can be desirable when, for example, too much blood or tissue has accumulated on the transparent portion, for example after sawing a bone. The transparent portion can be exchangeable using mechanical means, e.g. one or more snap-on mechanisms, which can be rounded and local, e.g. like multiple snap-on studding the front portion of the cover for the surgical helmet or hood at the perimeter surrounding the face shield. The transparent portion can be exchangeable using a zip lock like mechanism, which can optionally surround the entire perimeter of the cover for the surgical helmet or hood portion framing the transparent portion. The transparent portion can be exchangeable using a zipper like mechanism, which can optionally surround the entire perimeter of the cover for the surgical helmet or hood portion framing the transparent portion.

The cover for surgical a helmet or hood can include visual and/or mechanical means for aligning the cover for the surgical helmet or hood with the surgical helmet. The cover for the surgical helmet or hood, transparent portion, e.g. transparent face shield, and/or the surgical helmet can include visual or mechanical means for aligning the HMD with the cover for the surgical helmet or hood, face shield, and/or the surgical helmet. The helmet, cover for the surgical helmet or hood, transparent portion, e.g. transparent face shield and/or the surgical helmet can also be aligned with the HMD, for example if the surgeon places the HMD first on his or her head.

The visual means in any of the embodiments can include aiming marks, e.g. on the cover for the surgical helmet or hood, transparent portion, e.g. transparent face shield, and/or the surgical helmet and/or the HMD. The aiming marks can be lines, circles, points, triangles, arrows or any other geometric shape or form. The aiming marks can deploy colors, e.g. red, green, yellow, blue etc. Each component can have one or more aiming marks, optionally with a corresponding aiming mark on the other component. For example, the HMD can have an aiming mark, with a corresponding aiming mark on the surgical helmet, so that the user can align the corresponding aiming marks and/or then, for example, physically connect the HMD and the surgical helmet, for example using a mechanical connector, e.g. a snap-on, ratchet, or dovetail like mechanism, e.g. with male and female parts. The surgical helmet can have an aiming mark, with a corresponding aiming mark on the transparent portion, e.g. transparent face shield, so that the user can align the corresponding aiming marks and then, for example, align and/or physically connect the transparent portion, e.g. transparent face shield, and the surgical helmet, for example using a mechanical connector, e.g. a snap-on, ratchet, or dovetail like mechanism, e.g. with male and female parts. The HMD can have an aiming mark, with a corresponding aiming mark on a transparent portion, e.g. transparent face shield, so that the user can align the corresponding aiming marks and then, for example, align and/or physically connect the HMD and the transparent portion, e.g. transparent face shield, for example using a mechanical connector, e.g. a snap-on, ratchet, or dovetail like mechanism, e.g. with male and female parts.

Fiducial markers can have an aiming mark, with a corresponding aiming mark on the surgical helmet, so that the user can align the corresponding aiming marks and/or then, for example, align and/or physically connect the fiducial markers, e.g. on an arm or extender, and the surgical helmet, for example using a mechanical connector, e.g. a snap-on, ratchet, or dovetail like mechanism, e.g. with male and female parts. Fiducial markers can have an aiming mark, with a corresponding aiming mark on the HMD, so that the user can align the corresponding aiming marks and then, for example, align and/or physically connect the fiducial markers, e.g. on an arm or extender, and the HMD, for example using a mechanical connector, e.g. a snap-on, ratchet, or dovetail like mechanism, e.g. with male and female parts. Fiducial markers can have an aiming mark, with a corresponding aiming mark on the transparent portion, e.g. transparent face shield, so that the user can align the corresponding aiming marks and then, for example, align and/or physically connect the fiducial markers, e.g. on an arm or extender, and the face shield, for example using a mechanical connector, e.g. a snap-on, ratchet, or dovetail like mechanism, e.g. with male and female parts.

Fiducial markers can have an aiming mark, with a corresponding aiming mark on the surgical helmet and/or the HMD and/or the transparent portion, e.g. transparent face shield, so that the user can align the corresponding aiming marks and/or then, for example, align and/or physically connect the fiducial markers, e.g. on an arm or extender, and the surgical helmet and/or the HMD and/or the transparent portion of the cover, e.g. transparent face shield, for example using a mechanical connector, e.g. a snap-on, ratchet, or dovetail like mechanism, e.g. with male and female parts.

The mechanical means or mechanical connectors can be, in any part of the specification, for example, mechanical connectors, e.g. snap-on mechanisms, ratchet like mechanisms, e.g. wherein a female part can engage with a male part, e.g. on the cover for the surgical helmet or hood, transparent portion, e.g. transparent face shield, surgical helmet, one or more fiducial markers, including any fiducial markers mounted onto holding structures or arms or fixtures, and/or the HMD, dovetail like mechanisms, e.g. on the cover for the surgical helmet or hood, face shield, surgical helmet, one or more fiducial markers, including any fiducial markers mounted onto holding structures or arms or fixtures, and/or the HMD.

Transparent Portion, e.g. Transparent Face Shield

The transparent portion of the cover, e.g. transparent face shield, can have dimensions that can be less than, approximately the same, or greater than the facial dimensions of the user. The transparent portion, e.g. transparent face shield, can have dimensions that can be less than, approximately the same, or greater than the field of view of the user. The transparent portion, e.g. transparent face shield, can have dimensions that can be less than, approximately the same, or greater than the field of view of the HMD. The transparent portion, e.g. transparent face shield, can be made of plastic. The transparent portion, e.g. transparent face shield, can be transparent, partially transparent or semi-transparent. The transparent portion, e.g. transparent face shield, can include a UV light filter, e.g. integrated into the plastic or, for example, applied as a coating.

In some embodiments, a HMD can be integrated into a surgical helmet or can be attached to a surgical helmet, e.g. using one or more mechanical connectors. The surgical helmet can have an integrated fan also.

One or more fiducial markers can be attached to or integrated into a surgical helmet.

One or more fiducial markers can be mounted on one or more holding arms or holding members attached to an HMD and/or a surgical helmet and/or a transparent portion, e.g. transparent face shield, which can optionally extend to or extend through the cover for the surgical helmet or hood (for example, if the cover for the surgical helmet or hood includes some holes or openings through which the holding arms or holding members can pass through the cover for the surgical helmet or hood to the outward facing side of the cover for the surgical helmet or hood).

The holding arm or member can include a magnet, optionally located subjacent to the cover for the surgical helmet or hood and/or external or superjacent to the cover for the surgical helmet or hood. A second holding arm or member with an optional second magnet can be placed over the first holding arm or member outside the cover for the surgical helmet or hood. The two magnets can attract each other, thereby fixing the second holding arm or member inside and/or outside the cover for the surgical helmet or hood in a fixed spatial relationship to the first holding arm or member and the HMD and/or the surgical helmet (for example, if the HMD is integrated into the surgical helmet or attached to the surgical helmet) and/or the transparent portion, e.g. transparent face shield. The second holding arm or member can include one or more fiducial markers, e.g. located outside the cover for the surgical helmet or hood and visible to the navigation, image capture or other registration system. Multiple holding arms or holding members can be used, e.g. a first, second, third, fourth, fifth and more holding arm. Using a first, second, third, fourth, fifth or more magnets, the first, second, third, fourth, fifth or more holding arm or holding members can be connected.

One or more magnets can be integrated into or attached to the portion of the holding arm subjacent to the cover for the surgical helmet. The base of the fiducial marker, or a holding arm with an integrated or attached fiducial marker, or the fiducial marker, external to the cover for the surgical helmet, can be made of metal.

One or more magnets can be integrated into or attached to the base of the fiducial marker, or a holding arm with an integrated or attached fiducial marker, or the fiducial marker, external to or superjacent to the cover for the surgical helmet. The holding arm subjacent to the cover for the surgical helmet can be made of metal.

One or more magnets can be integrated into or attached to the portion of the holding arm subjacent to the cover for the surgical helmet. One or more magnets can be integrated into or attached to the base of the fiducial marker, or a holding arm with an integrated or attached fiducial marker, or the fiducial marker, external to the cover for the surgical helmet.

One or more magnets can engage or couple with a second one or more magnets. One or more magnets can engage or couple with a metal.

In the foregoing embodiments, instead of a magnet, a lock, locking mechanism, an attachment, an attachment mechanism, mechanical means and/or mechanical connector connecting a first and second holding arm or member or a base of a fiducial marker or a fiducial marker can be used; in this embodiment, the first holding arm or member can extend through an optional hole in the cover for the surgical helmet or hood to allow for attaching, locking and/or connecting of the second holding arm or member with the attached fiducial marker or to allow for attaching, locking and/or connecting of the base of the fiducial marker or the fiducial marker. In any of the embodiments, a fiducial marker can be an optical marker, a geometric pattern, a bar code, a QR code, an alphanumeric code, a radiofrequency marker, an infrared marker, a retroreflective marker, an active marker, and a passive marker. Multiple holding arms or holding members can be used, e.g. a first, second, third, fourth, fifth and more holding arm. Using a first, second, third, fourth, fifth or more attachment, attachment mechanism, lock, locking mechanism, mechanical means and/or mechanical connector, the first, second, third, fourth, fifth or more holding arm or holding members can be connected or the first, second, third, fourth, fifth or more base of a fiducial marker or fiducial markers can be connected.

In another embodiment, one or more markers can be directly attached to the HMD, for example portions of the HMD not covered by the cover for the surgical helmet or hood, and/or visible through the transparent portion of the cover for the surgical helmet or hood. The markers can be active markers, e.g. LEDs emitting infrared or visible light for detection by the navigation, image capture or other registration system.

In another embodiment, fiducial markers can be mounted on one or more holding arms or holding members attached to the HMD and/or the surgical helmet, which can optionally extend to the clear see through portion or transparent portion of the cover for the surgical helmet or hood. The holding arm or member can include a magnet, optionally located subjacent to the clear see through portion or transparent portion of the cover for the surgical helmet or hood. A second holding arm or member with an optional second magnet can be placed over the first holding arm or member outside the clear see through portion or transparent portion of the cover for the surgical helmet or hood. The two magnets can attract each other, thereby fixing the second holding arm or member outside the clear see through portion of the cover for the surgical helmet or hood in a fixed spatial relationship to the first holding arm or member and the HMD and/or the surgical helmet (for example, if the HMD is integrated into the surgical helmet or attached to the surgical helmet). The second holding arm or member can include one or more fiducial markers, located outside the clear see through portion of the cover for the surgical helmet or hood and visible to the navigation, image capture or other registration system.

A base of a fiducial marker or a fiducial marker with an integrated or attached optional second magnet can be placed over the first holding arm or member outside the clear see through portion or transparent portion of the cover for the surgical helmet or hood. The two magnets can attract each other, thereby fixing the base of the fiducial marker or the fiducial marker outside the clear see through portion or transparent portion of the cover for the surgical helmet or hood in a fixed spatial relationship to the first holding arm or member and the HMD and/or the surgical helmet (for example, if the HMD is integrated into the surgical helmet or attached to the surgical helmet). The base of the fiducial marker or the fiducial marker can comprise one or more fiducial markers, located outside the clear see through portion or transparent portion of the cover for the surgical helmet or hood and visible to the navigation, image capture or other registration system. Multiple holding arms or holding members can be used, e.g. a first, second, third, fourth, fifth and more holding arm. Multiple bases or fiducial markers can be used, e.g. a first, second, third, fourth, fifth and more base or fiducial marker. Using a first, second, third, fourth, fifth or more magnets, the first, second, third, fourth, fifth or more holding arm or holding members can be connected. Using a first, second, third, fourth, fifth or more magnets, the first, second, third, fourth, fifth or more base or fiducial marker can be connected. Instead of a magnet, a lock, locking mechanism, an attachment, an attachment mechanism, mechanical means and/or mechanical connector connecting the first and second holding arms or members, or the base or fiducial marker, can be used; in this embodiment, the first holding arm or member can extend through an optional hole in the clear see through portion of the cover for the surgical helmet or hood to allow for attaching or locking of the second holding arm or member with the attached fiducial marker or for attaching or locking the base of the fiducial marker or the fiducial marker. Multiple holding arms or holding members can be used, e.g. a first, second, third, fourth, fifth and more holding arm. Using a first, second, third, fourth, fifth or more attachment, attachment mechanism, lock, locking mechanism, mechanical means and/or mechanical connector, the first, second, third, fourth, fifth or more holding arm or holding members can be connected or attached or the first, second, third, fourth, fifth or more bases of fiducial markers or fiducial markers can be connected or attached.

In another embodiment, an HMD can be attached to a surgical helmet. The attachment can be permanent. The attachment can be a removable connection. The surgical helmet can have an integrated fan also. The fiducial markers can be attached to or integrated into the surgical helmet and/or the HMD. The fiducial markers can be mounted on one or more holding arms or holding members or holding fixtures or bases attached to the helmet and/or the HMD, which can optionally extend to the cover for the surgical helmet or hood. The holding arm or member can include a magnet, optionally located subjacent to the cover for the surgical helmet or hood. A second holding arm or member with an optional second magnet can be placed over the first holding arm or member outside the cover for the surgical helmet or hood. The two magnets can attract each other, thereby fixing the second holding arm or member, or base or fiducial marker, inside and/or outside the cover for the surgical helmet or hood in a fixed spatial relationship to the first holding arm or member and the surgical helmet and/or the HMD. The second holding arm or member, or base or fiducial marker, can include one or more fiducial markers, located outside the cover for the surgical helmet or hood and visible to the navigation, image capture or other registration system. Multiple holding arms or holding members, or bases or fiducial markers, can be used, e.g. a first, second, third, fourth, fifth and more holding arm, or base or fiducial marker. Using a first, second, third, fourth, fifth or more magnets, the first, second, third, fourth, fifth or more holding arm or holding members or bases or fiducial markers can be connected. Thus, in any of the embodiments throughout the specification, multiple fiducial markers and multiple holding arms or holding members or holding fixtures for fiducial markers or bases for fiducial markers or fiducial markers can be used.

Since the HMD can be attached or integrated in this and other embodiments to the surgical helmet or since the surgical helmet can be attached or integrated to the HMD in this and other embodiments, the spatial coordinates of the HMD in relationship to the helmet can be known; thus, a coordinate transfer can be used to track the HMD in its relationship to the one or more fiducial markers attached to the helmet; a coordinate transfer can be used to track the surgical helmet in its relationship to the one or more fiducial markers attached to the HMD; a coordinate transfer can be used to track the HMD in its relationship to the one or more fiducial markers attached to the surgical helmet. Instead of a magnet, an attachment, an attachment mechanism, a lock, locking mechanism, mechanical means and/or mechanical connector connecting the first and second holding arms or members or bases of fiducial markers or fiducial markers can be used; in this embodiment, the first holding arm or member can extend through an optional hole in the cover for the surgical helmet or hood to allow for attaching or locking of the second holding arm or member with the attached fiducial marker or for attaching or locking of the base of the fiducial marker or of the fiducial marker.

In some embodiments, the HMD can be an integral part of a surgical helmet. In some embodiments, the surgical helmet can be an integral part of the HMD.

Adjusting Mechanism for HMD

The attachment of the HMD to the surgical helmet can be adjustable, for example, using an adjusting mechanism, e.g. a dial, knob, button, lever, slider, handle, handle bar, thread, ratchet, screw, ring, key, wrench or combinations thereof, to adjust for different facial and head shape of different users. The adjustment mechanism can be mechanical, electric, electromagnetic, piezoelectric etc. The amount of adjustment in x, y, and/or z-direction can be determined, e.g. on an attached scale, and can optionally be included in the coordinates of the HMD in relationship to the surgical helmet to which it is attached and any fiducial markers attached to the helmet. This can be, for example, useful when the HMD is attached to, coupled to, or connected to the surgical helmet and one or more markers, e.g. fiducial markers are also connected to the surgical helmet.

Alternatively, at least one marker, e.g. via a holding member attaching and/or coupling the marker, can be connected and/or attached to the HMD; in this case, the HMD can be directly referenced/registered relative to the attached marker, irrespective of any adjustments of the position of the HMD, e.g. up, down, forward, backward and/or rotation/tilt to adjust the HMD position in relationship to the user's eyes and, optionally, a transparent portion of a cover for the surgical helmet.

The adjusting mechanism can be configured to provide a forward or backward movement of the HMD in relationship to the user's face or eyes. The adjusting mechanism can be configured to provide an upward or downward movement of the HMD in relationship to the user's face or eyes. The adjusting mechanism can be configured to provide a tilting of the HMD in relationship to the user's face or eyes. The adjusting mechanism can be configured to provide a rotation of the HMD in relationship to the user's face or eyes, e.g. in a frontal (coronal) plane and/or in a sagittal plane. The adjusting mechanism can be configured to center the HMD and/or the display of the virtual data in relationship to the surgeon's eyes and/or the surgeon's visual field. The adjusting mechanism can be operated prior to the surgery to adjust the position (including a forward-backward, up-down movement, orientation adjustment, e.g. rotation, tilt) of the HMD. The adjusting mechanism can be operated during the surgery to adjust the position (including the orientation, rotation, tilt) of the HMD, e.g. by the surgeon or a nurse. In some embodiments, at least portions of the adjusting mechanism, e.g. a dial, knob, button, lever, slider, handle, handle bar, thread, ratchet, screw, ring, key, wrench or combinations thereof, can be subjacent to the cover for the surgical helmet and can be operated through the cover of the surgical helmet. In some embodiments, at least portions of the adjusting mechanism, e.g. a dial, knob, button, lever, slider, handle, handle bar, thread, ratchet, screw, ring, key, wrench or combinations thereof, can extend external to the cover for the surgical helmet and can be touched directly, without interposed cover for the surgical helmet. In the latter embodiment, at least portions of the adjusting mechanism, e.g. a dial, knob, button, lever, slider, handle, handle bar, thread, ratchet, screw, ring, key, wrench or combinations thereof can optionally provided sterile.

In some embodiments, the adjusting mechanism can include at least one magnet. The at least one magnet can couple at least portions of the adjusting mechanism, e.g. a dial, knob, button, lever, slider, handle, handle bar, thread, ratchet, screw, ring, key, wrench or combinations thereof external or superjacent to the cover for the surgical helmet with at least portions of the adjusting mechanism located subjacent to the cover for the surgical helmet. The at least portions of the adjusting mechanism, e.g. a dial, knob, button, lever, slider, handle, handle bar, thread, ratchet, screw, ring, key, wrench or combinations thereof external or superjacent to the cover for the surgical helmet can be provided sterile.

In some embodiments, the adjusting mechanism can be electric, electromagnetic, or piezoelectric and the position of the HMD (including forward-backward, up-down movement, orientation adjustment, e.g. rotation, tilt) can be adjusted using a computer processor and a user interface, as described in the specification or known in the art. In some embodiments, the adjusting mechanism can be electric, electromagnetic, e.g. using a motor, or piezoelectric and the position of the HMD (including forward-backward, up-down movement, orientation adjustment, e.g. rotation, tilt) can be adjusted automatically using a computer processor and, optionally, eye tracking as described in the specification or known in the art.

Adjusting Mechanism for Camera

If a computer processor operates a camera (21, FIG. 1) integrated into or attached to the HMD, e.g. for inside-out-tracking, an adjusting mechanism can be configured to provide a forward or backward movement of the camera, e.g. in relationship to the HMD, the surgical helmet, and/or the user's eyes or face. The adjusting mechanism can be configured to provide an upward or downward movement of the camera, e.g. in relationship to the HMD, the surgical helmet, and/or the user's eyes or face. The adjusting mechanism can be configured to provide a tilting of the camera, e.g. in relationship to the HMD, the surgical helmet, and/or the user's eyes or face. The adjusting mechanism can be configured to provide a rotation of the camera, e.g. in relationship to the HMD, the surgical helmet, and/or the user's eyes or face, e.g. in a frontal (coronal) plane and/or in a sagittal plane.

The adjusting mechanism can be configured to center the camera, e.g. in relationship to the HMD, the surgical helmet, and/or the user's eyes or face and/or the surgeon's visual field. The adjusting mechanism can be operated prior to the surgery to adjust the position (including a forward-backward, up-down movement, orientation adjustment, e.g. rotation, tilt) of the camera. The adjusting mechanism can be operated during the surgery to adjust the position (including the orientation, rotation, tilt) of the camera, e.g. by the surgeon or a nurse. In some embodiments, at least portions of the adjusting mechanism, e.g. a dial, knob, button, lever, slider, handle, handle bar, thread, ratchet, screw, ring, key, wrench or combinations thereof, can be subjacent to the cover for the surgical helmet and can be operated through the cover of the surgical helmet. In some embodiments, at least portions of the adjusting mechanism, e.g. a dial, knob, button, lever, slider, handle, handle bar, thread, ratchet, screw, ring, key, wrench or combinations thereof, can extend external to the cover for the surgical helmet and can be touched directly, without interposed cover for the surgical helmet. In the latter embodiment, at least portions of the adjusting mechanism, e.g. a dial, knob, button, lever, slider, handle, handle bar, thread, ratchet, screw, ring, key, wrench or combinations thereof can optionally provided sterile.

In some embodiments, the adjusting mechanism can include at least one magnet. The at least one magnet can couple at least portions of the adjusting mechanism, e.g. a dial, knob, button, lever, slider, handle, handle bar, thread, ratchet, screw, ring, key, wrench or combinations thereof external or superjacent to the cover for the surgical helmet with at least portions of the adjusting mechanism located subjacent to the cover for the surgical helmet. The at least portions of the adjusting mechanism, e.g. a dial, knob, button, lever, slider, handle, handle bar, thread, ratchet, screw, ring, key, wrench or combinations thereof external or superjacent to the cover for the surgical helmet can be provided sterile.

In some embodiments, the adjusting mechanism can be electric, electromagnetic, or piezoelectric and the position of the camera (including forward-backward, up-down movement, orientation adjustment, e.g. rotation, tilt) can be adjusted using a computer processor and a user interface, as described in the specification or known in the art. In some embodiments, the adjusting mechanism can be electric, electromagnetic, e.g. using a motor, or piezoelectric and the position of the camera (including forward-backward, up-down movement, orientation adjustment, e.g. rotation, tilt) can be adjusted automatically using a computer processor and, optionally, eye tracking as described in the specification or known in the art.

Adjusting Mechanism for Surgical Helmet

The attachment of the surgical helmet to the HMD can be adjustable, for example, using an adjusting mechanism, e.g. a dial, knob, button, lever, slider, handle, handle bar, thread, ratchet, screw, ring, key, wrench or combinations thereof, to adjust for different facial and head shape of different users. The adjustment mechanism can be mechanical, electric, electromagnetic, piezoelectric etc. The amount of adjustment in x, y, and/or z-direction can be determined, e.g. on an attached scale, and can be included in the coordinates of the HMD in relationship to the surgical helmet to which it is attached and the fiducial markers attached to the helmet. This can be, for example, useful when the HMD is attached to, coupled to, or connected to the surgical helmet and one or more markers, e.g. fiducial markers are also connected to the surgical helmet. Alternatively, at least one marker, e.g. via a holding member attaching and/or coupling the marker, can be connected and/or attached to the HMD; in this case, the HMD can be directly referenced/registered relative to the attached marker, irrespective of any adjustments of the position of the HMD, e.g. up, down, forward, backward and/or rotation/tilt to adjust the HMD position in relationship to the user's eyes and, optionally, a transparent portion of a cover for the surgical helmet.

The adjusting mechanism can be configured to provide a forward or backward movement of the surgical helmet in relationship to the user's face or eyes and/or the HMD. The adjusting mechanism can be configured to provide an upward or downward movement of the surgical helmet in relationship to the user's face or eyes and/or the HMD. The adjusting mechanism can be configured to provide a tilting of the surgical helmet in relationship to the user's face or eyes and/or the HMD. The adjusting mechanism can be configured to provide a rotation of the surgical helmet in relationship to the user's face or eyes and/or the HMD, e.g. in a frontal (coronal) plane and/or in a sagittal plane.

The adjusting mechanism can be configured to center surgical helmet in relationship to the surgeon's eyes and/or the surgeon's visual field and/or the HMD. The adjusting mechanism can be operated prior to the surgery to adjust the position (including a forward-backward, up-down movement, orientation adjustment, e.g. rotation, tilt) of the surgical helmet. The adjusting mechanism can be operated during the surgery to adjust the position (including the orientation, rotation, tilt) of the surgical helmet, e.g. by the surgeon or a nurse. In some embodiments, at least portions of the adjusting mechanism, e.g. a dial, knob, button, lever, slider, handle, handle bar, thread, ratchet, screw, ring, key, wrench or combinations thereof, can be subjacent to the cover for the surgical helmet and can be operated through the cover of the surgical helmet. In some embodiments, at least portions of the adjusting mechanism, e.g. a dial, knob, button, lever, slider, handle, handle bar, thread, ratchet, screw, ring, key, wrench or combinations thereof, can extend external to the cover for the surgical helmet and can be touched directly, without interposed cover for the surgical helmet. In the latter embodiment, at least portions of the adjusting mechanism, e.g. a dial, knob, button, lever, slider, handle, handle bar, thread, ratchet, screw, ring, key, wrench or combinations thereof can optionally provided sterile.

In some embodiments, the adjusting mechanism can include at least one magnet. The at least one magnet can couple at least portions of the adjusting mechanism, e.g. a dial, knob, button, lever, slider, handle, handle bar, thread, ratchet, screw, ring, key, wrench or combinations thereof external or superjacent to the cover for the surgical helmet with at least portions of the adjusting mechanism located subjacent to the cover for the surgical helmet. The at least portions of the adjusting mechanism, e.g. a dial, knob, button, lever, slider, handle, handle bar, thread, ratchet, screw, ring, key, wrench or combinations thereof external or superjacent to the cover for the surgical helmet can be provided sterile.

In some embodiments, the adjusting mechanism can be electric, electromagnetic, or piezoelectric and the position of the surgical helmet (including forward-backward, up-down movement, orientation adjustment, e.g. rotation, tilt) can be adjusted using a computer processor and a user interface, as described in the specification or known in the art. In some embodiments, the adjusting mechanism can be electric, electromagnetic, e.g. using a motor, or piezoelectric and the position of the surgical helmet (including forward-backward, up-down movement, orientation adjustment, e.g. rotation, tilt) can be adjusted automatically using a computer processor and, optionally, eye tracking as described in the specification or known in the art.

In some embodiments, the system can comprise a head mounted display; and an adjusting mechanism, wherein the head mounted display can be configured to be worn on a head of a user under a cover of a surgical helmet so that the display of the head mounted display can be adjacent to a transparent portion of the cover, wherein the adjusting mechanism can be configured to adjust at least a position of the head mounted display in relationship to the user's eyes; wherein the system can comprise a connecting mechanism configured to couple the head mounted display to the surgical helmet. The adjusting mechanism can comprise the connecting mechanism. The adjusting mechanism can be configured to adjust the head mounted display in relationship to the user's eyes in an x, a y, or a z-direction or combinations thereof. The adjustment of the head mounted display can comprise a translation of about 30 mm, about 25 mm, about 20 mm, about 15 mm, about 10 mm, about 7 mm, about 5 mm, about 4 mm, about 3 mm, about 2 mm, about 1 mm, about 0.5 mm, about 0.25 mm in at least one of an x, a y, or a z-direction or combinations thereof. The adjusting mechanism can be configured to rotate, tilt or rotate and tilt the head mounted display in relationship to at least one of the user's eyes. The rotating or tilting or rotating and tilting the head mounted display can comprise a change in angular orientation of about 30°, about 25°, about 20°, about 15°, about 10°, about 9°, about 8°, about 7°, about 6°, about 5°, about 4°, about 3°, about 2°, about 1°, about 0.5°, about 0.25° in at least one direction. The adjusting mechanism can be configured for adjusting the position of the head mounted display prior to a surgical procedure or during the surgical procedure or prior to and during the surgical procedure. The adjusting mechanism can comprise a mechanical mechanism configured to adjust the position of the head mounted display. The mechanical mechanism can comprise one or more mechanical elements, wherein the one or more mechanical element can comprise a dial, knob, button, lever, slider, handle, handle bar, ring, key, wrench or combinations thereof. The mechanical mechanism can comprise one or more mechanical elements configured to be subjacent to the cover for the surgical helmet, and wherein the mechanical element can be configured to be operated through the cover for the surgical helmet. The mechanical mechanism can comprise one or more mechanical elements configured to be operated external to the cover for the surgical helmet. The mechanical element external to the cover for the surgical helmet can be provided sterile. The adjusting mechanism can comprise a motorized element, an electric element, an electromagnetic element, a piezoelectric element or combinations thereof configured to adjust the position of the head mounted display. The system can comprise a processor and a user interface, wherein the user interface can be configured to activate the motorized element, the electric element, the electromagnetic element, the piezoelectric element or combinations thereof, wherein the user interface can comprise a graphical user interface, a voice recognition, a gesture recognition, a virtual interface displayed by the head mounted display, a virtual keyboard displayed by the head mounted display, a virtual slider, a virtual button, an eye tracking system, a physical keyboard, a physical computer mouse, a physical button, a physical joy stick, a physical track pad, or a combination thereof. The system can comprise a processor and an eye tracking system, wherein the processor can be configured to receive one or more inputs from the eye tracking system and to generate one or more outputs for activating the motorized element, the electric element, the electromagnetic element, the piezoelectric element or combinations thereof for adjusting the position of the head mounted display. The eye tracking system can comprise at least one camera configured to be integrated into or attached to the head mounted display or the surgical helmet, wherein the at least one camera can be configured to track at least one eye of the user.

The surgical procedure can comprise a knee replacement, hip replacement, shoulder joint replacement, ankle joint replacement, or a spinal procedure. The connecting mechanism can be configured to be attachable to the surgical helmet. The connecting mechanism can be configured to be integrated into the surgical helmet. The connecting mechanism can be configured to be attachable to the head mounted display. The connecting mechanism can be configured to be integrated into the head mounted display. The connecting mechanism can be configured to be integrated into a portion of a housing of the head mounted display. The connecting mechanism can be configured to attach the head mounted display to the surgical helmet. The at least head mounted display can be an optical see through head mounted display. The at least one head mounted display can be a video see through head mounted display.

In some embodiments, the system can comprise a head mounted display, at least one holding member, at least one marker, and at least one magnetic coupling mechanism, wherein the at least one holding member can be configured to be integrated into or configured to be attached to the head mounted display, wherein the at least one magnetic coupling mechanism is configured to removably attach the at least one marker to the at least one holding member. Each of the at least one holding member can comprise a proximal and a distal end, wherein the proximal end of the holding member can be attached to the head mounted display, and wherein the at least one marker can be attached to the distal end of the holding member. The at least one holding member can be attached directly to the head mounted display. The at least one holding member can be attached indirectly to the head mounted display. The at least one magnetic coupling mechanism can comprise at least one magnetic element, and wherein the at least one magnetic element can be positioned at the distal end of the at least one holding member. The at least one magnetic element can be attached to the distal end of the at least one holding member, to the at least one marker or to the distal end of the at least one holding member and to the at least one marker. The at least one magnetic coupling mechanism can comprise a first magnetic element attached to the distal end of the at least one holding member and a second magnetic element attached to the to the at least one marker. At least one holding member can be configured to be removably attached to the head mounted display. The head mounted display can be configured to be worn under a cover of a surgical helmet by a user. The holding member can be configured to extend subjacent to a cover for a surgical helmet, and wherein the at least one marker can be configured to be attached to the at least one holding member superjacent to the cover for the surgical helmet. The processor can be configured to register the head mounted display in a coordinate system using the at least one marker. The processor can be integrated into the head mounted display. The processor can be external to the head mounted display. The holding member can be composed of at least one of a metal, plastic, magnetic material, or combinations thereof. The holding member can be rigid. The at least one marker can be part of a marker structure, wherein the marker structure can comprise two or more markers, wherein the two or more markers can be arranged in a geometrically predetermined orientation. The at least one magnetic coupling mechanism can be configured to position the at least one marker in a geometrically predetermined position and orientation relative to the head mounted display. The at least one marker can be configured to be mounted in a geometrically predetermined position and orientation with an accuracy of about 2 mm, about 1.5 mm, about 1 mm, about 0.5 mm, about 0.25 mm, about 0.1 mm, about 0.05 mm in at least one direction, or an accuracy of about 2°, about 1.5°, about 1°, about 0.5°, about 0.25°, about 0.1°, about 0.05° in at least one direction. The at least one magnetic coupling mechanism can comprise one or more neodymium magnets or other magnets. The at least one marker, the at least one holding member, the at least one magnetic coupling mechanism, or combinations thereof can comprise one or more mating features, wherein the one or more mating features can be configured to position the at least one marker in a geometrically predetermined position and orientation relative to the head mounted display. The predetermined position and orientation can be adjusted for a thickness of the cover for the surgical helmet. At least a portion of the holding member can be provided sterile. At least one marker can be provided sterile. At least one holding member can be configured to be integrated into, attached to or linked to the surgical helmet. The least one marker can comprise at least one of an optical marker, a geometric pattern, a bar code, a QR code, an alphanumeric code, a radiofrequency marker, an infrared marker, a retroreflective marker, an active marker, and a passive marker. The at least one holding member can be configured to be removably connected to the head mounted display using at least one magnetic mechanism, a mechanical attachment mechanism, an electromagnetic attachment mechanism, or combinations thereof. The at least one holding member can be configured to be removably connected to the surgical helmet using at least one of a magnetic mechanism, a mechanical attachment mechanism, an electromagnetic attachment mechanism, or combinations thereof. The at least one marker can comprise a base, wherein the base is mounted on the distal end of the at least one holding member using the at least one magnetic element. The at least one magnetic element can be configured to be integrated into or attached to the at least one of the at least one marker, the base holding the at least one marker, the at least one holding member, the head mounted display, the surgical helmet, the cover for the surgical helmet or combinations thereof. The head mounted display can be an optical see through head mounted display. The head mounted display can be a video see through head mounted display. The system can be configured to track the head mounted display during a surgical procedure. The system can use an outside in tracking. The system can use an inside out tracking. The system can use an outside in and an inside out tracking.

In some embodiments, the system can track a head mounted display during a surgical procedure and can comprise a head mounted display; at least one marker; and at least one holding member, wherein the head mounted display can be configured to be integrated into or attached to a surgical helmet, wherein the at least one holding member can be integrated into or configured to be attached to or connected to the head mounted display, the surgical helmet or combinations thereof, wherein at least a portion of the at least one holding member can be configured to extend through at least one opening of a cover for the surgical helmet, wherein the at least one marker can be configured to be integrated into or attached to the at least one holding member external to the cover. The system can comprise a processor, wherein the processor can be configured to register the head mounted display in a coordinate system using the at least one marker. The processor can be integrated into the head mounted display. The processor can be external to the head mounted display. The system can be configured to track the head mounted display during a surgical procedure. The head mounted display can be configured to be integrated into or attached to the surgical helmet worn on a head of a user under the cover so that the display of the head mounted display can be adjacent to a transparent portion of the cover so as to permit the user to view the surgical site. The at least a portion of the holding member can be provided sterile. The at least the portion of the holding member that extends external of the cover for the surgical helmet can be provided sterile. The at least one marker can be provided sterile. The at least one holding member can be configured to be integrated into, attached to or connected to the surgical helmet. The least one marker comprises one or more optical marker, a geometric pattern, a bar code, a QR code, an alphanumeric code, a radiofrequency marker, an infrared marker, a retroreflective marker, an active marker, a passive marker, or combinations thereof. The at least one marker can be configured to be removably attached to the at least one holding member using a magnetic mechanism, a mechanical attachment mechanism, an electromagnetic attachment mechanism, or combinations thereof. The at least one holding member can be configured to be removably attached to the head mounted display using a magnetic mechanism, a mechanical attachment mechanism, an electromagnetic attachment mechanism, or combinations thereof. The at least one holding member can be configured to be attached to the surgical helmet using a magnetic mechanism, a mechanical attachment mechanism, an electromagnetic attachment mechanism, or combinations thereof. The at least one marker can comprise a base, wherein the base can be mounted on the at least one holding member. The head mounted display can be an optical see through head mounted display. The head mounted display can be a video see through head mounted display.

Figure 2A:
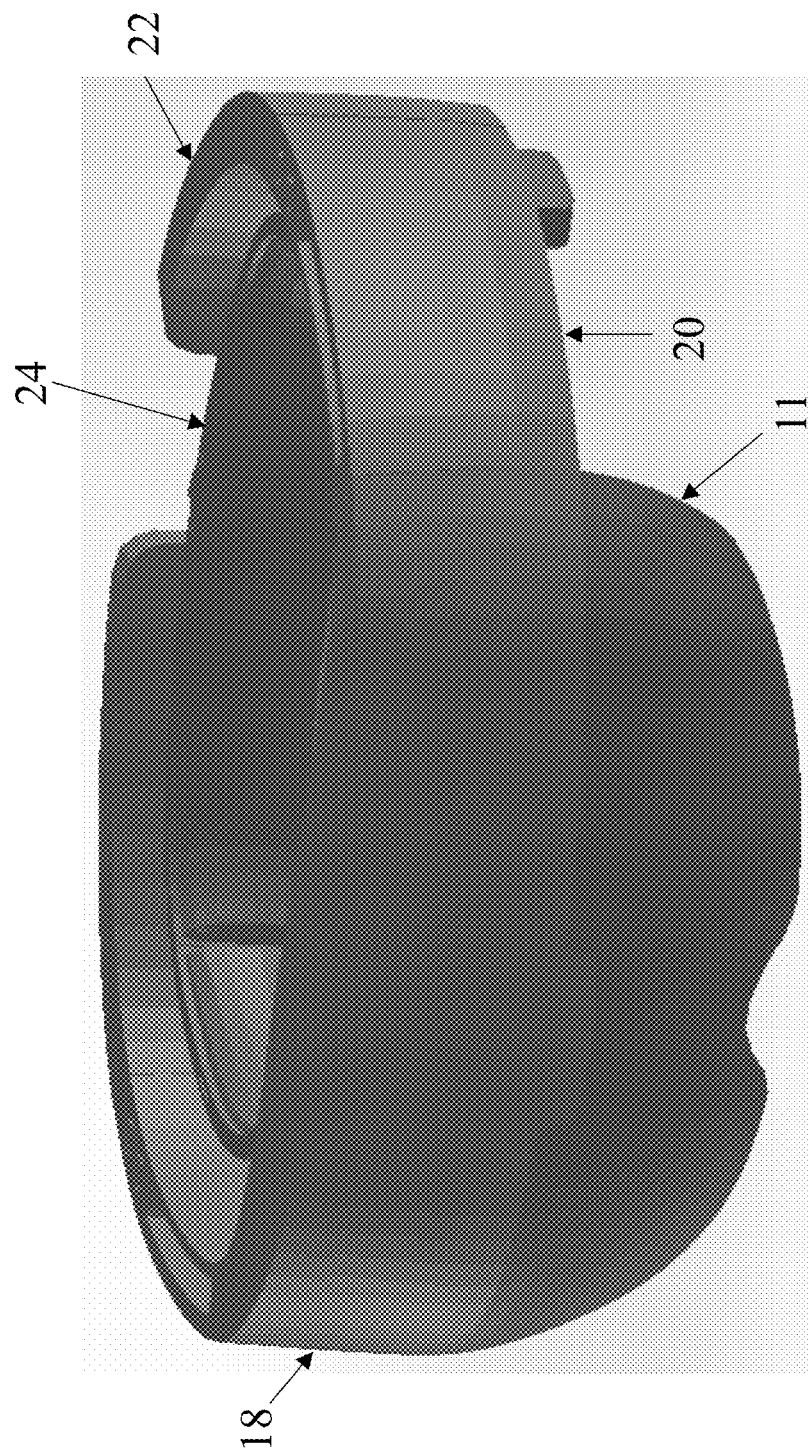
FIGS. 2A-2F are exemplary, non-limiting illustrations of head mounted displays showing various extenders, e.g. to a front portion or visor, with snap ons, fiducial markers, e.g. optical markers, infrared markers, RF markers, navigation markers, active markers, passive markers, etc according to some embodiments.
Figure 2B:
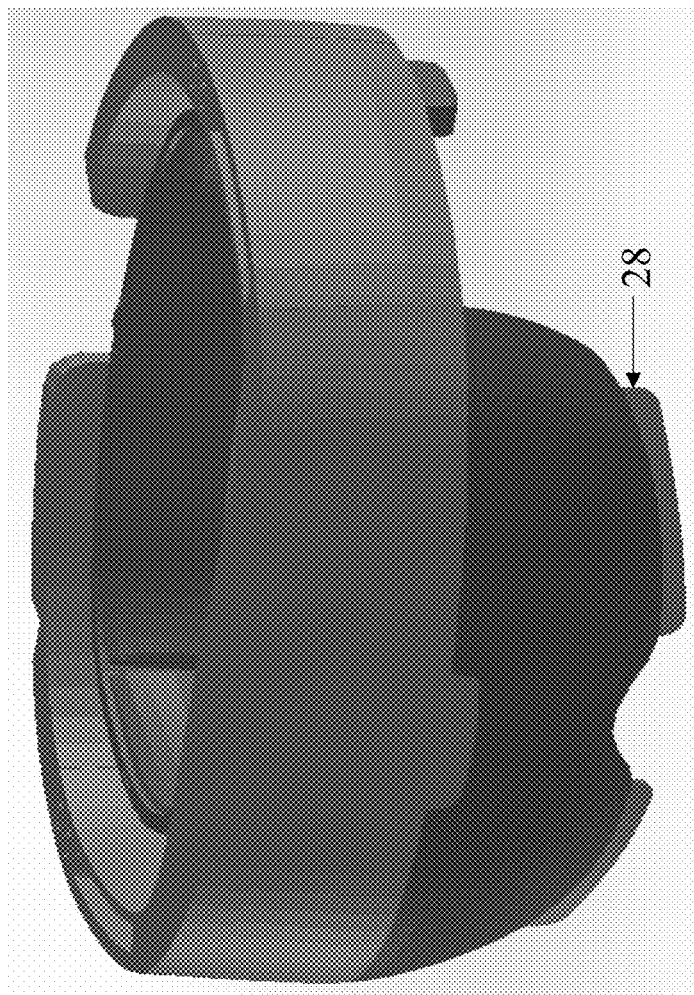
Figure 2C:
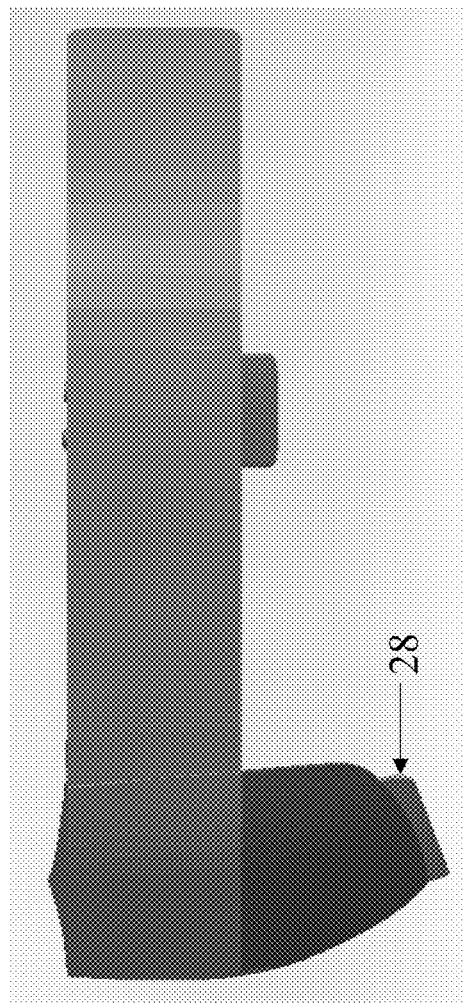
Figure 2D:
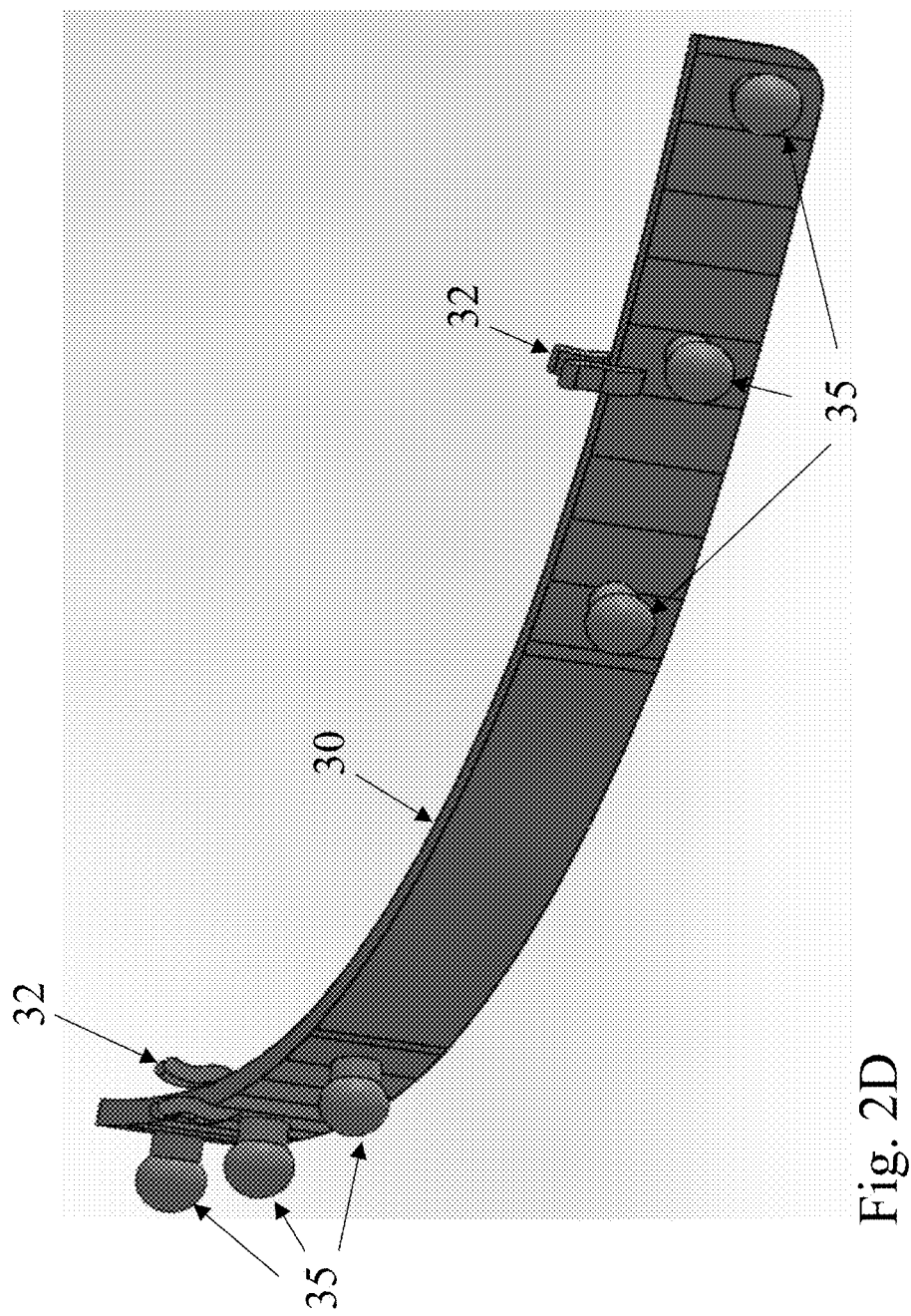
Figure 2E:
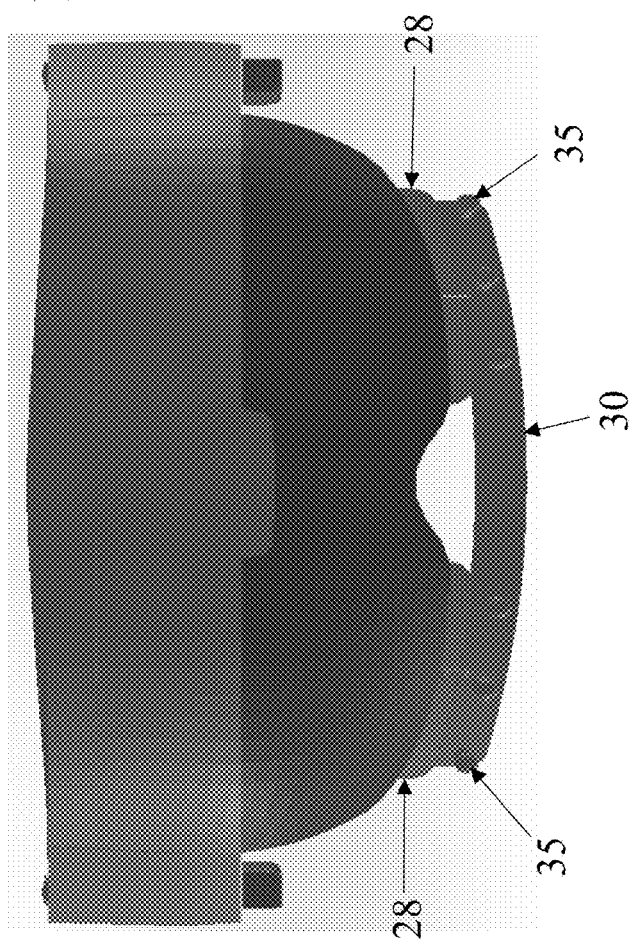
Figure 2F:
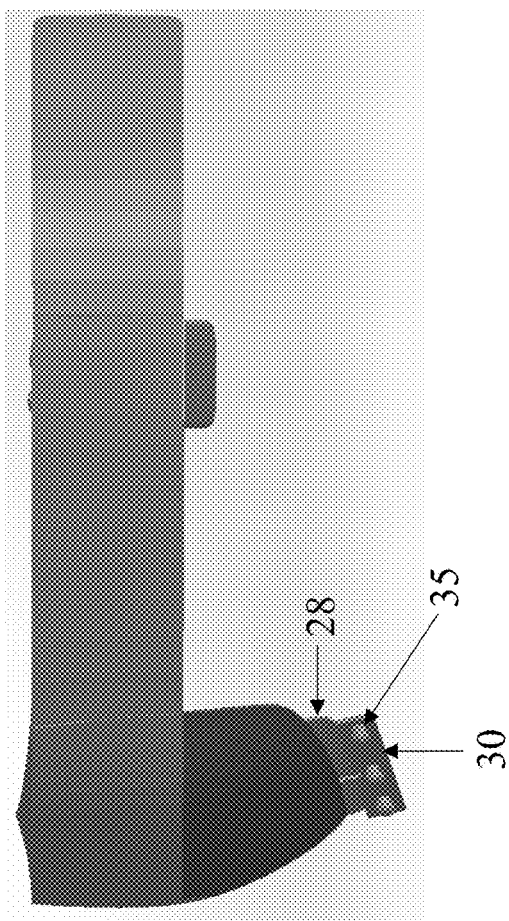

The following are additional non-limiting illustrative embodiments describing various aspects of the invention. FIG. 2A is an illustrative example of a head mounted display (HMD). The frontal or front facing portion, module or component 18, parietal portion, module or component 20, occipital portion, module or component 22 can optionally include at least one processor, camera, depth sensor, storage media. The front portion or visor 11, for example centered over or located over the eyes, can be transparent, e.g. in the case of an optical see through head mounted display, or can be opaque or non-transparent, e.g. in the case of a video see through head mounted display. The HMD can have extender tabs (grey) 28 (FIGS. 2B, 2C). Extender tabs 28 can be attachable and/or detachable. Extender tabs 28 can be used for attaching one or more fiducial markers and/or for attaching one or more holding arms, holding members or holding fixtures. FIG. 2D is an illustrative example of a snap on structure 30 with one or more snap on mechanisms 32 and one or more fiducial markers 35. The snap on can, for example, be attached to the extender tab(s) 28. FIGS. 2E, 2F show a fiducial marker 35 set attached to the HMD, in this example with extender tabs 28 and snap on 30 fiducial marker 35 set. By attaching the one or more fiducial markers 35 to the extender tabs 28 and/or one or more holding arms or holding members (not shown), the one or more fiducial markers 35 can be placed in an area that is not obscured by the cover for the surgical helmet or hood, but, for example, an area that is visible through the transparent portion of the cover, e.g. a transparent face shield. The transparent portion can be configured with regard to its dimensions, e.g. AP, ML, SI so that the fiducial markers 35 can be detected by a navigation system, image capture system, video system etc. through the transparent portion of the cover, e.g. a transparent face shield.

Figure 3A:
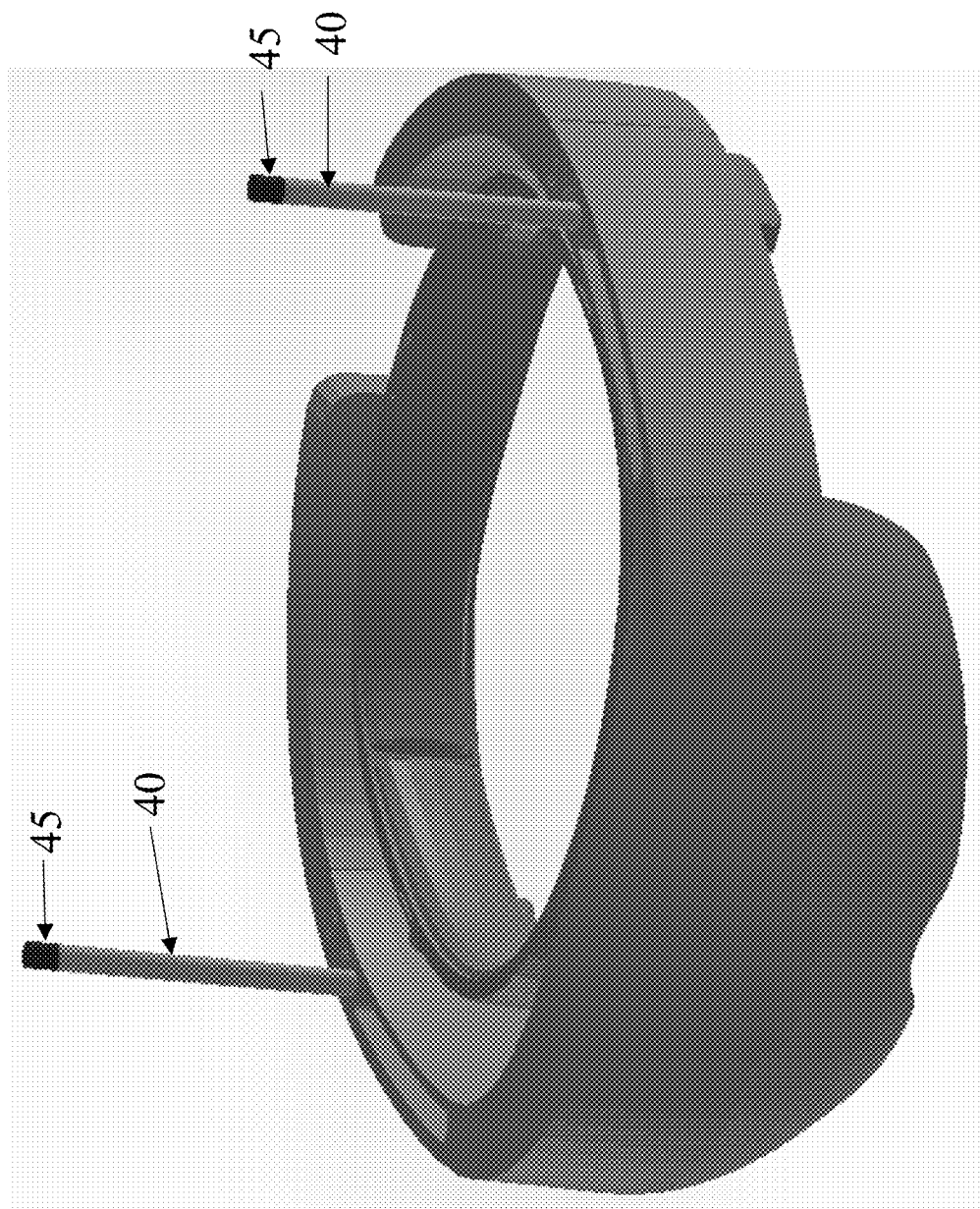
FIGS. 3A-3C show illustrative embodiments, where a holding member or holding arm or extender can be integrated or attached to an HMD, with optional use of magnets and/or mechanical connectors according to some embodiments.
Figure 3B:
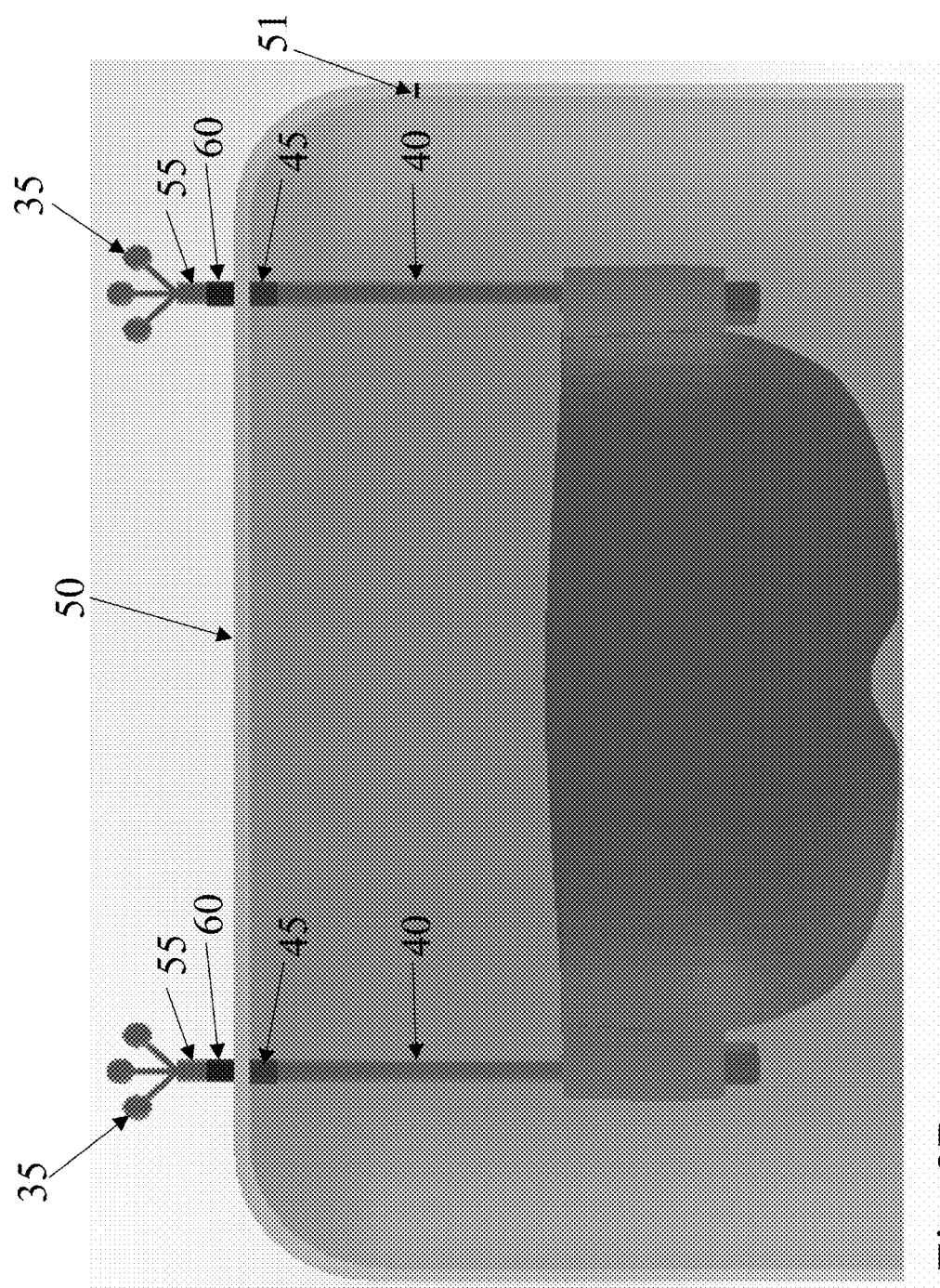
Figure 3C:
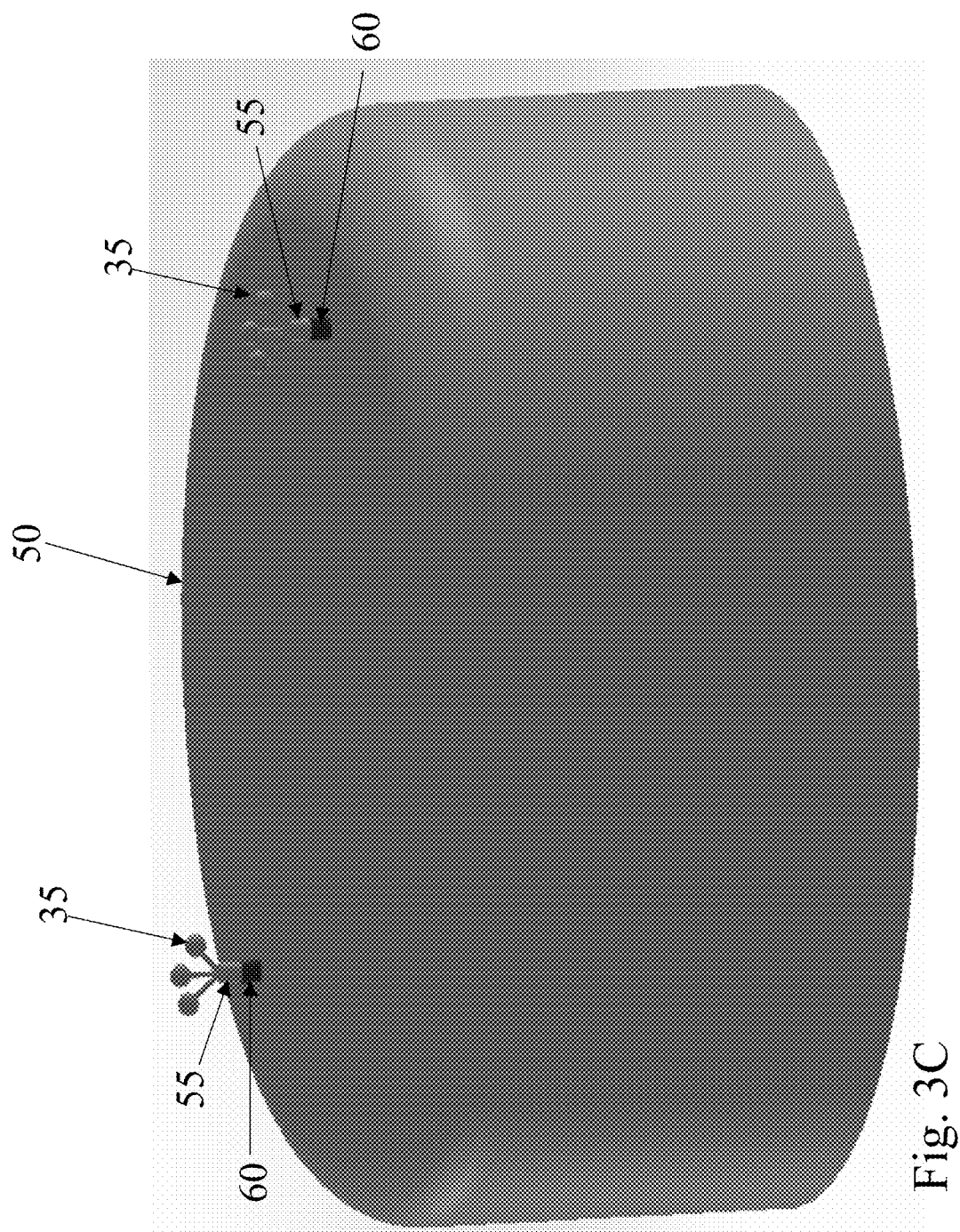

FIGS. 3A-C shows an illustrative embodiment, where a holding member 40 or holding arm 40 or extender 40 is integrated or attached to an HMD. The holding member 40 can comprise a mechanical connector or attachment at the end or, in the example in FIGS. 3A and 3B, a magnet or magnetic connector 45. The holding members can be configured to stay clear of the surgical helmet (not shown) on the surgeon's head or to connect to the surgical helmet or to connect to the HMD and the surgical helmet. The holding members 40 can optionally extend to/subjacent to the cover for the surgical helmet 50 or hood or through the cover for the surgical helmet or hood, if the cover for the surgical helmet or hood has openings to accommodate the posts.

In this example, after a cover for the surgical helmet or hood 50 is applied, one or more fiducial markers 35 attached to a second holding member 55 (or a base) with an optional second magnet 60 and/or a second mechanical connector can be connected to the holding member 40 connected to the HMD, with the cover 50 for the surgical helmet or hood interposed. In this example, three fiducial markers 35 are seen on the top left and three fiducial markers 35 are seen on the top right. A first mechanical connector can be of male type, a second mechanical connector can be of female type. The first mechanical connector can be of female type, the second mechanical connector can be of male type. The fiducial markers 35 can be in a predetermined position and/or orientation relative to the HMD using the one or more holding members 40, 55 (or bases) and the one or more magnets 45, 60. The predetermined position and orientation, and resultant coordinates of the HMD and/or the fiducial markers, can be adjusted for a thickness 51 of the cover for the surgical helmet; for example, the thickness of the cover can be added and/or subtracted to the relevant coordinates of the marker and/or the HMD and/or the surgical helmet.

In some embodiments, the magnets, for example as seen in FIG. 3B, can be substituted or supplemented by a male piece, for example connected or linked to the marker, the base of the marker or a holding member connected to the marker, and a female piece, for example linked, connected to, or integrated into the holding member attached to the HMD and/or the surgical helmet. The male piece can optionally be configured to comprise a sharp portion, wherein the user can utilize the sharp portion to pierce the cover for the surgical helmet and to advance the male portion to mate or connect with the female portion. The cover can optionally include at least one transparent portion in a location configured to visualize or make visible the female portion; in this manner, the user can advance the male portion with the sharp portion through the cover, piercing the cover, into the female portion under visual control. Alternatively, the user can palpate the female portion under the cover and advance the male portion with the sharp portion through the cover under tactile control.

Figures 4A, 4B, 4C:
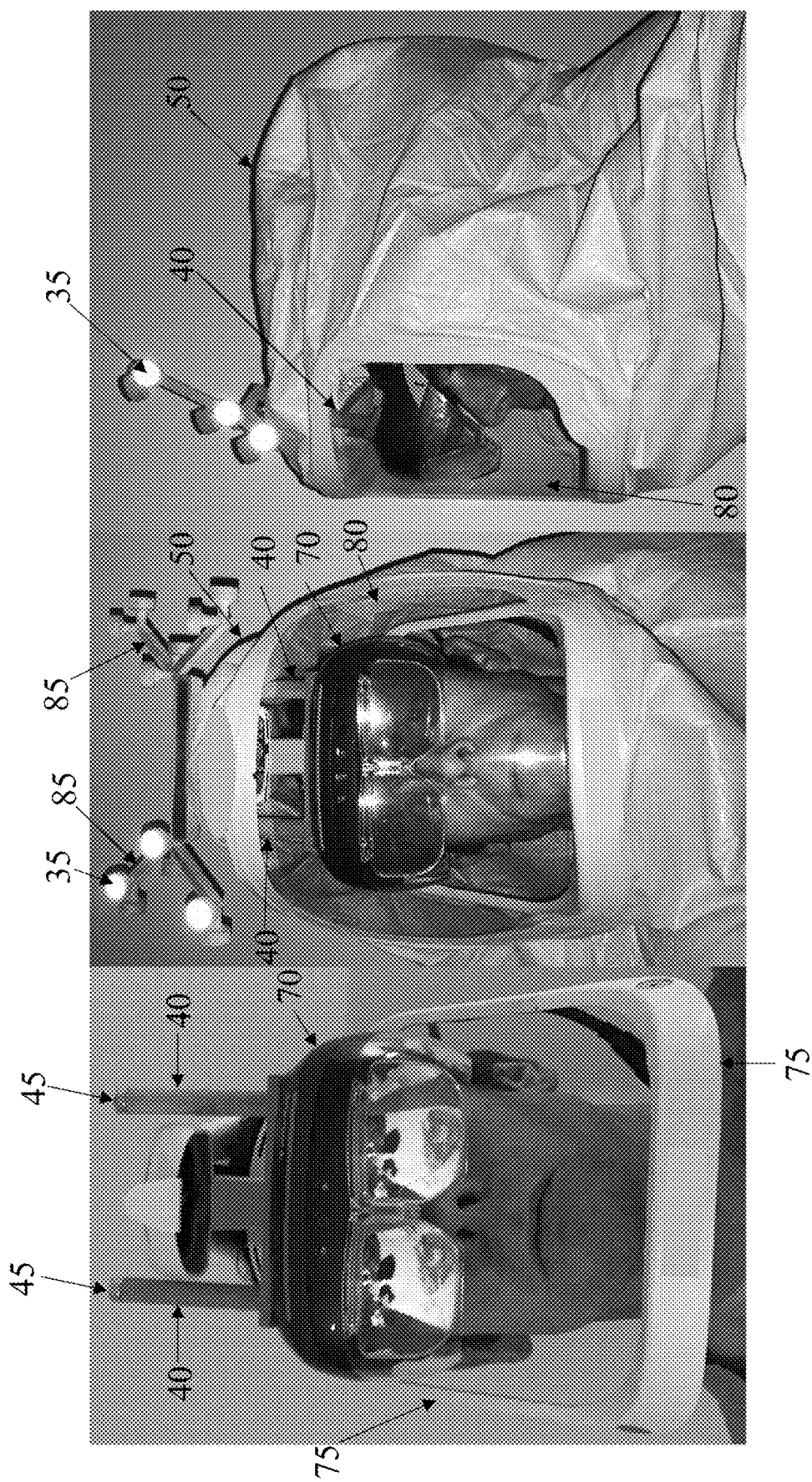
FIGS. 4A-4D are illustrative examples of an integration of an HMD with a surgical helmet, using, for example, one or more magnets according to some embodiments.
Figure 4D:
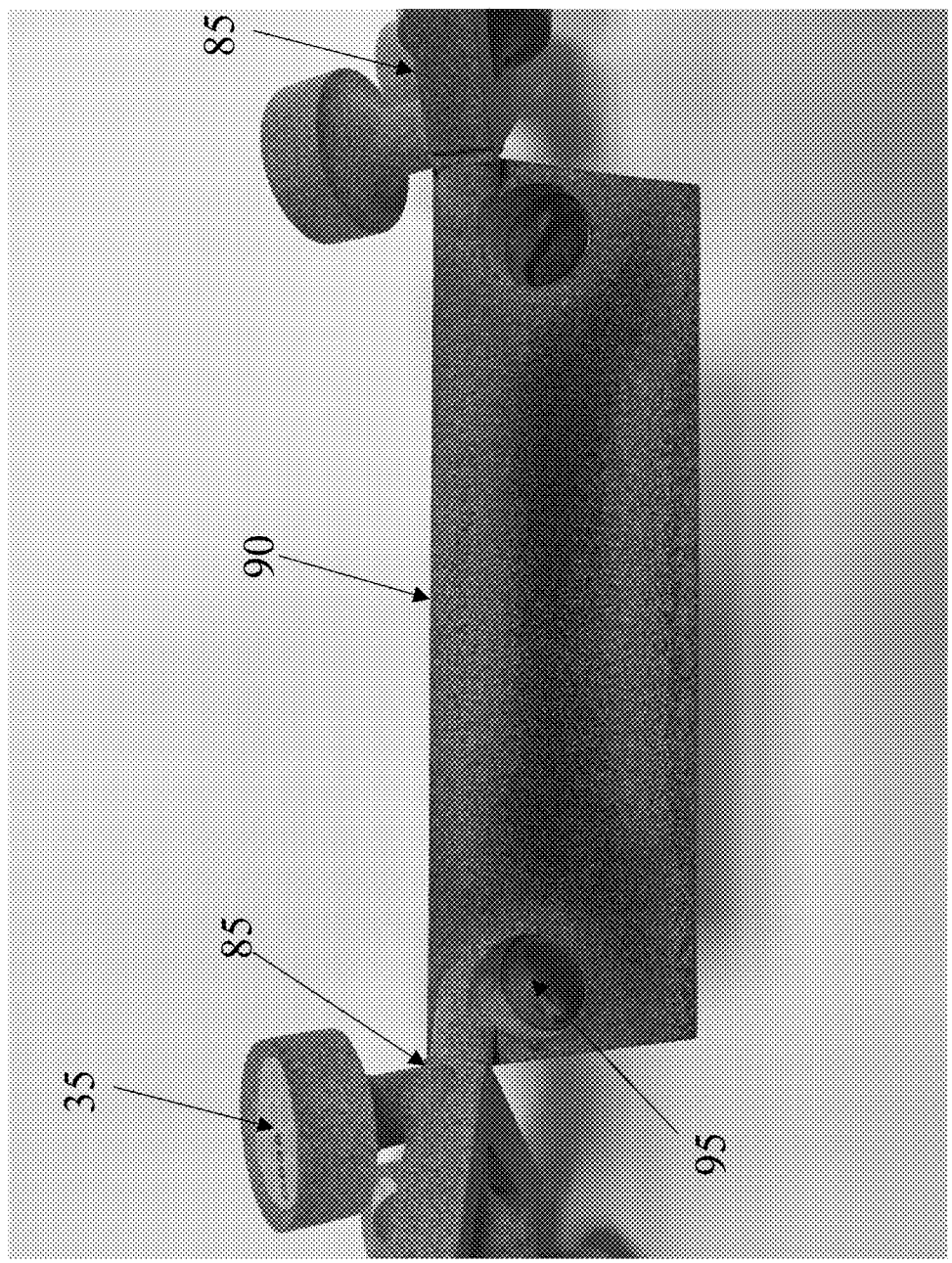
Figure 5A:
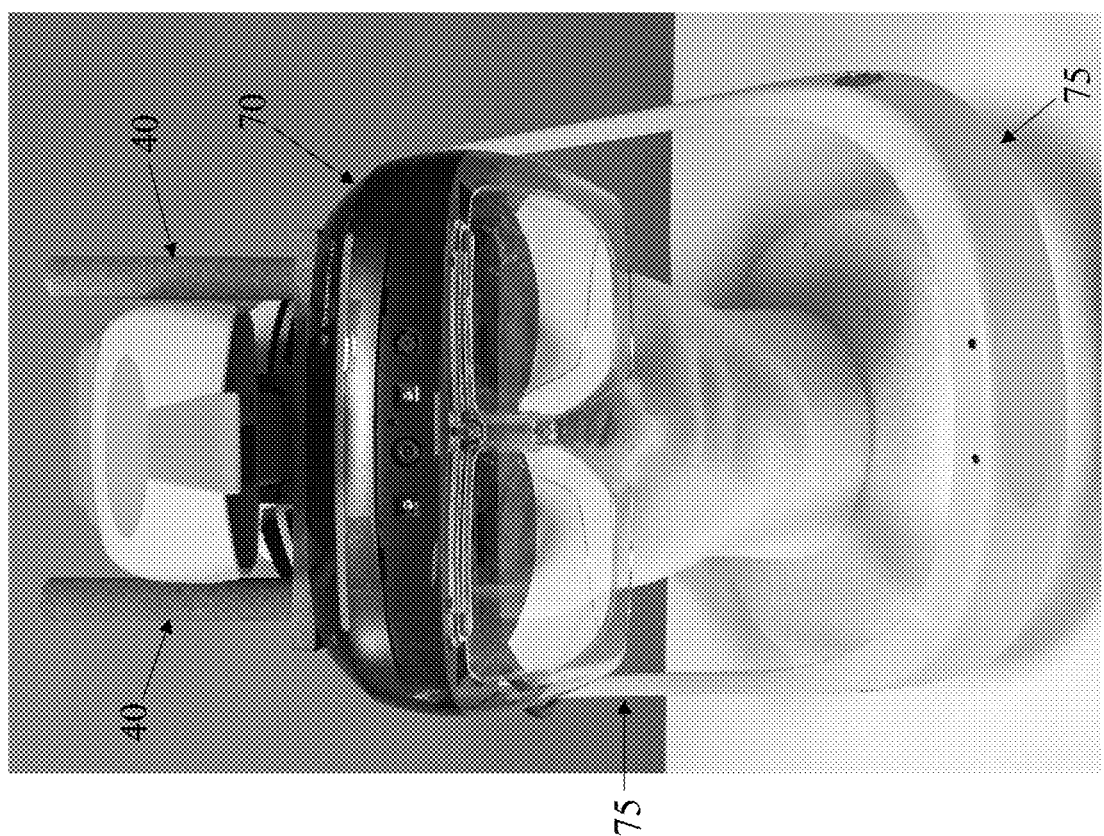
FIGS. 5A-5D are illustrative examples of an integration of an HMD with a surgical helmet, using, for example, a mechanical attachment or coupling mechanism or connection according to some embodiments.
Figure 5B:
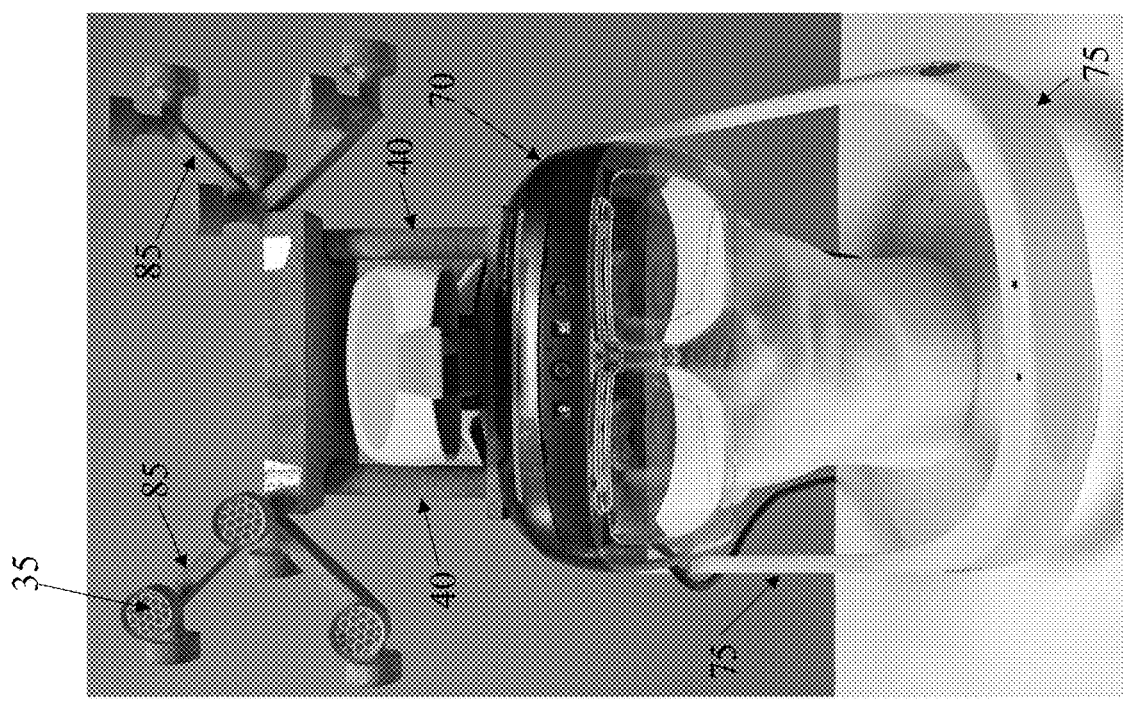
Figure 5C:
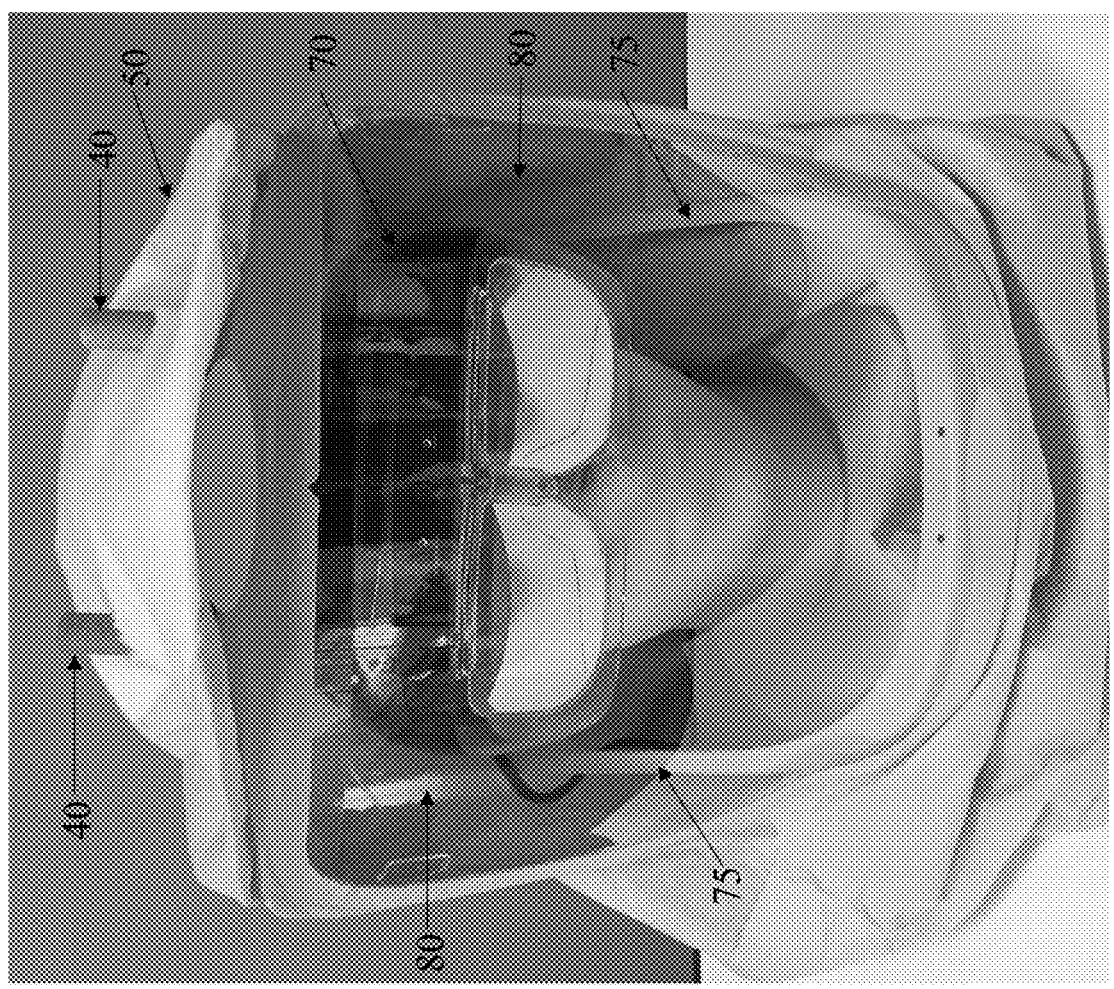
Figure 5D:
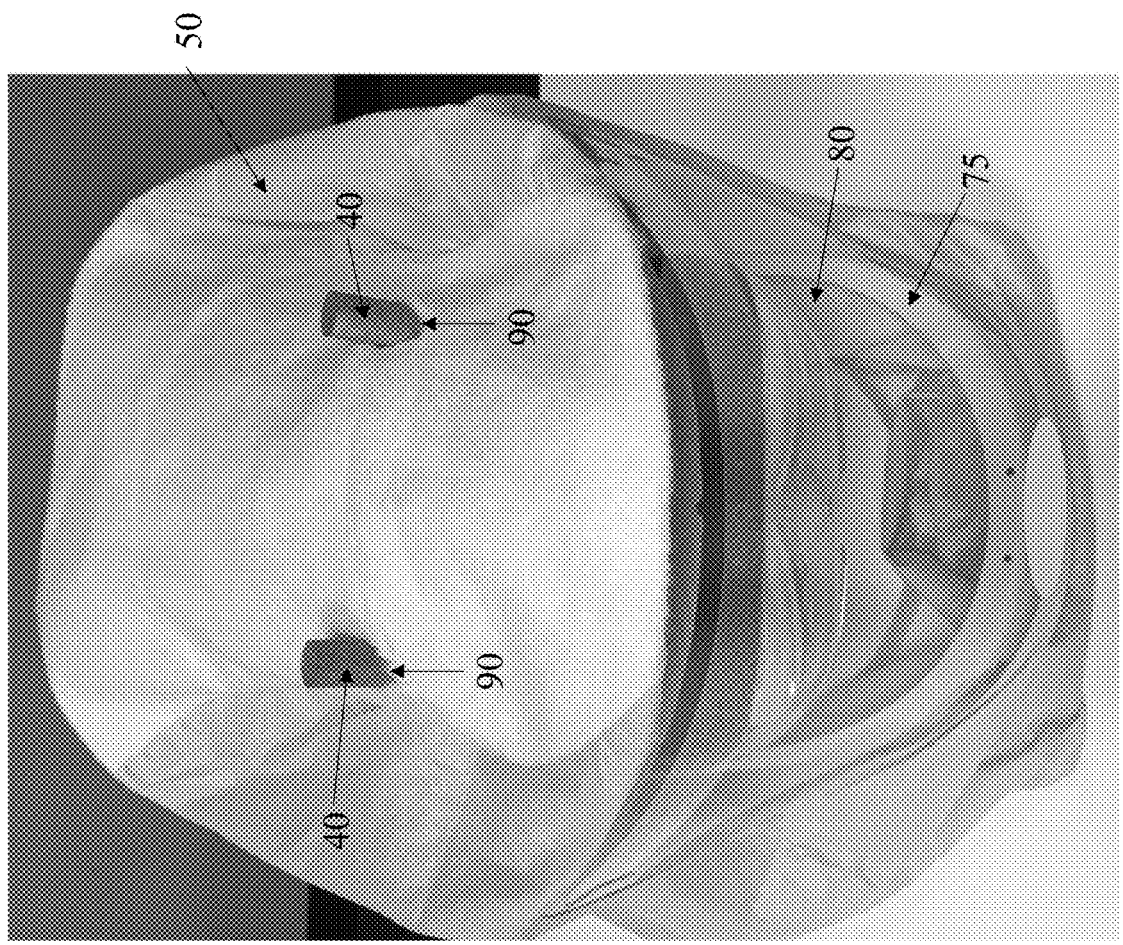
Figure 6A:
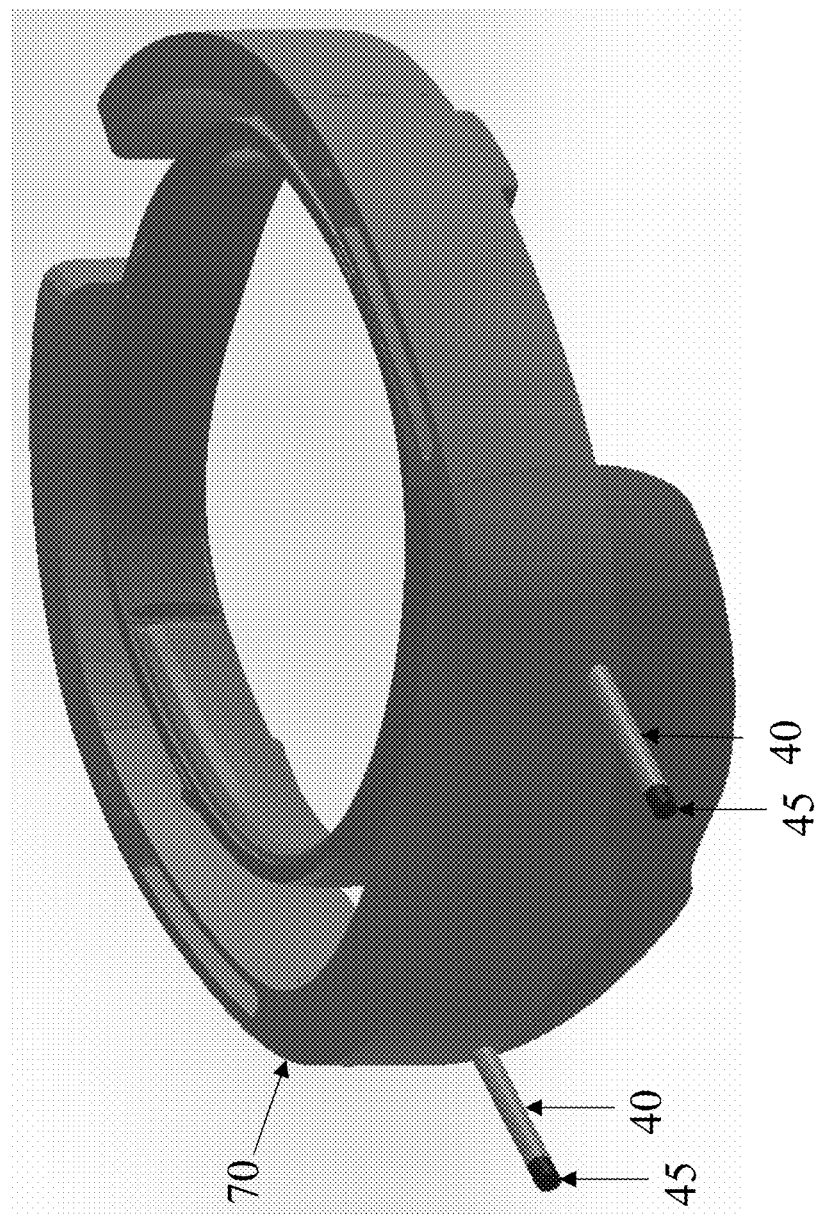
Figure 6D:
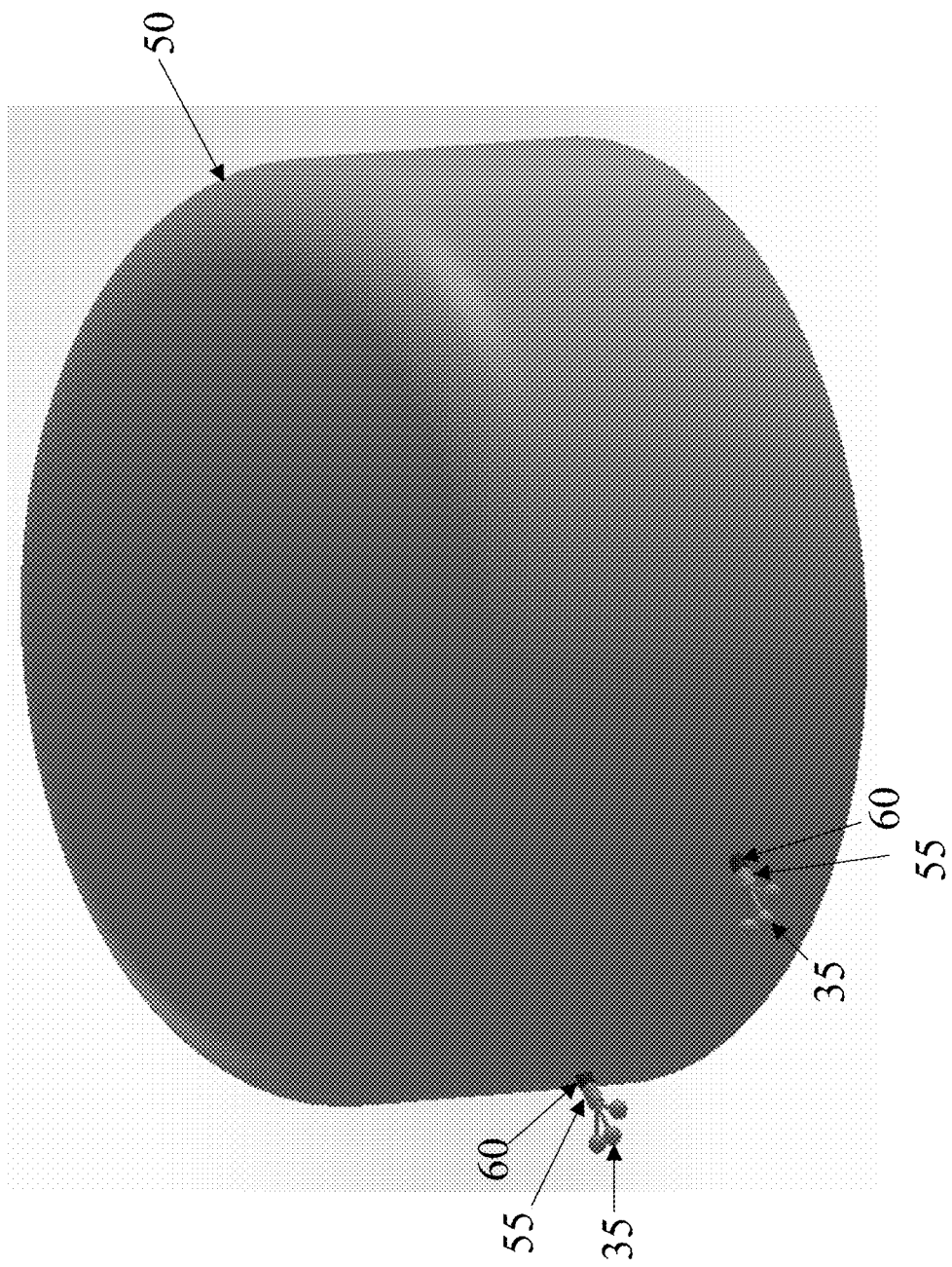

FIGS. 4A-D are illustrative examples of an integration of an HMD 70 with a surgical helmet 75. Surgical helmets can be used, for example, for joint replacement surgery. The HMD 70 can be mechanically, e.g. removably, attached to the frame of the surgical helmet 75. Two holding members 40 extend superiorly from the HMD 70, comprising magnets 45 at the superior tip. A cover 50 for the surgical helmet with a transparent portion 80 can be applied over the surgical helmet 75, and fiducial marker structure 85 with multiple fiducial markers 35 can be attached with use of optional mating magnets (not shown) attached to the base 90 of the fiducial marker structure 85. The HMD can be protected from blood and body fluids that may be released from the knee or hip or spine or other surgical site during surgery. A cover 50 for the surgical helmet with a transparent portion 80 can be applied over the surgical helmet 75, and fiducial marker structure 85 with optionally one or multiple fiducial markers 35 can be attached using the magnets. FIG. 4D shows the base 90 of the fiducial marker structure 85, which can include, for example, an optional receptacle 95 for accepting a magnet (not shown).

FIGS. 5A-D are illustrative examples of an integration of an HMD 70 with a surgical helmet 75. The HMD 70 can be mechanically, e.g. removably, attached to the frame of the surgical helmet 75. Two holding members 40 extend superiorly from the HMD 70. A cover 50 for the surgical helmet with a transparent portion 80 can be applied over the surgical helmet 75, and fiducial marker structure 85 with multiple fiducial markers 35 can be attached, for example using a mechanical connection or coupling mechanism, e.g. with a press fit and/or a lock and/or mating features. The HMD can be protected from blood and body fluids that may be released from the knee or hip or spine or other surgical site during surgery. A cover 50 for the surgical helmet with a transparent portion 80 can be applied over the surgical helmet 75, and fiducial marker structure with optionally one or multiple fiducial markers 35 can be attached using the mechanical connection or coupling mechanism. The cover 50 can include one or more openings 90 through which the at least one holding member 40 can extend from the HMD and/or the surgical helmet, located underneath the cover 50, to the area above the cover for placement of the fiducial marker structure 85 with optionally one or multiple fiducial markers 35 located above the cover 50. The one or more fiducial markers 35 can also be placed directly on the at least one holding member 40, above the cover 50.

FIGS. 6A-D are illustrative examples of an HMD 70 with holding members 40 attached to the front of the HMD with magnetic end portions 45 and/or mechanical connectors (not shown). Holding arm 40 or member can also be attached to clear, see through portion of HMD if optical see through head mounted display is used (as compared to video see through head mounted display). Holding arm 40 or member can also be attached to non-see through portion of HMD if video see through head mounted display is used. After sterile cover 50 or hood for the surgical helmet is applied, a second holding arm 55 or member with a second magnet 60 and/or a second mechanical connector (not shown here) can be connected, with the cover 50 for the surgical helmet or hood material interposed, to the first holding arm 40 or member with the first magnet attached to the HMD 70 front portion. Fiducial markers 35 are shown external to the cover for the surgical helmet (not shown).

FIGS. 7A-D are illustrative examples of an HMD 70 with holding arms 55 or bases or fiducial markers 35 attached to outer lens face or front portion of the visor 11. In FIGS. 7A-B, a left and a right cluster of fiducial markers 35 on holding members 55 are shown. Individual fiducial markers also be directly attached to the outer lens face or front portion of the visor 11 or, in FIGS. 7C-D, they can be attached using a base or small holding member 95.

Figure 8A:
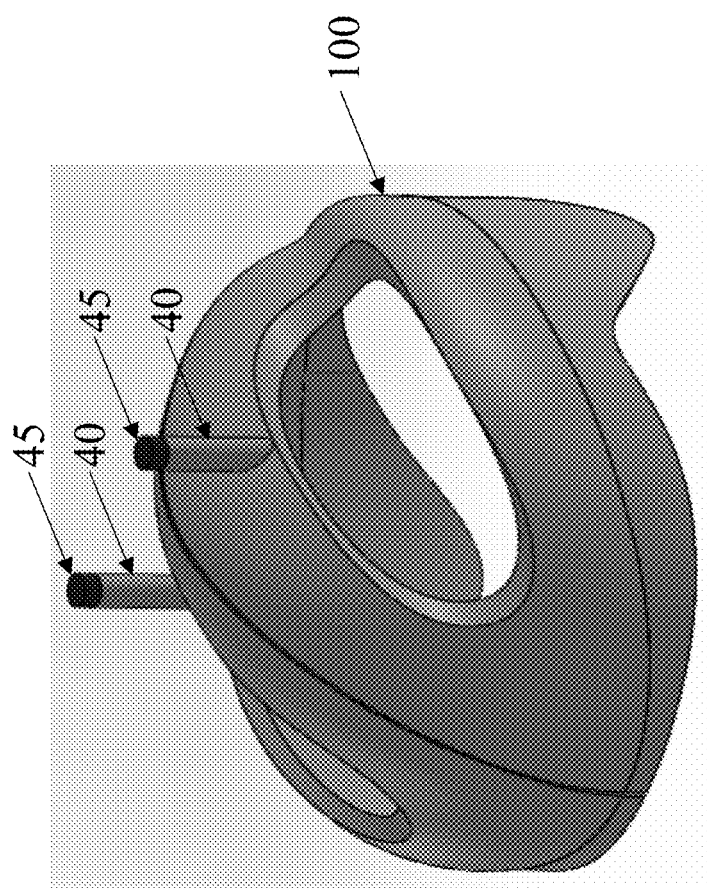
Figure 8D:
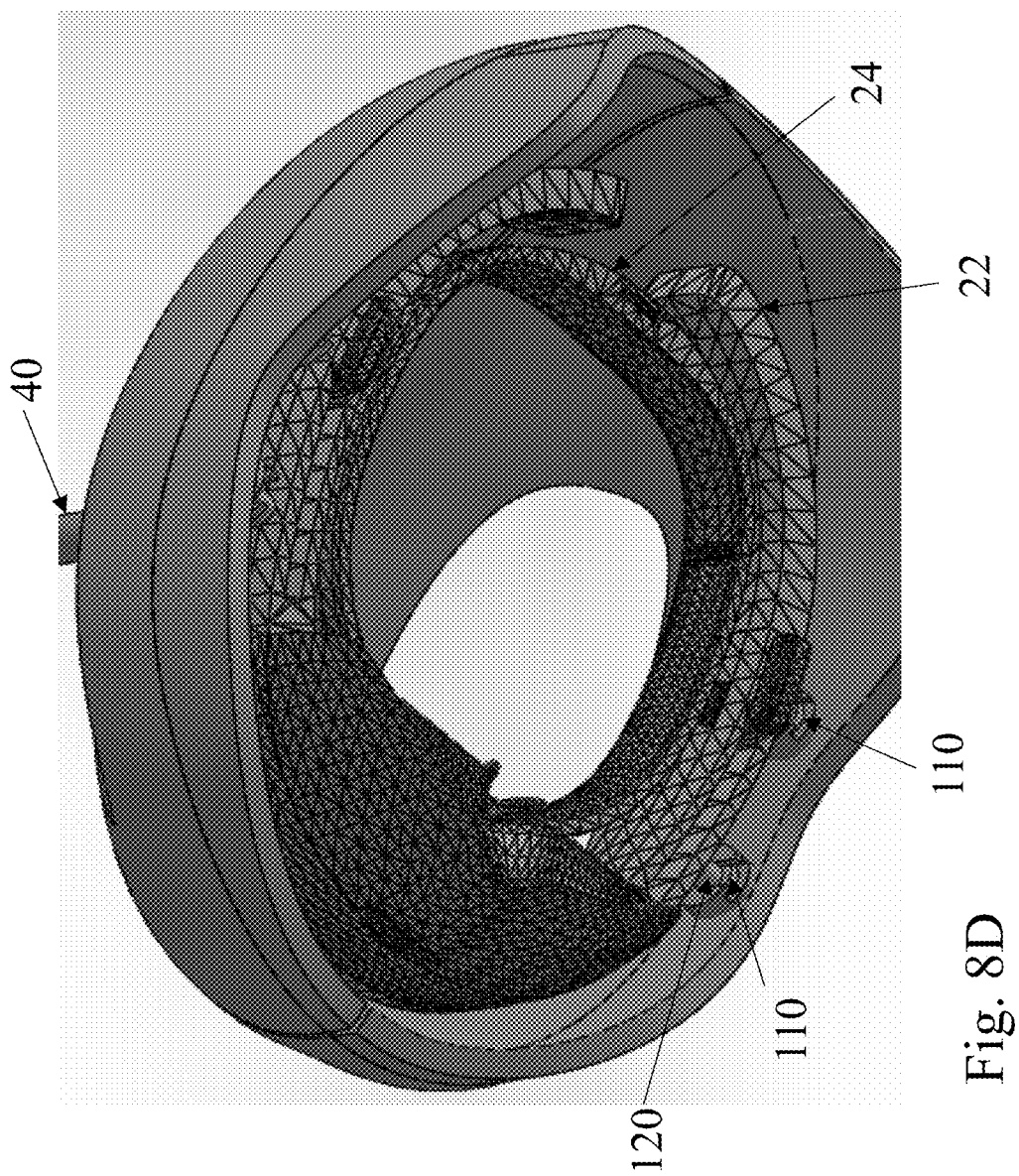
Figure 8E:
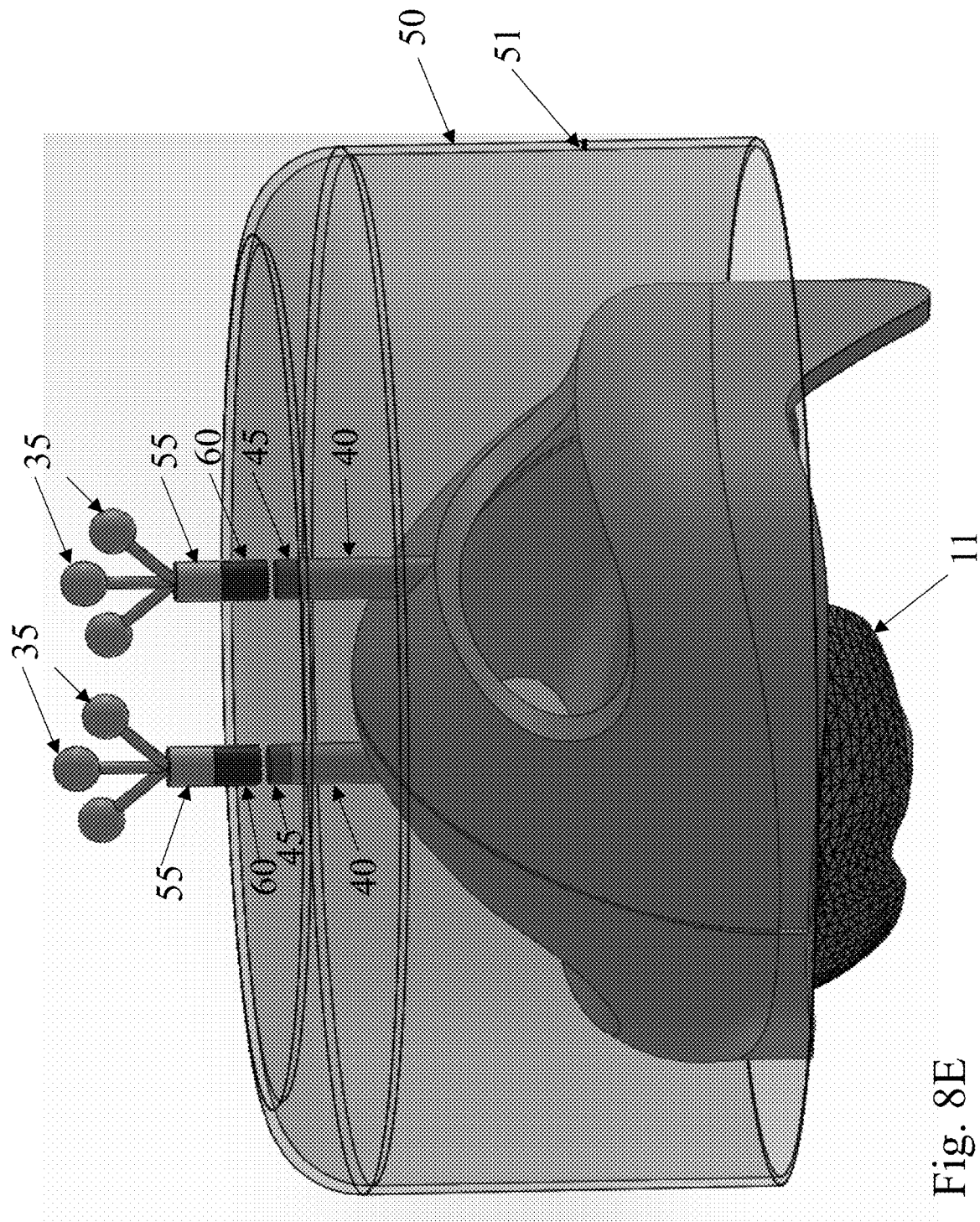

FIGS. 8A-E are illustrative examples of an integration of an HMD 70 with a surgical helmet 100. The surgical helmet 100 can include at least one holding member 40 with magnetic end portions or magnets/magnetic connectors 45 and/or mechanical connectors (not shown). The surgical helmet 100 can include external or internal attachment mechanisms 110, locking mechanisms 110 or coupling mechanisms 110 (for example using mechanical connectors, electromagnetic connectors, or magnets) for connecting an HMD 70. The HMD 70 can comprise external or internal attachment mechanisms 120, locking mechanisms 120 or coupling mechanisms 120 (for example using mechanical connectors, electromagnetic connectors, or magnets) for connecting to the surgical helmet 100. The attachment mechanisms 120, locking mechanisms 120 or coupling mechanisms 120 of the HMD 70 can be male or female; the attachment mechanisms 110, locking mechanisms 110 or coupling mechanisms 110 of the surgical helmet can be the corresponding counterpart male or female, e.g. with the HMD side being male, the surgical helmet side can be female; or with the surgical helmet side being male, the HMD side can be female. FIG. 8D shows the HMD 70 connected to the surgical helmet 100 using HMD side connectors or attachments 120 mating with surgical helmet side connectors 110. The occipital portion, module or component 22 of the HMD 70 is visible; the head holder portion 24 of the HMD 70 is also shown. The holding members 40 can optionally extend to/subjacent to the cover for the surgical helmet 50 or hood or through the cover for the surgical helmet or hood, if the cover for the surgical helmet or hood has openings to accommodate the holding members. In this example, after a cover for the surgical helmet or hood 50 is applied, one or more fiducial markers 35 attached to a second holding member 55 (or a base) with an optional second magnet and/or a second mechanical connector can be connected to the holding member 40 connected to the HMD, with the cover 50 for the surgical helmet or hood interposed. In this example, three fiducial markers 35 are seen on the top left and three fiducial markers 35 are seen on the top right. The fiducial markers 35 can be in a predetermined position and/or orientation relative to the HMD using the one or more holding members 40, 55 (or bases) and the one or more magnets 45, 60. The predetermined position and orientation, and resultant coordinates of the HMD and/or the fiducial markers, can be adjusted for a thickness 51 of the cover for the surgical helmet.

FIGS. 9A-D are illustrative examples of an adjusting mechanism configured to adjust at least a position of the head mounted display attached or connected to a surgical helmet in relationship to the user's eyes. The head mounted display can be configured to be worn on a head of a user under a cover of a surgical helmet so that the display of the HMD is adjacent to a transparent portion of the cover (not shown). The system can comprise a connecting mechanism configured to couple the head mounted display to the surgical helmet. The adjusting mechanism can be configured to adjust the head mounted display in relationship to the user's eyes in an x, a y, or a z-direction or combinations thereof. The adjusting mechanism can be configured to rotate, tilt or rotate and tilt the head mounted display in relationship to at least one of the user's eyes. The adjusting mechanism can comprise a mechanical mechanism configured to adjust the position of the head mounted display; the mechanical mechanism can comprise one or more mechanical elements, wherein the one or more mechanical element can comprise a dial, knob 140, button, lever, slider, handle, handle bar, ring, key, wrench or combinations thereof.

Figure 9A:
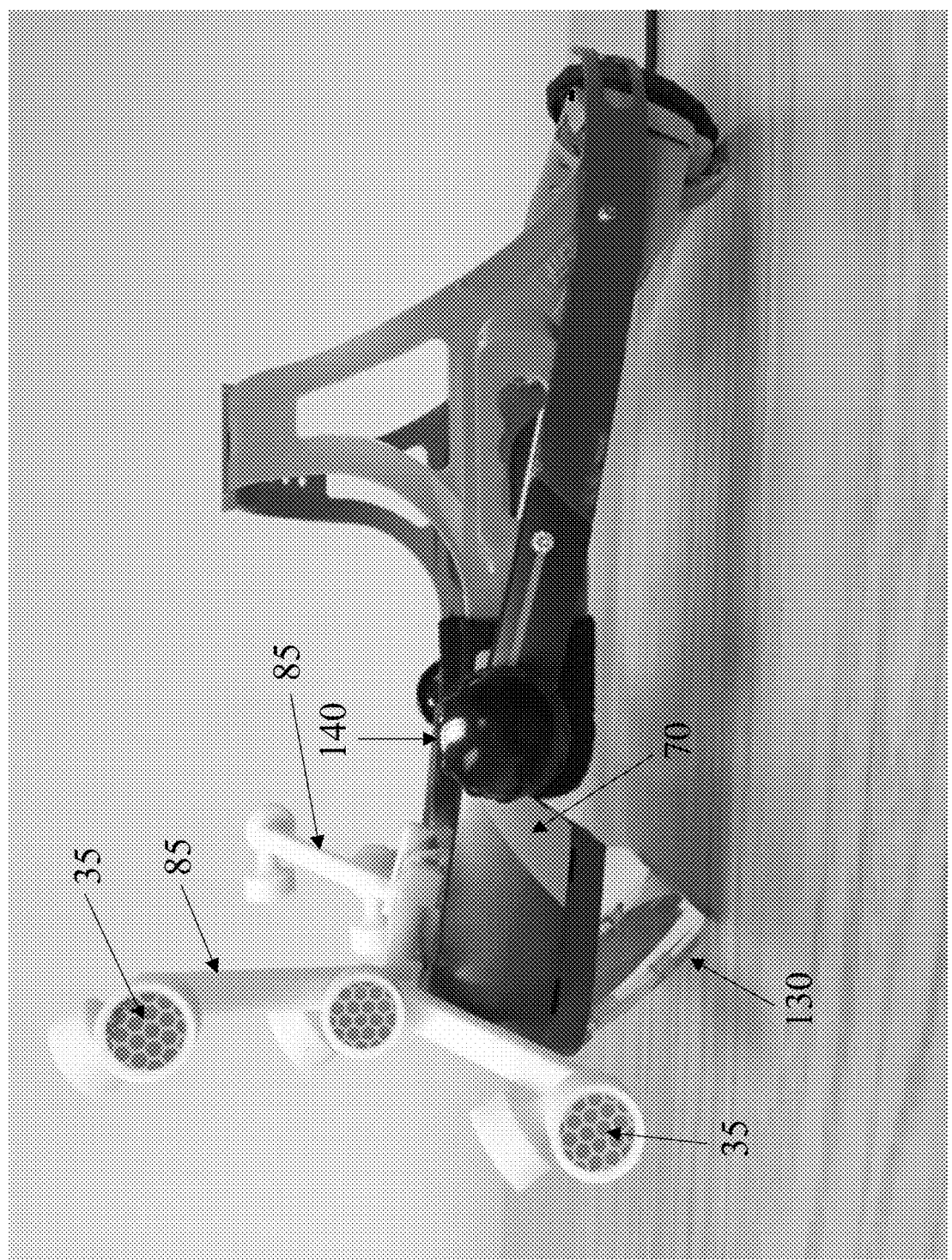
FIGS. 9A-9D are illustrative examples of an adjusting mechanism configured to adjust at least a position of the head mounted display attached or connected to a surgical helmet in relationship to the user's eyes according to some embodiments.
Figure 9B:
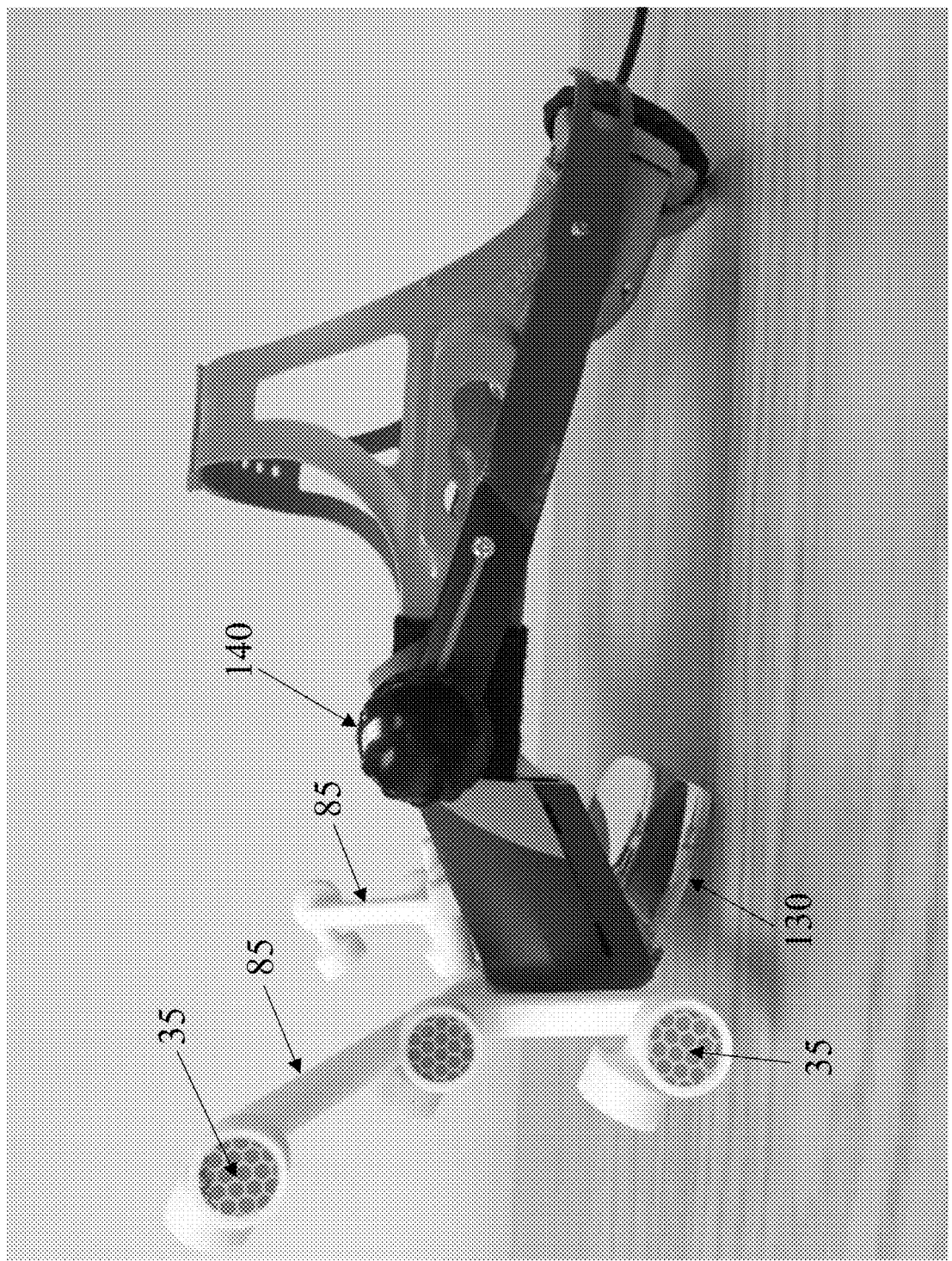
Figure 9C:
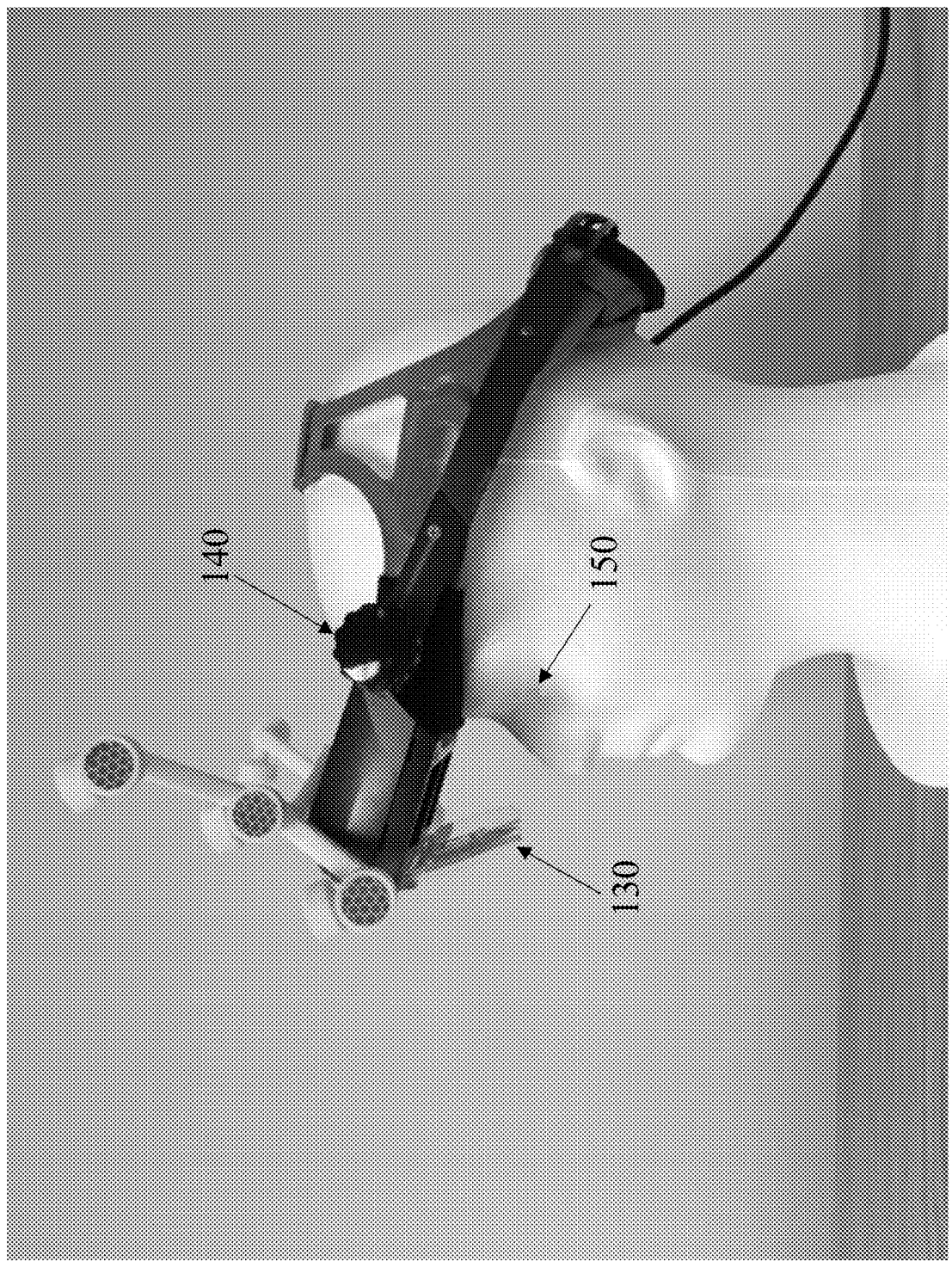
Figure 9D:
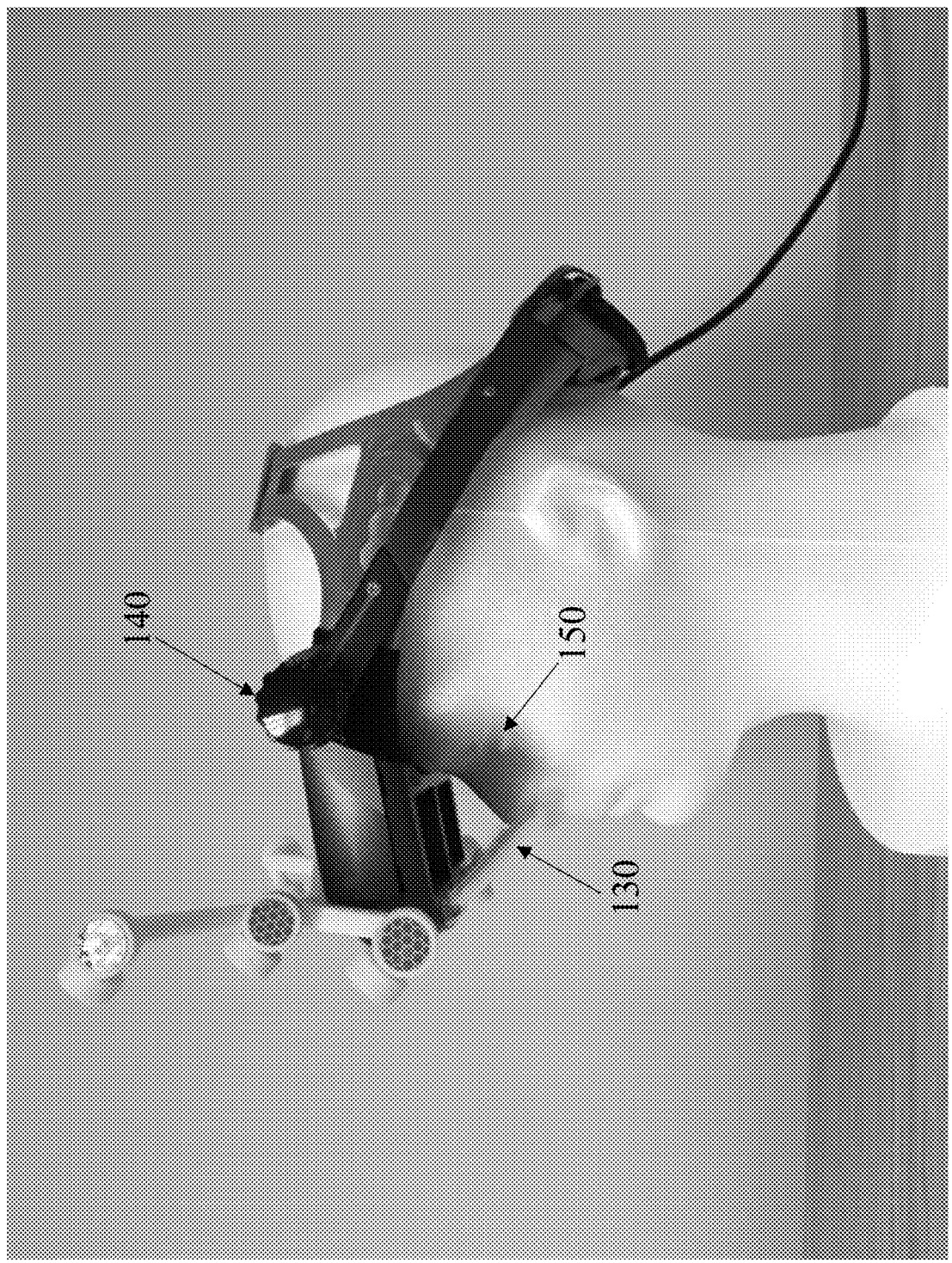
Figure 10A:
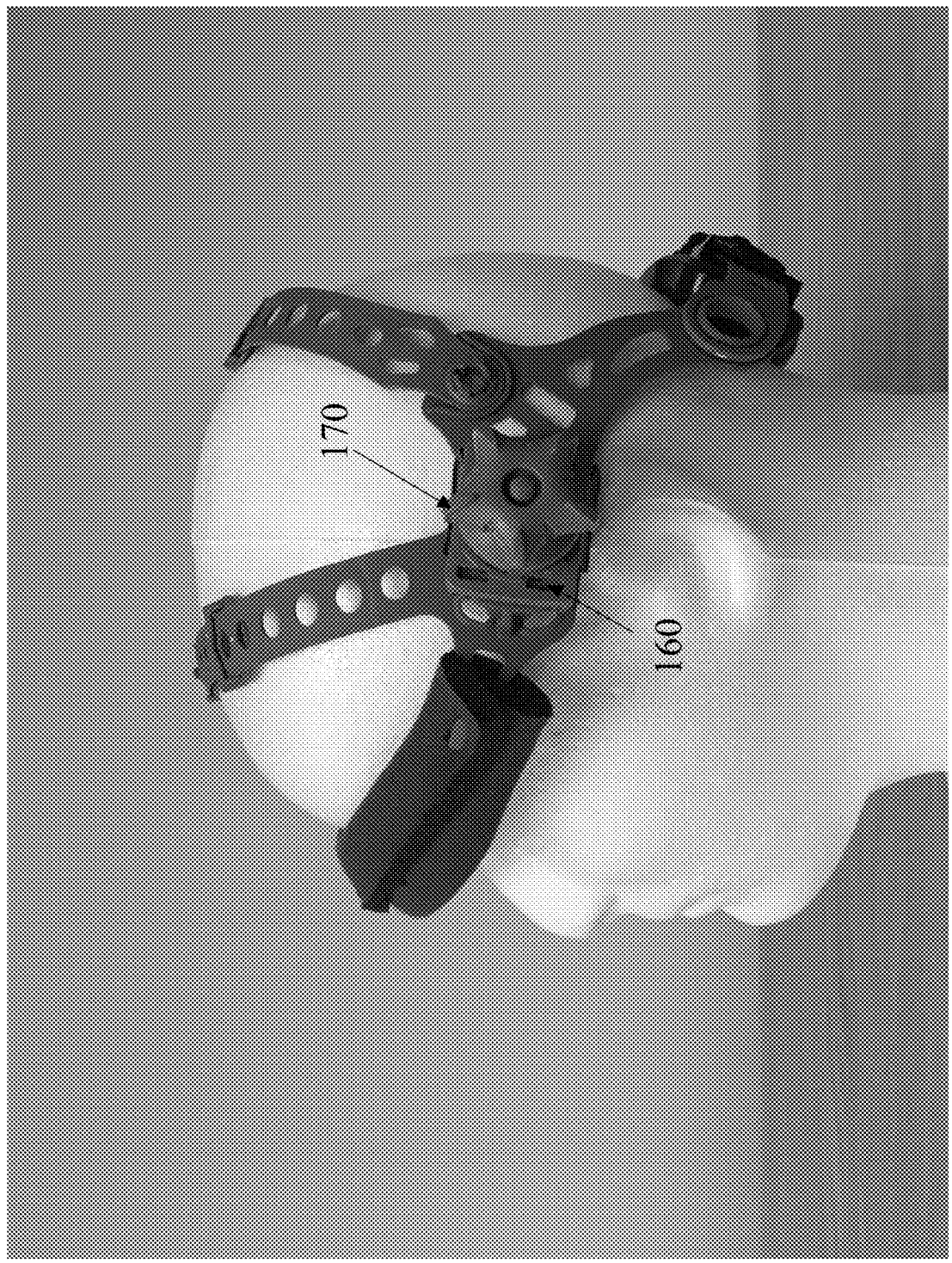
FIGS. 10A-10B are illustrative examples of an adjusting mechanism using a mechanical mechanism with mechanical elements comprising, for example, ratchet like elements and knob like elements for moving an attached HMD according to some embodiments.
Figure 10B:
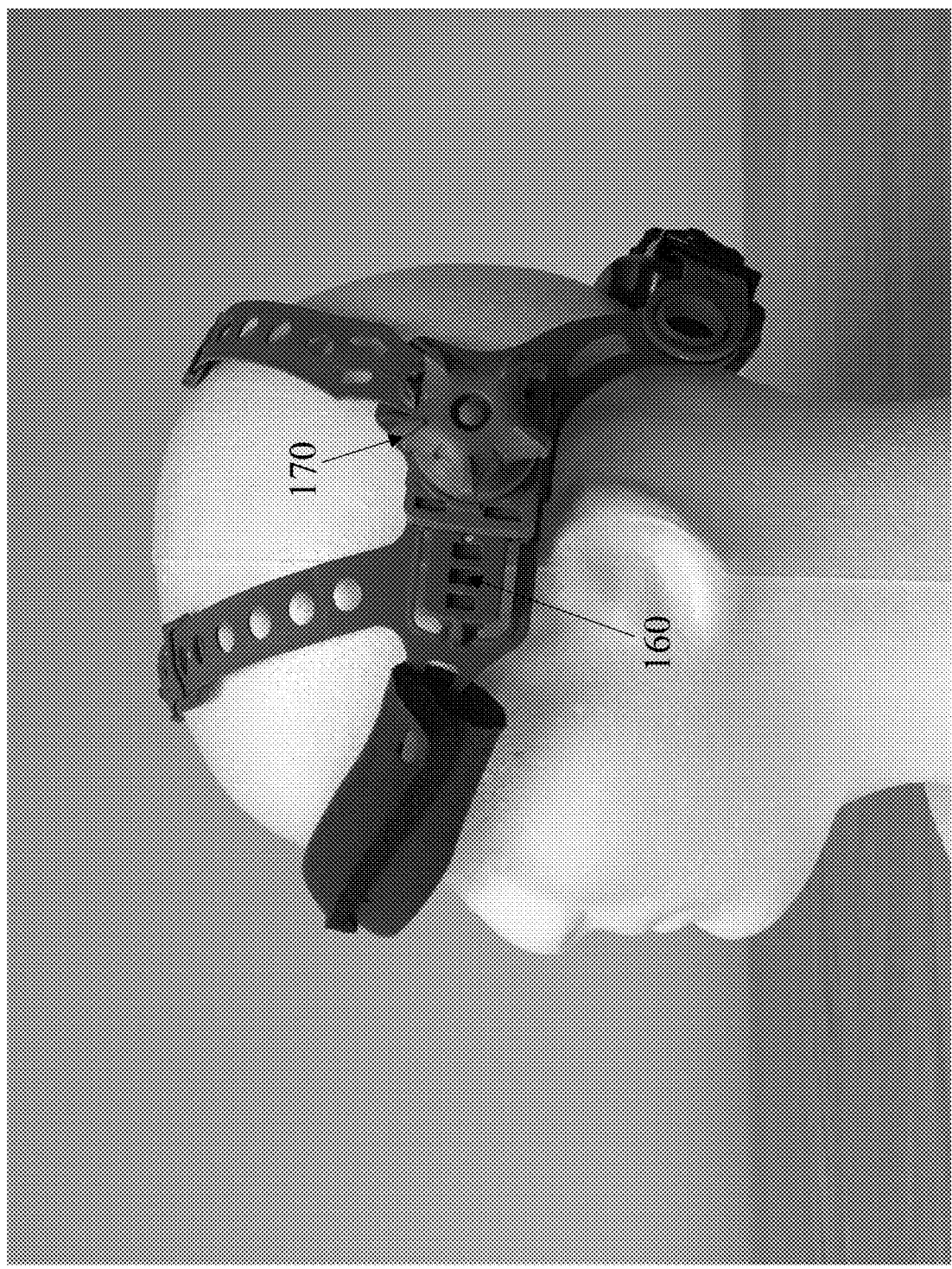

In FIG. 9A, markers 35 are seen attached to a marker structure 85, which can be attached to the HMD 70. Am adjusting mechanism, e.g. a mechanical mechanism configured to adjust the position of the head mounted display, in this example a knob 140, is seen, which can be operated, for example through an overlying or superjacent cover for a surgical helmet to move, rotate and/or tilt the HMD or the display unit 130 of the HMD 70, including with the HMD connected or attached to the surgical helmet. In FIG. 9B, the adjusting mechanism 140 has been operated to tilt the HMD including its display unit 130. FIG. 9C is an illustrative example showing the HMD on the user's head. The HMD including its display unit 130 is not well aligned with the user's eyes 150. In FIG. 9D, the adjusting mechanism 140 has been operated to move, e.g. translate, rotate, tilt, the HMD; the display unit of the HMD 130 is now centered over the user's eyes 150. Depending on the surgeon's head shape, the surgical helmet with a connected and/or attached HMD may move the HMD into a position and/or orientation where the HMD is not aligned with or centered over the surgeon's eyes and/or pupils and/or visual field. The adjusting mechanism can be used to move the HMD 70, including the display unit of the HMD 130, forward, backward, up and down, or to rotate and/or tilt it in relationship to the user's eyes. The virtual display can be centered in this manner in relationship to the surgeon's eyes and/or pupils and or the surgeon's visual field, even in the presence of a mechanical connection or attachment between the HMD and the surgical helmet. FIGS. 10A-6 are illustrative examples of an adjusting mechanism using a mechanical mechanism with mechanical elements comprising ratchet like elements 160 and knob like elements 170 for moving an attached HMD (not shown). The adjusting mechanism and mechanical elements can be integrated into or attached to the HMD, the surgical helmet or both.

Figure 11A:
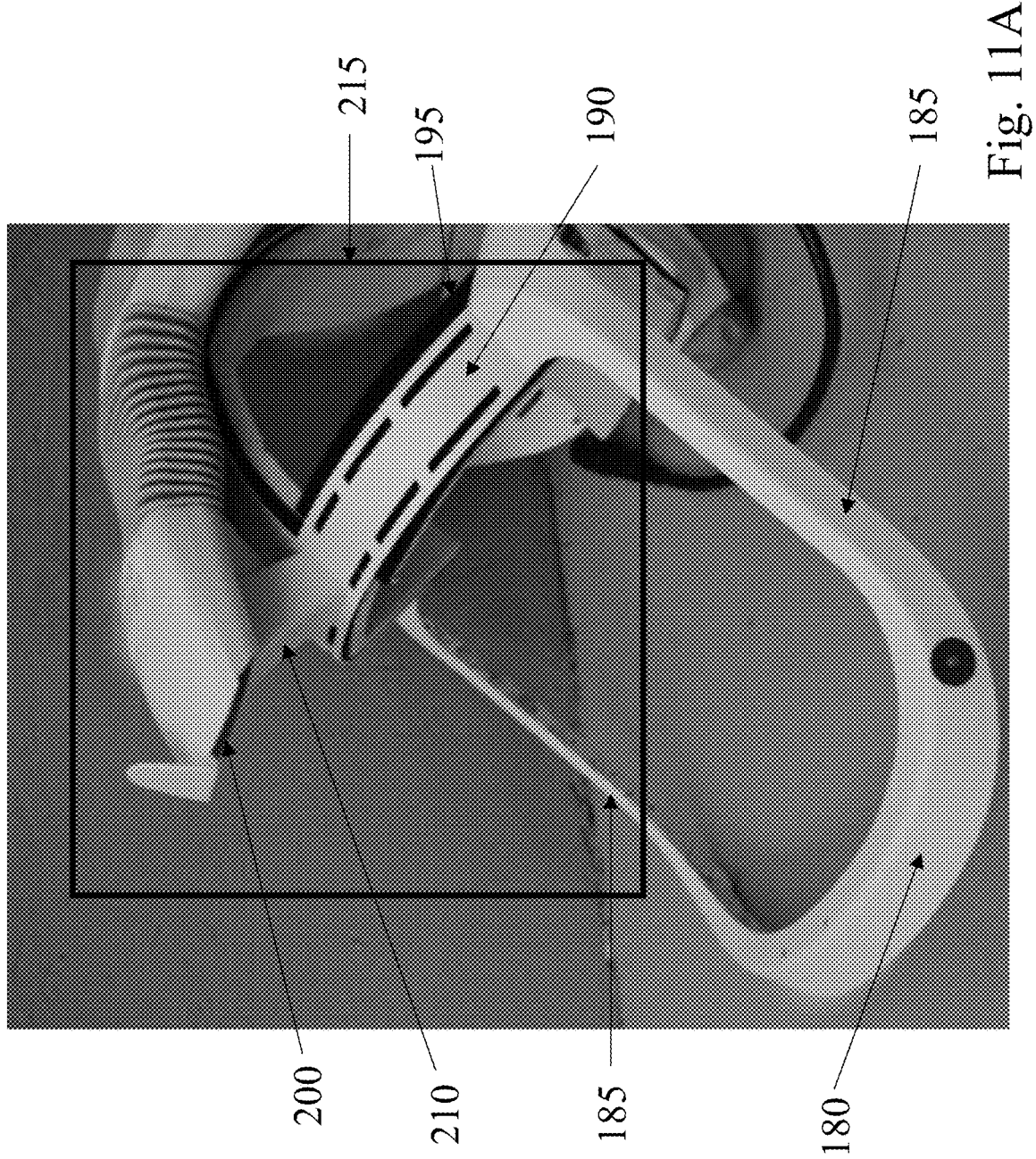
FIGS. 11A-11J are illustrative, non-limiting examples of an adjusting mechanism configured to adjust at least a position of the head mounted display in relationship to the user's eyes, while the user is wearing a surgical helmet. The HMD can be attached to the surgical helmet using various attachment means or connecting mechanisms according to some embodiments.
Figure 11B:
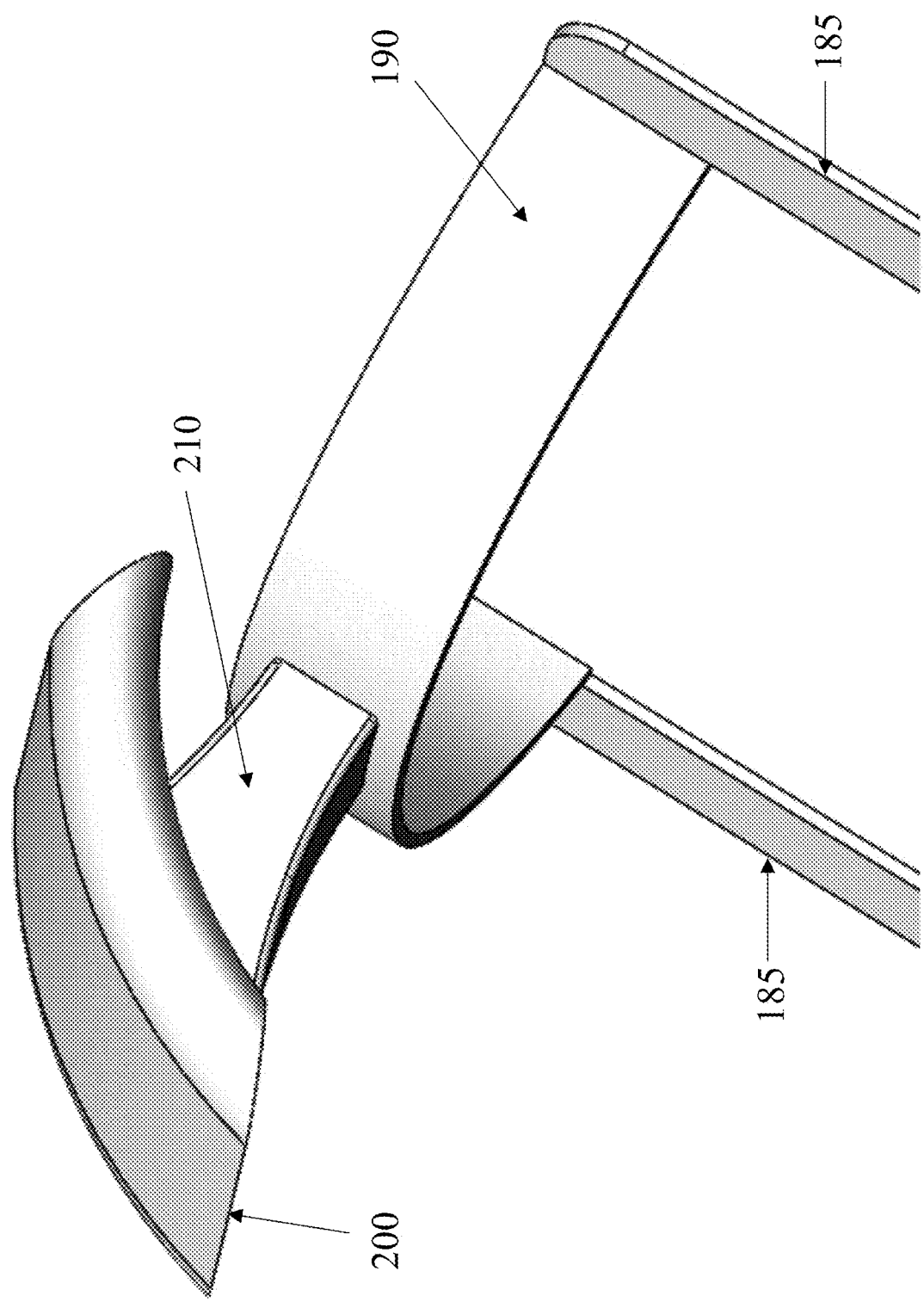
Figure 11C:
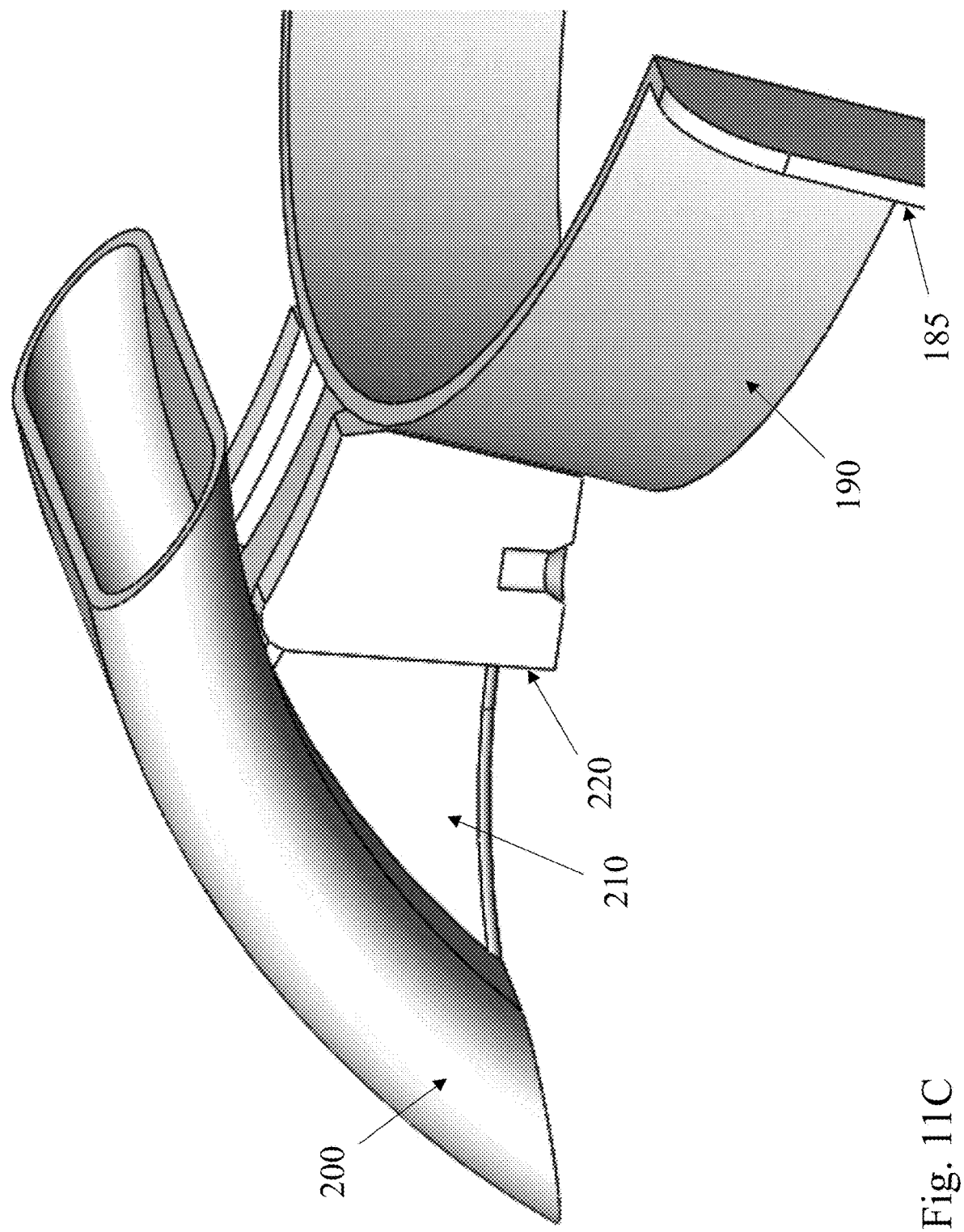
Figure 11D:
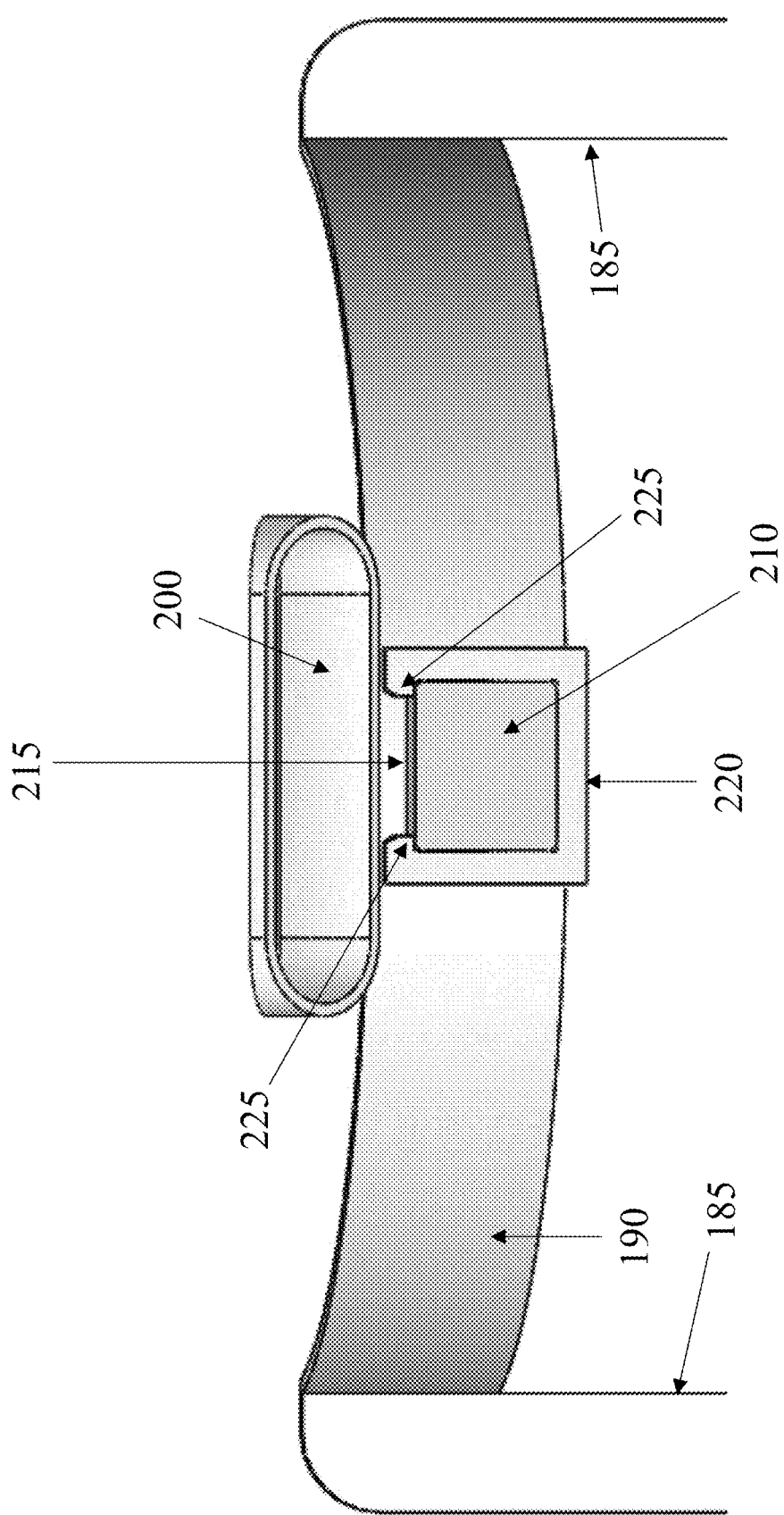

FIGS. 11A-J are illustrative, non-limiting examples of an adjusting mechanism configured to adjust at least a position of the head mounted display in relationship to the user's eyes, while the user is wearing a surgical helmet. The HMD can be attached to the surgical helmet using various attachment means or connecting mechanisms. The HMD can be removably attachable. The head mounted display can be configured to be worn on a head of a user under a cover of a surgical helmet so that the display of the head mounted display is adjacent to a transparent portion of the cover. FIG. 11A is an illustrative example of a surgical helmet. The surgical helmet can optionally comprise a chin portion 180, a forehead or frontal portion 190, side members 185 connecting the chin portion 180 with the frontal portion 190, a head band or felt portion 195, an air duct 200, e.g. for circulating air inside the cover for the surgical helmet, a support element 210, in this example connecting the air duct 200 with the frontal portion 190. Frame 215 outlines the general area for the views including magnified views shown in FIGS. 11B-J. FIG. 11B is a magnified view showing the air duct 200, support element 210, frontal portion 190, and side members 185. FIG. 11B is a side view showing the air duct 200, support element 210, frontal portion 190, and side members 185. FIG. 11C is another side view showing the air duct 200, support element 210, frontal portion 190, and side members 185. An attachment member or mechanism 220 for attaching the HMD (not shown) to the surgical helmet is shown. In this example, the attachment member or mechanism attaches to the support element 210. The attachment member or mechanism 220 can attach to any other portion or element of the surgical helmet. FIG. 11D is a view from the rear showing a cross-section of the air duct 200, a cross section of support element 210, the rear (forehead facing) of the frontal portion 190, and side members 185. The attachment member or mechanism 220 for attaching the HMD (not shown) to the surgical helmet is shown, in this example partially encircling the support element 210. Tabs or struts 225 extend from the attachment member or mechanism 220 over the top portion 215 of the support member 210, thereby securing the attachment member or mechanism 220 to the support member 210. The attachment member or mechanism 220 can attach to any other portion or element of the surgical helmet.

Figure 11E:
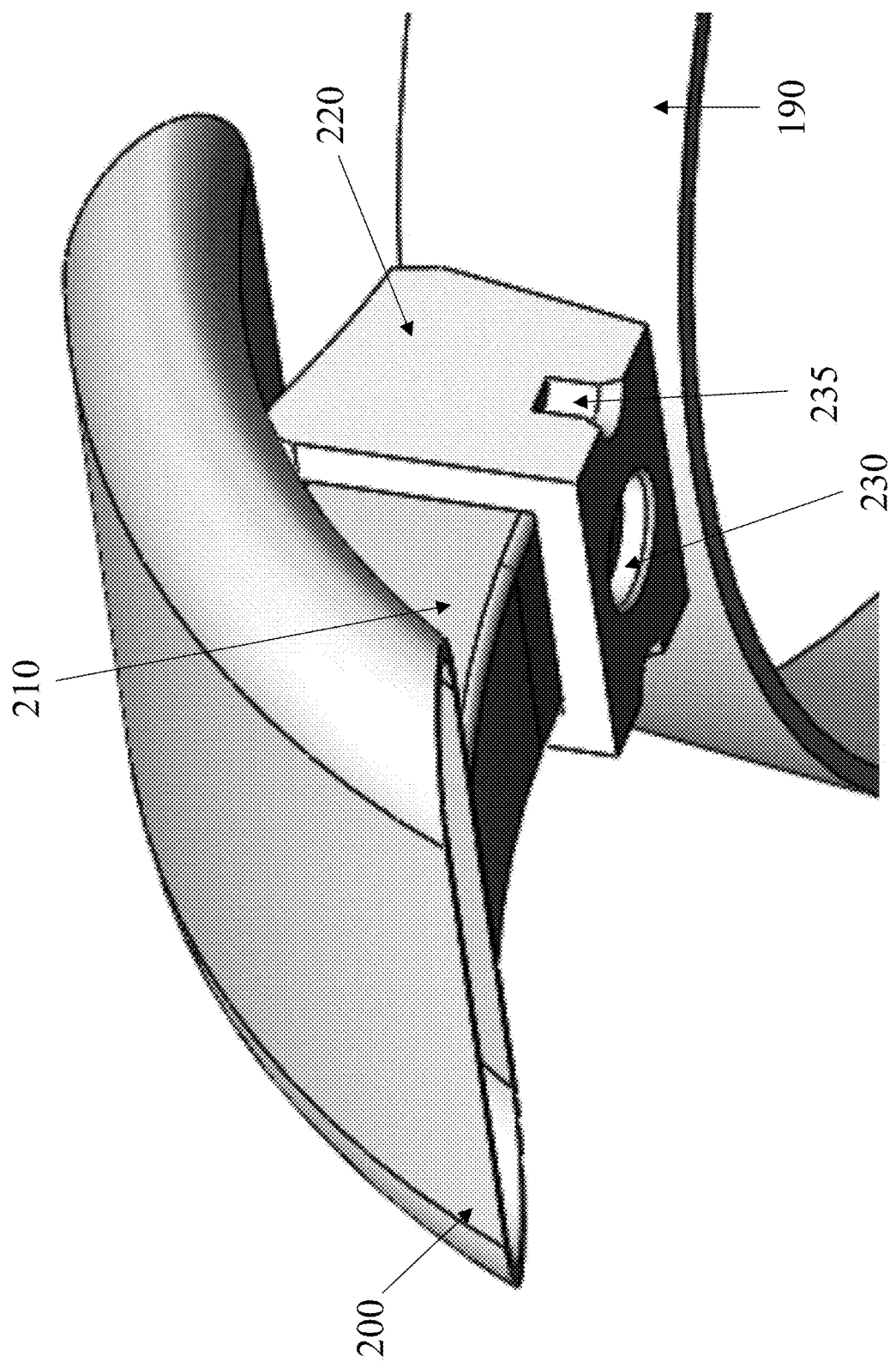

FIG. 11E shows air duct 200, support element 210, frontal portion 190, with attachment member or mechanism 220 attached to support element 210. Attachment member or mechanism 220 comprises an optional recess or receptacle 230 for receiving a magnet (not shown) for attaching an HMD. The magnets can be configured for removable attachment of the HMD. Similarly, the attachment member or mechanism 220 can be configured to be removably attachable, for example using partially flexible tabs or struts (225, FIG. 11D). Attachment member or mechanism 220 comprises also lateral centering elements 235, configured to receive centering arms or struts (not shown) for attaching and aligning an HMD.

Figure 11G:
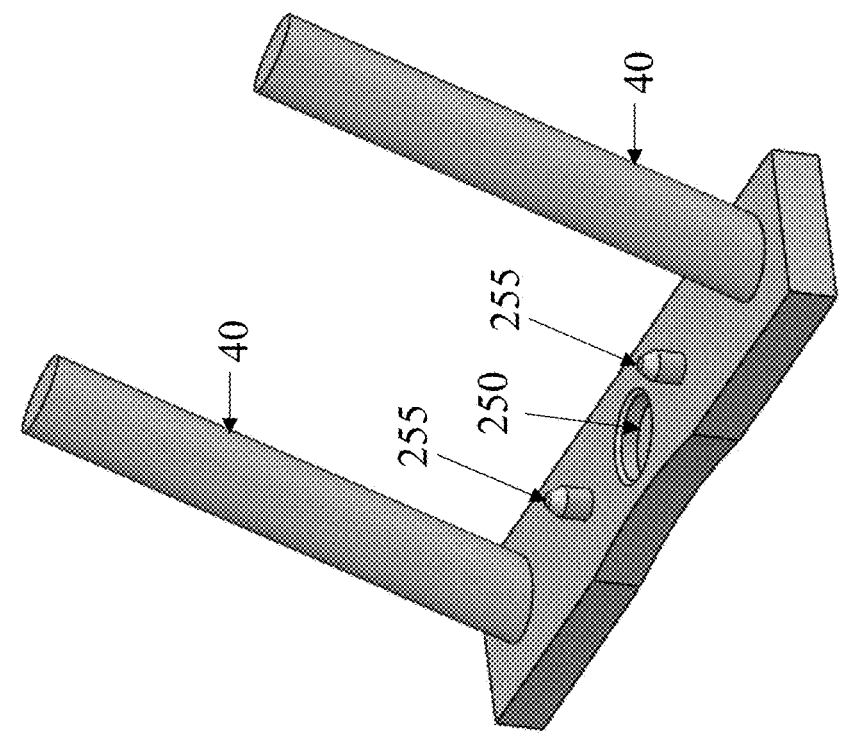
Figure 11F:
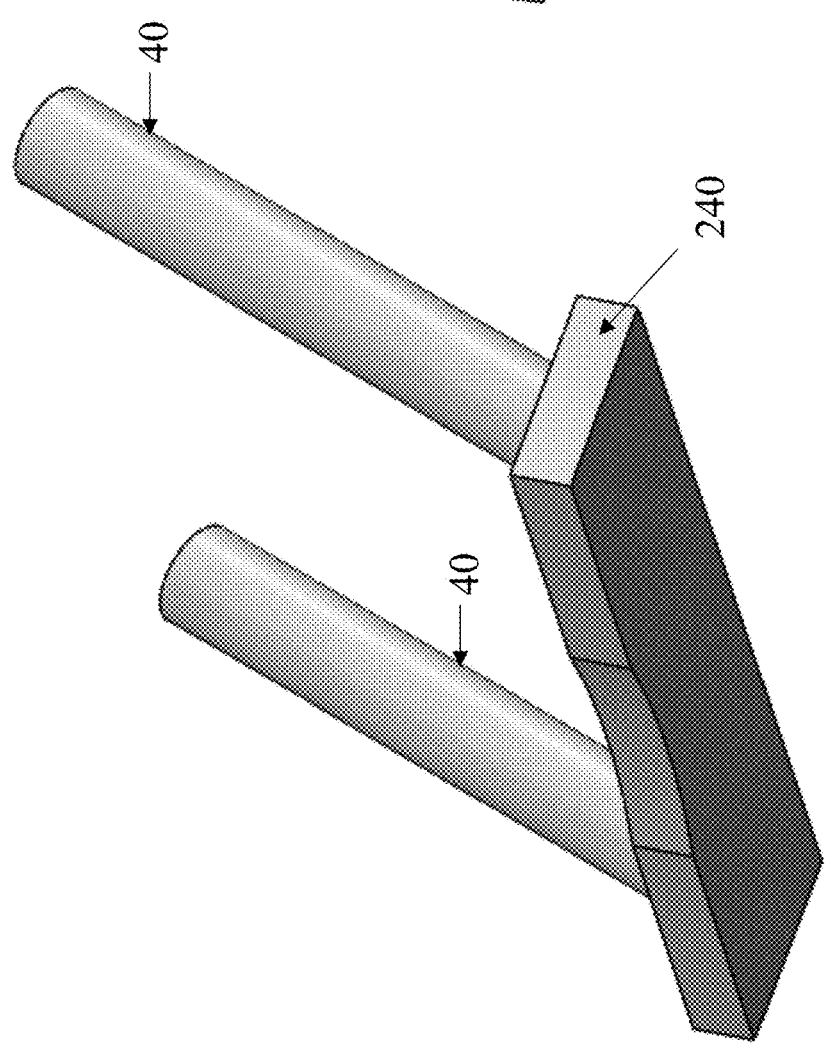

FIGS. 11F-G show illustrative, non-limiting examples of an attachment member or mechanism 240, for example for attachment to or integration into an HMD. The attachment member or mechanism 240 can comprise holding members 40, for example for accepting or attaching one or more markers, e.g. fiducial markers. The attachment member or mechanism 240 can include a recess or receptacle, for example for receiving a magnet or corresponding metal component or mechanical attachment mechanism to couple and/or connect the attachment member 240 (with the attached HMD) to the attachment member 220 attached to the surgical helmet. At least one magnet, for example placed in recess or receptacle 230 or placed in recess or receptacle 250 can be used for attaching the attachment member 240 (with the attached HMD) to the attachment member 220 attached to the surgical helmet; alternatively, at least one mechanical connector and/or mechanical connecting element can be used. Centering members or struts 255 can be configured to align with/to be placed in or to mate with centering elements 235, thereby aligning the attachment member 240 (with the attached HMD) with the attachment member 220 and the attached surgical helmet in a predetermined pose/position and/or orientation.

Figure 11H:
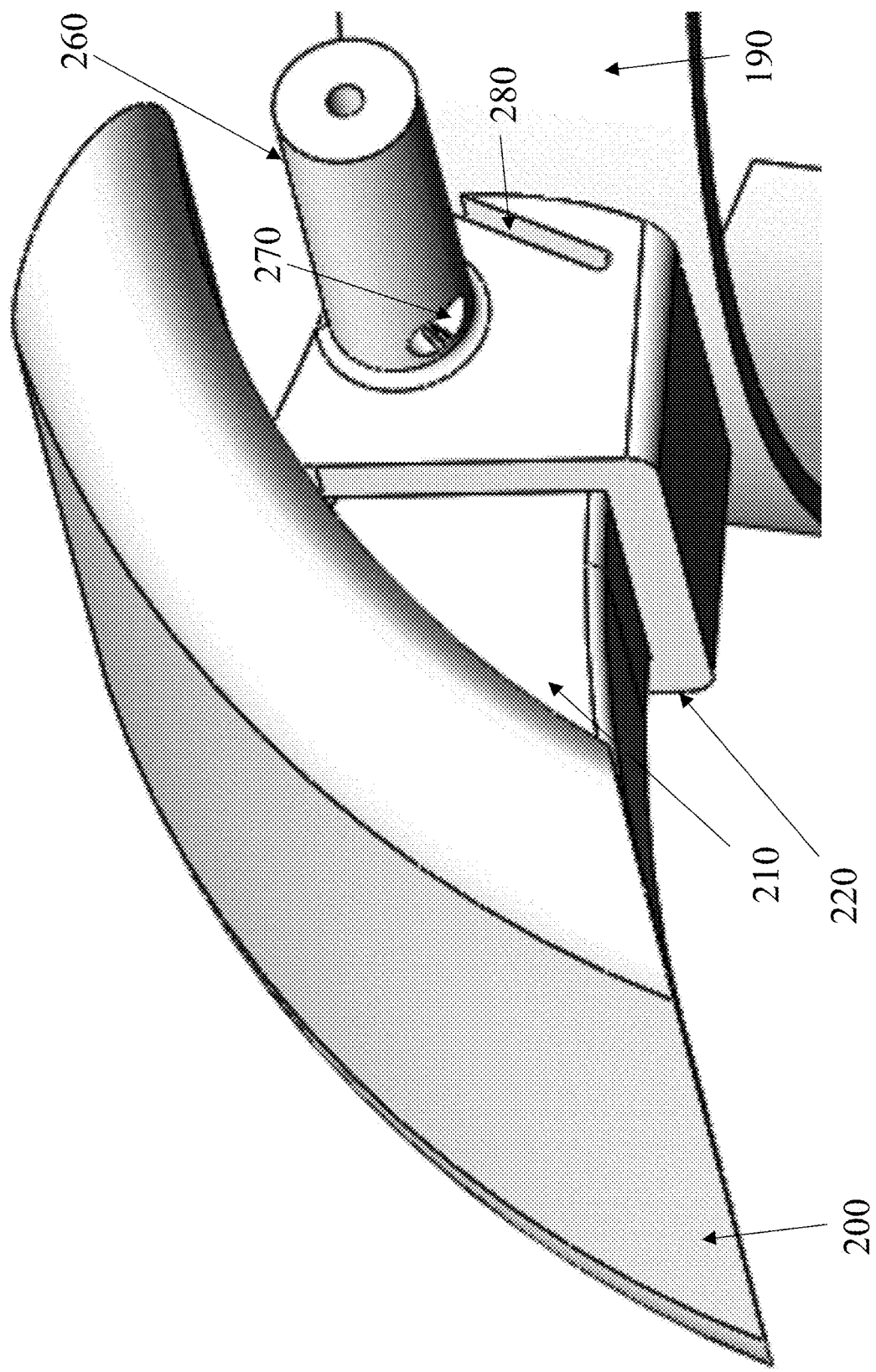

FIG. 11H shows air duct 200, support element 210, frontal portion 190, with attachment member or mechanism 220 attached to support element 210. Attachment member or mechanism 220 comprises an adjusting mechanism 260 to adjust at least a position of the head mounted display attached to or connected to the surgical helmet in relationship to the user's eyes. The adjustment mechanism 260 comprises an optional thread 270 to accept an optional screw (not shown). The adjustment mechanism 260 comprises also a slot 280, for example for slideably engaging an attachment member of an HMD or for slideably engaging a portion of an HMD housing or holder or support member.

Figure 11J:
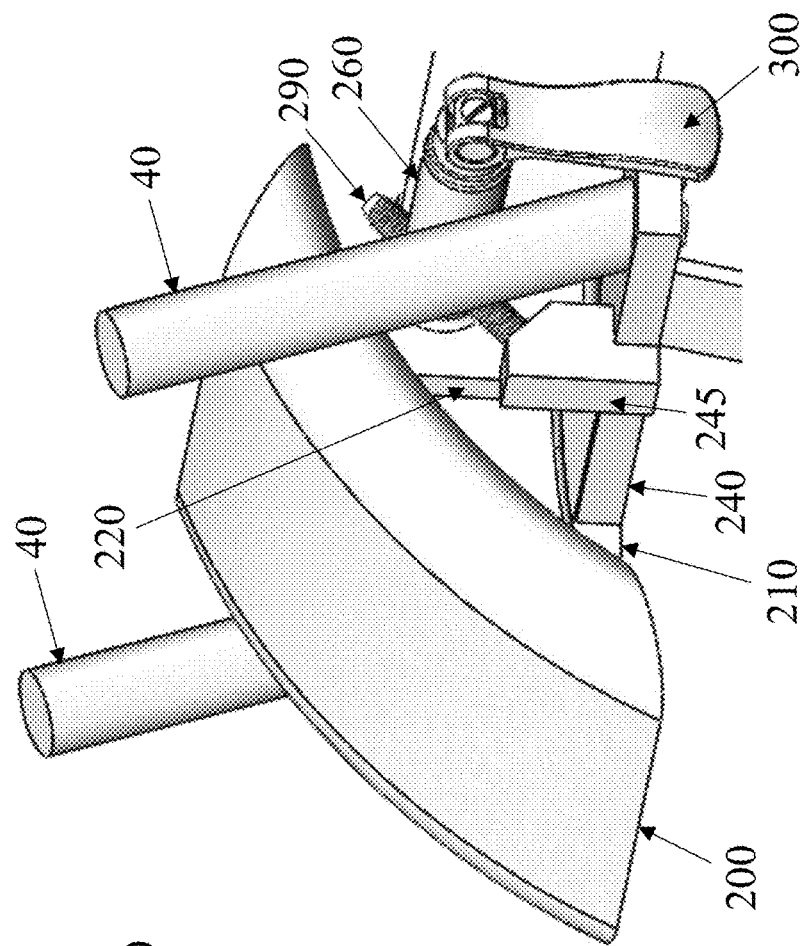
Figure 11I:
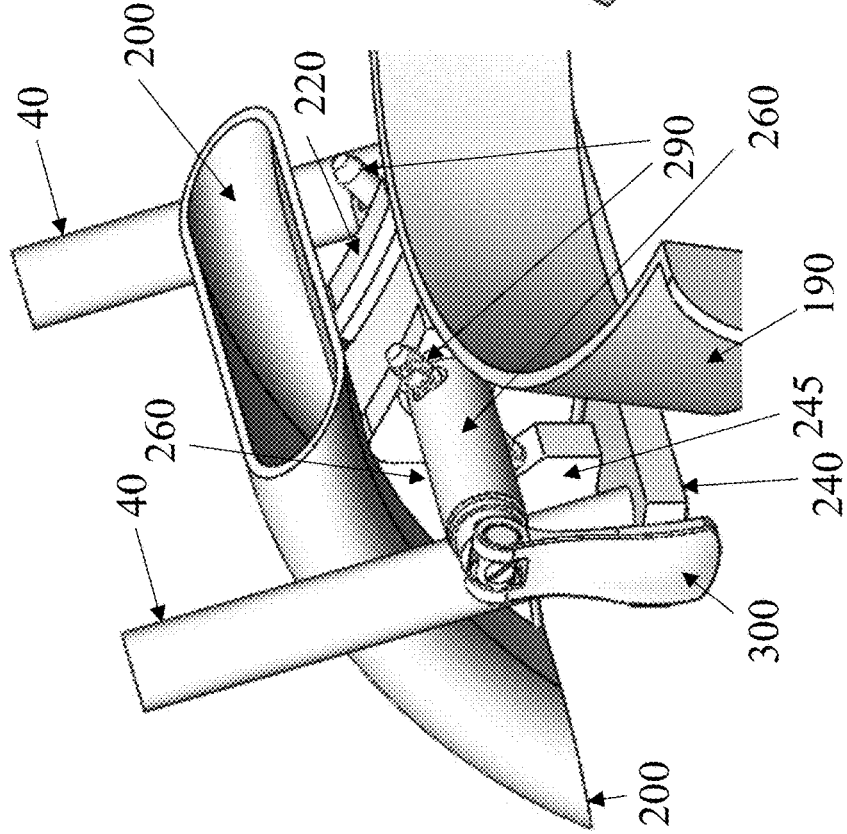

FIGS. 11I-J show air duct 200, frontal portion 190, with attachment member or mechanism 220 attached to support element 210. Attachment member or mechanism 220 comprises an adjusting mechanism 260 to adjust at least a position of the head mounted display (not shown) attached to or connected to the surgical helmet in relationship to the user's eyes. The adjustment mechanism 260 comprises an optional thread to accept an optional screw 290. The screw 290 can be threaded into an extension 245 of attachment member 240 integrated into or attached to the HMD/HMD housing (not shown). The adjustment mechanism 260 can comprise a wing nut, knob, lever 300, or other mechanical element or motor, for example for moving the screw and for moving, rotating, and/or tilting the attachment member 240 integrated into or attached to the HMD/HMD housing, thereby moving, rotating or tilting the HMD to adjust at least a position of the HMD in relationship to the user's eyes, while the HMD is coupled to the surgical helmet, e.g. moving the HMD up, down, forward, backward, or rotating the HMD in relationship to the user's eyes, optionally centering the HMD over the user's eyes/pupils.

In some embodiments, the adjusting mechanism can be configured to the center the HMD, and with it the display unit of the HMD and/or the display of virtual data over the user's eyes/pupils. In some embodiments, the adjusting mechanism can be configured to the adjust position of the HMD, and with it the display unit of the HMD and/or the display of virtual data over the user's eyes/pupils so that the display is adjacent to a transparent portion of the cover for the surgical helmet and so that the user can observe the surgical site through the see through HMD and the transparent portion.

In some embodiments, the adjusting mechanism can be activated pre-operatively to adjust the position of the HMD, and with it the display unit of the HMD and/or the display of virtual data in relationship to the user's eyes/pupils. In some embodiments, the adjusting mechanism can be activated intra-operatively to adjust the position of the HMD, and with it the display unit of the HMD and/or the display of virtual data in relationship to the user's eyes/pupils. The adjusting mechanism can comprise a mechanical mechanism configured to adjust the position of the head mounted display, wherein the mechanical mechanism can comprise one or more mechanical elements, wherein the one or more mechanical element can comprise a dial, knob, button, lever, slider, handle, handle bar, ring, key, wrench or combinations thereof. In some embodiments, the mechanical elements can be configured so that they can be operated with the cover for the surgical helmet overlying the mechanical elements, i.e. with the mechanical elements, e.g. a dial, knob, button, lever, slider, handle, handle bar, ring, key, wrench or combinations thereof, subjacent to the cover for the surgical helmet. For example, in the latter embodiment, the user can palpate the mechanical elements, e.g. a dial, knob, button, lever, slider, handle, handle bar, ring, key, wrench or combinations thereof, through the cover and control them through the cover. In some embodiments, the cover for the surgical helmet can include at least one opening, with at least portions of one or more mechanical elements, e.g. dial, knob, button, lever, slider, handle, handle bar, ring, key, wrench or combinations thereof, being positioned/located superjacent and/or external to the cover of the surgical helmet. Optionally, the at least portions of the one or more mechanical elements being positioned/located superjacent and/or external to the cover of the surgical helmet can be provided in sterile fashion. In some embodiments, the mechanical elements, e.g. a dial, knob, button, lever, slider, handle, handle bar, ring, key, wrench or combinations thereof, can comprise a metal base and can be located external to the cover for the surgical helmet and can be coupled, without an opening in the cover, to a holding member, connector or second mechanical element comprising a magnet. In some embodiments, the mechanical elements, e.g. a dial, knob, button, lever, slider, handle, handle bar, ring, key, wrench or combinations thereof, can comprise a magnet and can be located external to the cover for the surgical helmet and can be coupled, without an opening in the cover, to a holding member, connector or second mechanical element comprising a metal coupling portion. In some embodiments, the mechanical elements, e.g. a dial, knob, button, lever, slider, handle, handle bar, ring, key, wrench or combinations thereof, can comprise a first magnet and can be located external to the cover for the surgical helmet and can be coupled, without an opening in the cover, to a holding member, connector or second mechanical element comprising a second magnet.

In some embodiments, the adjusting mechanism can comprise a motor, a motorized element, an electric element, an electromagnetic element, a piezoelectric element or combinations thereof and a user interface can be configured to control the motor, the motorized element, the electric element, the electromagnetic element, the piezoelectric element or combinations thereof for adjusting the position of the HMD in relationship to the user's eyes. In some embodiments, the adjusting mechanism can comprise a motor, a motorized element, an electric element, an electromagnetic element, a piezoelectric element or combinations thereof and an eye tracking system, including optionally one or more cameras directed at the eyes/pupils, can be configured to control the motor, the motorized element, the electric element, the electromagnetic element, the piezoelectric element or combinations thereof for adjusting the position of the HMD in relationship to the user's eyes.

Reference is made to PCT application PCT/US19/15522, filed Jan. 29, 2019, and PCT application PCT/US18/12459, filed on Jan. 5, 2018, which are hereby incorporated by reference in their entireties.

All publications, patent applications and patents mentioned herein are hereby incorporated by reference in their entirety as if each individual publication or patent was specifically and individually indicated to be incorporated by reference.

The invention claimed is:

1. A system, the system comprising:
   a surgical helmet comprising a sterile cover configured to cover the surgical helmet;
   a head mounted display comprising a display;
   at least one holding member;
   a mechanical adjusting mechanism; and
   a connecting mechanism,
      wherein the surgical helmet is configured to be worn on a head of a user;
      wherein the head mounted display is configured to be worn on the head of the user and under the sterile cover,
      wherein the connecting mechanism is configured to couple the head mounted display to the surgical helmet;
      wherein the surgical helmet comprises the mechanical adjusting mechanism;
      wherein the sterile cover is configured to cover the surgical helmet comprising the mechanical adjusting mechanism and the head mounted display,
      wherein the sterile cover comprises a transparent portion and a non-transparent portion and wherein the transparent portion of the sterile cover is adjacent to the display of the head mounted display,
      wherein the mechanical adjusting mechanism is configured to adjust at least a position, orientation or combination thereof of the head mounted display in relationship to the eyes of the user,
      wherein the mechanical adjusting mechanism is configured to be operable through the non-transparent portion of the sterile cover of the surgical helmet,
      wherein the at least one holding member is integrated into or configured to be attached to or connected to the head mounted display, display, the surgical helmet or the head mounted display and the surgical helmet,
      wherein the at least one holding member is configured to extend through at least one opening of the sterile cover.

2. The system of claim 1, wherein the mechanical adjusting mechanism comprises the connecting mechanism.

3. The system of claim 1, wherein the mechanical adjusting mechanism is configured to adjust the head mounted display in relationship to the eyes of the user in an x, a y, or a z-direction or combinations thereof.

4. The system of claim 1, wherein the adjustment of the head mounted display comprises a translation of about 30 mm, about 25 mm, about 20 mm, about 15 mm, about 10 mm, about 7 mm, about 5 mm, about 4 mm, about 3 mm, about 2 mm, about 1 mm, about 0.5 mm, about in at least one of an x, a y, or a z-direction or combinations thereof.

5. The system of claim 1, wherein the mechanical adjusting mechanism is configured to rotate, tilt or rotate and tilt the head mounted display in relationship to at least one of the user's eyes.

6. The system of claim 5, wherein the rotating, tilting, or rotating and tilting of the head mounted display comprises a change in angular orientation of about 30°, about 25°, about 20°, about 15°, about 10°, about 9°, about 8°, about 7°, about 6°, about 5°, about 4°, about 3°, about 2°, about 1°, about 0.5°, about 0.25° in at least one direction.

7. The system of claim 1, wherein the mechanical adjusting mechanism is configured for adjusting the position of the head mounted display prior to a surgical procedure or during the surgical procedure or prior to and during the surgical procedure.

8. The system of claim 1, wherein the mechanical mechanism comprises one or more mechanical elements, wherein the one or more mechanical element comprises a dial, knob, button, lever, slider, handle, handle bar, ring, key, wrench or combinations thereof.

9. The system of claim 1, wherein the mechanical mechanism comprises one or more mechanical elements configured to be subjacent to the sterile cover for the surgical helmet, and wherein the mechanical element is configured to be operated through the cover for the surgical helmet.

10. The system of claim 1, wherein the at least one holding member is attached directly to the head mounted display.

11. The system of claim 1, wherein the at least one holding member is attached indirectly to the head mounted display.

12. The system of claim 1 further comprising:
    at least one marker;
    wherein the at least one marker is configured to be integrated into or attached to the at least one holding member external to the sterile cover.

13. The system of claim 12, further comprising a processor, wherein the processor is configured to register the head mounted display in a coordinate system using the at least one marker.

14. The system of claim 12, wherein the system is configured to track the head mounted display during a surgical procedure.

15. The system of claim 12 further comprising at least one magnetic coupling mechanism, wherein the at least one magnetic coupling mechanism is configured to removably attach the at least one marker to the at least one holding member.

16. The system of claim 15, wherein the at least one holding member comprises a proximal and a distal end, wherein the proximal end of the holding member is attached to the head mounted display, and wherein the at least one marker is attached to the distal end of the holding member.

17. The system of claim 15, wherein the at least one magnetic coupling mechanism comprises at least one magnetic element, and wherein the at least one magnetic element is attached to the distal end of the at least one holding member, to the at least one marker, or to the distal end of the at least one holding member and to the at least one marker.

18. The system of claim 15, wherein at least one holding member is configured to be removably attached to the head mounted display.

* * * * *